(12) United States Patent
Hansen et al.

(10) Patent No.: US 12,178,736 B2
(45) Date of Patent: *Dec. 31, 2024

(54) OSTOMY SYSTEM BASE PLATE INCLUDING ELECTRICAL TERMINALS AND A COUPLING PART ATTACHABLE TO A MONITOR DEVICE

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK); Lars Molzen, Kongens Lyngby (DK); Torben Holst Nielsen, Hedehusene (DK); Lisbeth Grenaae Jeppesen, Copenhagen OE (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,526

(22) Filed: Feb. 9, 2023

(65) Prior Publication Data
US 2023/0190509 A1 Jun. 22, 2023

Related U.S. Application Data

(63) Continuation of application No. 16/955,055, filed as application No. PCT/DK2018/050417 on Dec. 20, 2018, now Pat. No. 11,607,334.

(30) Foreign Application Priority Data

Dec. 22, 2017 (DK) .......................... PA 2017 70981
Feb. 20, 2018 (DK) .......................... PA 2018 70105
(Continued)

(51) Int. Cl.
*A61F 5/44* (2006.01)
*A61F 5/443* (2006.01)
(Continued)

(52) U.S. Cl.
CPC ............ *A61F 5/4404* (2013.01); *A61F 5/443* (2013.01); *A61F 5/445* (2013.01); *A61F 2005/4486* (2013.01)

(58) Field of Classification Search
CPC ........ A61F 5/4404; A61F 5/443; A61F 5/445; A61F 5/44; A61F 2005/4486; A61M 1/90
See application file for complete search history.

(56) References Cited

U.S. PATENT DOCUMENTS

| 2,054,535 A | 9/1936 | Diack |
| 2,327,514 A | 8/1943 | Fenwick |

(Continued)

FOREIGN PATENT DOCUMENTS

| AU | 2007342523 B2 | 7/2011 |
| CA | 2202199 C | 8/2006 |

(Continued)

OTHER PUBLICATIONS

International Preliminary Report on Patentability received for PCT Patent Application No. PCT/DK2019/050243, mailed on Feb. 25, 2021, 12 pages.

(Continued)

*Primary Examiner* — Benjamin J Klein
*Assistant Examiner* — Hans Kaliher
(74) *Attorney, Agent, or Firm* — Coloplast Corp., Coloplast A/S; Nick Baumann

(57) ABSTRACT

A base plate for an ostomy system includes a monitor interface having a plurality of terminals for electrical coupling of a monitor device to the base plate and a coupling part to attach the base plate to the monitor device.

16 Claims, 43 Drawing Sheets

(30) Foreign Application Priority Data

Feb. 20, 2018 (DK) .................. PA 2018 70107
Feb. 20, 2018 (DK) .................. PA 2018 70108
Feb. 20, 2018 (DK) .................. PA 2018 70110

(51) Int. Cl.
*A61F 5/445* (2006.01)
*A61F 5/448* (2006.01)

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,808,354 A | 4/1974 | Feezor et al. |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,519,644 A | 5/1996 | Benton |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,714,225 A | 2/1998 | Hansen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,846,558 A | 12/1998 | Nielsen et al. |
| 5,876,855 A | 3/1999 | Wong et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,078,261 A | 6/2000 | Davsko |
| 6,103,033 A | 8/2000 | Say et al. |
| 6,135,986 A | 10/2000 | Leisner et al. |
| 6,165,005 A | 12/2000 | Mills et al. |
| 6,171,289 B1 * | 1/2001 | Millot ............ A61F 5/443 604/336 |
| 6,206,864 B1 | 3/2001 | Kavanagh et al. |
| 6,241,704 B1 | 6/2001 | Peterson et al. |
| 6,246,330 B1 | 6/2001 | Nielsen |
| 6,270,445 B1 | 8/2001 | Dean, Jr. et al. |
| 6,297,422 B1 | 10/2001 | Hansen et al. |
| 6,407,308 B1 | 6/2002 | Roe et al. |
| 6,433,244 B1 | 8/2002 | Roe et al. |
| 6,433,695 B1 | 8/2002 | Kai et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,659,989 B1 | 12/2003 | Otto |
| 6,677,859 B1 | 1/2004 | Bensen |
| 6,764,474 B2 | 7/2004 | Nielsen et al. |
| 7,049,478 B1 | 5/2006 | Smith |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,326,051 B1 | 12/2012 | Hobbs |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,439,883 B1 | 5/2013 | Johnsen |
| 8,449,471 B2 | 5/2013 | Tran |
| 8,474,338 B2 | 7/2013 | Gelman et al. |
| 8,500,718 B2 | 8/2013 | Locke et al. |
| 8,507,081 B2 | 8/2013 | Strobech et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,464 B2 | 9/2014 | Hanuka et al. |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,566,383 B2 | 2/2017 | Yodfat et al. |
| 9,629,779 B2 | 4/2017 | Grum-Schwensen et al. |
| 9,629,964 B2 | 4/2017 | Wuepper |
| 9,675,267 B2 | 6/2017 | Laakkonen et al. |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,426,342 B2 | 10/2019 | Hresko et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,219,436 B2 | 1/2022 | Mayberg |
| 11,238,133 B1 | 2/2022 | Brewer et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,491,042 B2 | 11/2022 | Seres et al. |
| 11,534,323 B2 | 12/2022 | Hansen et al. |
| 11,540,937 B2 | 1/2023 | Hansen et al. |
| 11,547,595 B2 | 1/2023 | Hansen et al. |
| 11,547,596 B2 | 1/2023 | Hansen et al. |

(56) References Cited

U.S. PATENT DOCUMENTS

| | | |
|---|---|---|
| 11,559,423 B2 | 1/2023 | Speiermann et al. |
| 11,559,426 B2 | 1/2023 | Sletten et al. |
| 11,612,512 B2 | 3/2023 | Hansen et al. |
| 2001/0041920 A1 | 11/2001 | Starkweather et al. |
| 2001/0051787 A1 | 12/2001 | Haller et al. |
| 2002/0013613 A1 | 1/2002 | Haller et al. |
| 2002/0019615 A1 | 2/2002 | Roe et al. |
| 2002/0109621 A1 | 8/2002 | Khair et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0038325 A1 | 2/2005 | Moll |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0142796 A1 | 6/2007 | Mosbacher et al. |
| 2007/0185464 A1 | 8/2007 | Fattman et al. |
| 2007/0203407 A1 | 8/2007 | Hoss et al. |
| 2007/0204691 A1 | 9/2007 | Bogner et al. |
| 2008/0038536 A1 | 2/2008 | Strobech et al. |
| 2008/0041792 A1 | 2/2008 | Crnkovich et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0255808 A1 | 10/2008 | Hayter |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0009342 A1 | 1/2009 | Karjalainen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1* | 2/2010 | Thirstrup ............... A61F 5/4404 340/657 |
| 2010/0036206 A1 | 2/2010 | Lorio |
| 2010/0072271 A1 | 3/2010 | Thorstensson |
| 2010/0076275 A1 | 3/2010 | Chu et al. |
| 2010/0106220 A1 | 4/2010 | Ecker et al. |
| 2010/0114047 A1 | 5/2010 | Song et al. |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2011/0144470 A1 | 6/2011 | Mazar et al. |
| 2011/0191044 A1 | 8/2011 | Stafford |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0089037 A1 | 4/2012 | Bishay et al. |
| 2012/0143154 A1 | 6/2012 | Edvardsen et al. |
| 2012/0143155 A1 | 6/2012 | Edvardsen et al. |
| 2012/0172673 A1 | 7/2012 | Friedman et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2012/0304767 A1 | 12/2012 | Howard et al. |
| 2012/0323086 A1 | 12/2012 | Hansen |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0307570 A1 | 11/2013 | Bosaeus et al. |
| 2013/0324955 A1 | 12/2013 | Wong et al. |
| 2013/0332085 A1 | 12/2013 | Yang et al. |
| 2014/0051946 A1 | 2/2014 | Arne et al. |
| 2014/0128815 A1 | 5/2014 | Cabiri et al. |
| 2014/0133290 A1 | 5/2014 | Yokoo et al. |
| 2014/0200426 A1 | 7/2014 | Taub et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0272495 A1 | 10/2015 | Greener |
| 2015/0328389 A1 | 11/2015 | Heppe |
| 2015/0351690 A1 | 12/2015 | Toth et al. |
| 2015/0374896 A1 | 12/2015 | Du et al. |
| 2016/0008182 A1 | 1/2016 | Prokopuk et al. |
| 2016/0015570 A1 | 1/2016 | Heinecke et al. |
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |

(56) References Cited

U.S. PATENT DOCUMENTS

| | | |
|---|---|---|
| 2016/0158056 A1 | 6/2016 | Davis et al. |
| 2016/0158517 A1 | 6/2016 | Nebbia |
| 2016/0158969 A1 | 6/2016 | Mclane et al. |
| 2016/0166438 A1 | 6/2016 | Rovaniemi |
| 2016/0178387 A1 | 6/2016 | Yamasaki et al. |
| 2016/0198996 A1 | 7/2016 | Dullen |
| 2016/0218555 A1 | 7/2016 | Slaby et al. |
| 2016/0235581 A1 | 8/2016 | Keleny et al. |
| 2016/0235582 A1 | 8/2016 | Moavenian |
| 2016/0242654 A1 | 8/2016 | Quinlan et al. |
| 2016/0278990 A1 | 9/2016 | Chen |
| 2016/0284084 A1 | 9/2016 | Gurcan et al. |
| 2016/0305776 A1 | 10/2016 | Mrtensson et al. |
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | Dimaio et al. |
| 2017/0079576 A1 | 3/2017 | Stroebech et al. |
| 2017/0090236 A1 | 3/2017 | Yeh et al. |
| 2017/0098044 A1 | 4/2017 | Lai et al. |
| 2017/0112658 A1 | 4/2017 | Hosono |
| 2017/0113001 A1 | 4/2017 | Trock |
| 2017/0156920 A1 | 6/2017 | Hunt et al. |
| 2017/0181628 A1 | 6/2017 | Burnette et al. |
| 2017/0262986 A1 | 9/2017 | Xiong et al. |
| 2017/0319073 A1 | 11/2017 | Dimaio et al. |
| 2017/0340474 A1 | 11/2017 | Thirstrup et al. |
| 2017/0340498 A1 | 11/2017 | Tessmer et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2017/0367654 A1 | 12/2017 | Cheng et al. |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0298240 A1 | 10/2018 | Chatterjee et al. |
| 2018/0318475 A1 | 11/2018 | Thomson et al. |
| 2018/0344533 A1 | 12/2018 | Rovaniemi |
| 2019/0008439 A1 | 1/2019 | Sageder et al. |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0378602 A1 | 12/2022 | Hansen et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |

(56) References Cited

U.S. PATENT DOCUMENTS

| | | |
|---|---|---|
| 2023/0117727 A1 | 4/2023 | Hansen et al. |
| 2023/0118594 A1 | 4/2023 | Speiermann et al. |
| 2023/0141297 A1 | 5/2023 | Herold et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0329893 A1 | 10/2023 | Olsen et al. |
| 2023/0338005 A1 | 10/2023 | Barthe et al. |

FOREIGN PATENT DOCUMENTS

| | | |
|---|---|---|
| CA | 2540756 C | 1/2008 |
| CA | 3009449 C | 9/2019 |
| CA | 3002372 C | 3/2021 |
| CA | 2947016 C | 2/2023 |
| CN | 203786580 U | 8/2014 |
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| CN | 105615896 B | 5/2019 |
| CN | 105359167 B | 6/2019 |
| DE | 3437950 A1 | 4/1985 |
| DE | 3836590 A1 | 5/1990 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0800804 A1 | 10/1997 |
| EP | 1275357 A2 | 1/2003 |
| EP | 1188157 B1 | 12/2005 |
| EP | 2000083 A2 | 12/2008 |
| EP | 2108345 A1 | 10/2009 |
| EP | 2453851 A2 | 5/2012 |
| EP | 2489561 A2 | 8/2012 |
| EP | 2601915 A1 | 6/2013 |
| EP | 2654646 A2 | 10/2013 |
| EP | 2738960 A1 | 6/2014 |
| EP | 3064179 A1 | 9/2016 |
| EP | 3213727 A1 | 9/2017 |
| EP | 3226946 A1 | 10/2017 |
| GB | 2219679 A | 12/1989 |
| GB | 2225951 A | 6/1990 |
| GB | 2308306 A | 6/1997 |
| GB | 2343628 A | 5/2000 |
| GB | 2465742 A | 6/2010 |
| GB | 2486968 A | 7/2012 |
| GB | 2542093 A | 3/2017 |
| GB | 2561193 A | 10/2018 |
| JP | 04-074882 A | 3/1992 |
| JP | 06-152077 A | 5/1994 |
| JP | 09-010184 A | 1/1997 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2009-519751 A | 5/2009 |
| JP | 2014-033745 A | 2/2014 |
| JP | 2014-054368 A | 3/2014 |
| KR | 10-1056989 B1 | 8/2011 |
| KR | 10-2012-0003987 A | 1/2012 |
| KR | 20-0485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/007355 A2 | 1/2011 |
| WO | 2011003420 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2013164517 A1 | 11/2013 |
| WO | 2014/004207 A1 | 1/2014 |
| WO | 2014/086369 A1 | 6/2014 |
| WO | 2014116816 A1 | 7/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2016/132738 A1 | 8/2016 |
| WO | 2016124202 A1 | 8/2016 |
| WO | 2016/166731 A1 | 10/2016 |
| WO | 2016162038 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/120432 A1 | 6/2019 |
| WO | 2019/161859 A1 | 8/2019 |
| WO | 2019/161860 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

OTHER PUBLICATIONS

International Search Report and Written Opinion received for PCT Patent Application No. PCT/DK2019/050243, mailed on Nov. 25, 2019, 15 pages.

\* cited by examiner

OSTOMY SYSTEM BASE PLATE INCLUDING ELECTRICAL TERMINALS AND A COUPLING PART ATTACHABLE TO A MONITOR DEVICE

The present disclosure relates to an ostomy system, devices thereof, method of manufacturing and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
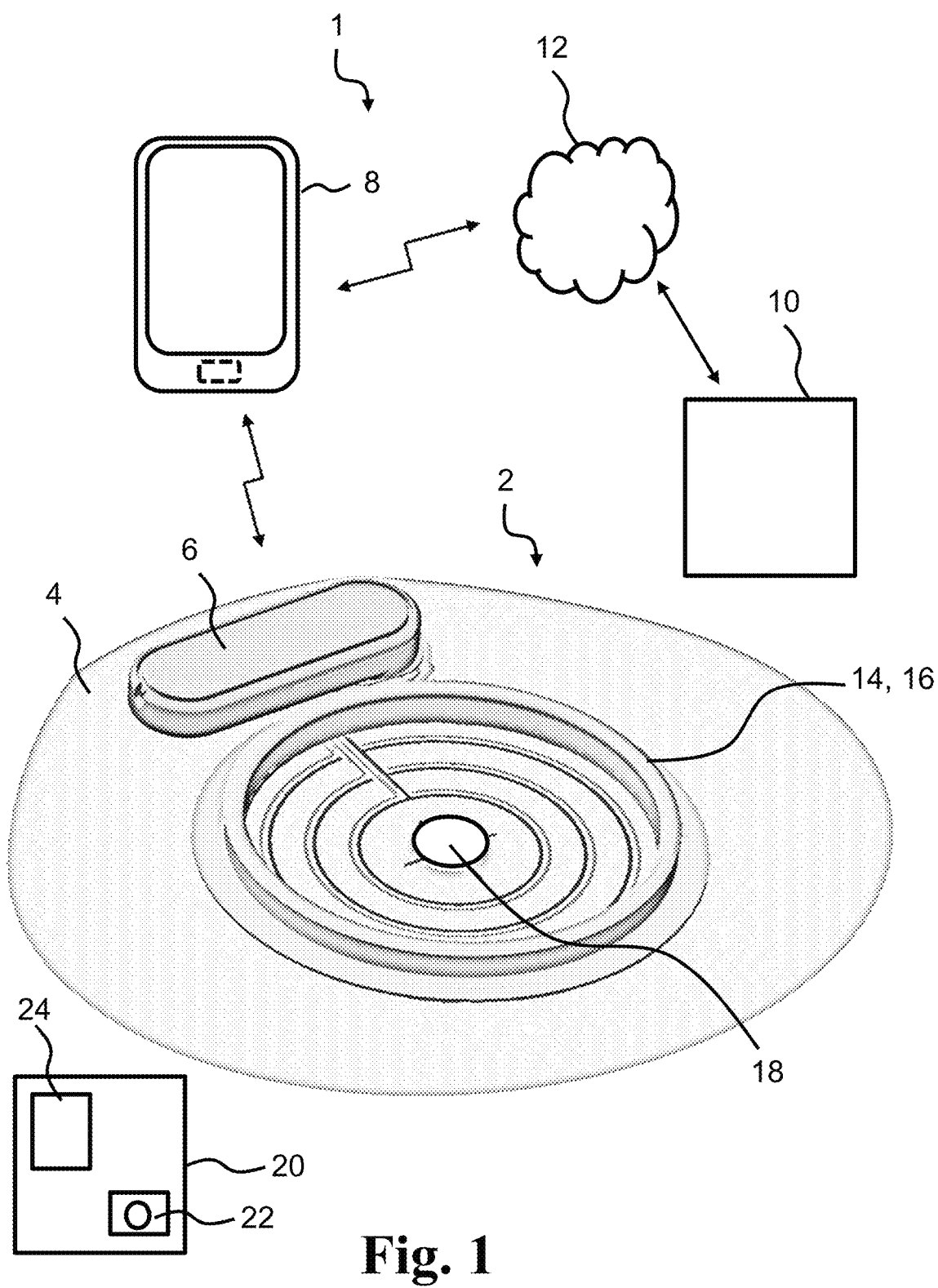
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, for example "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"-moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the peristomal skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

Figure 16:
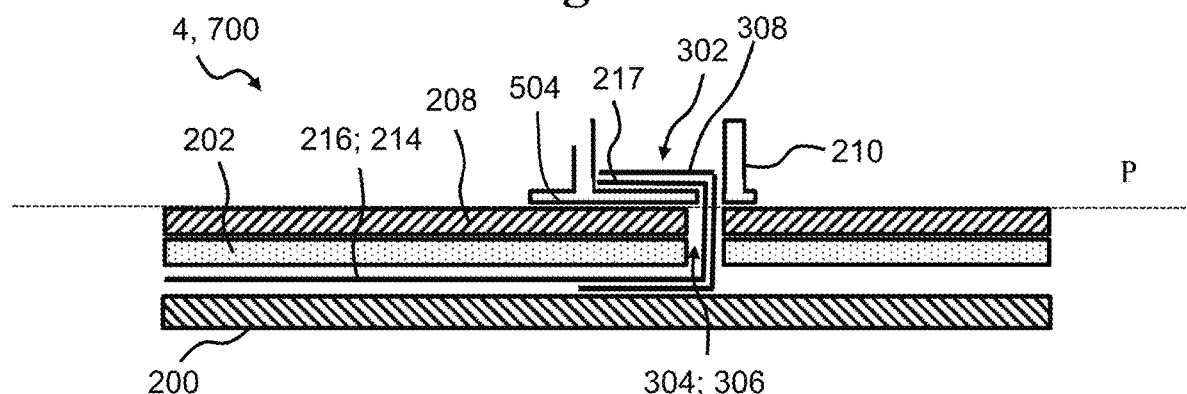
FIG. 16 shows a schematic representation of part of a base plate and a sensor assembly part.
Figure 25:
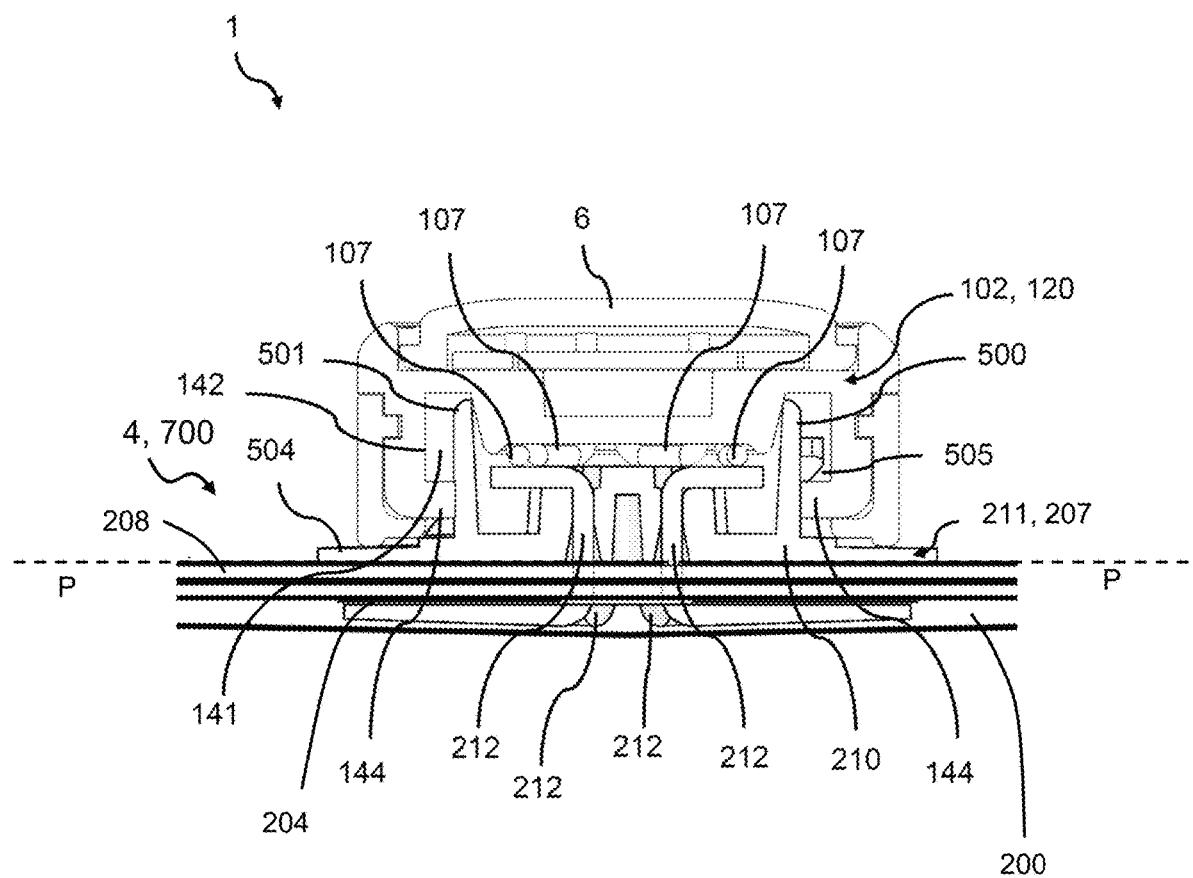
FIG. 25 is a cross-sectional schematic illustration of an exemplary monitor device and an exemplary base plate,
FIG. 26 schematically illustrates waterproofing elements,
FIG. 27 schematically illustrates an exemplary coupling part,
FIG. 28 schematically illustrates an exemplary coupling part,
FIG. 29 schematically illustrates an exemplary coupling part,
FIG. 30 schematically illustrates an exemplary coupling part,
FIG. 31 schematically illustrates parts of an exemplary monitor device
FIG. 32 schematically illustrates an exemplary coupling part.
Figure 41:
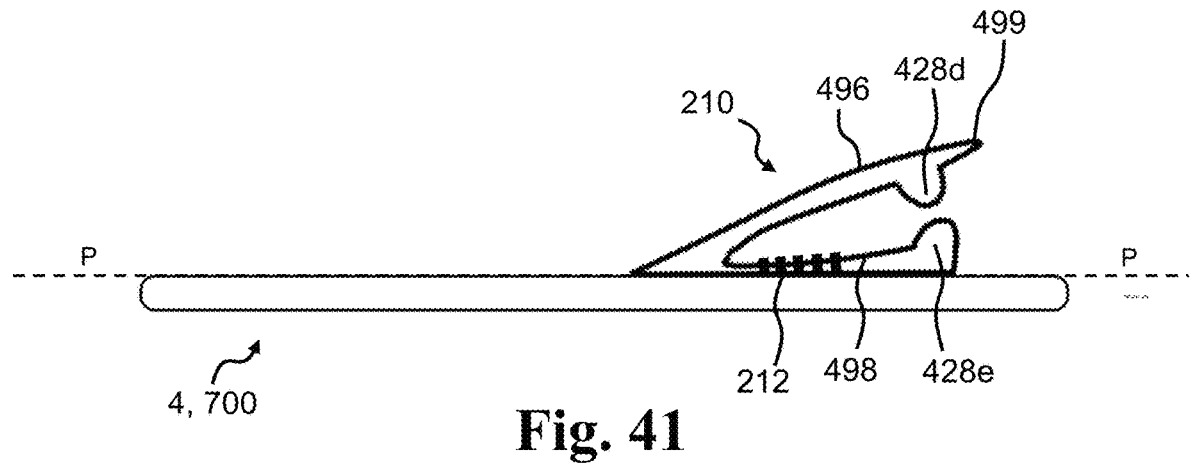

The term "base plate plane" is defined by the extent of the top layer of a base plate, thus the base plate plane is substantially perpendicular to the axial direction. If the base plate comprising a curved surface, the base plate plane is defined by the tangent at the portion, where a coupling part for coupling a monitor device to a base plate is positioned at the base plate. Thus, the "base plate plane" is parallel to a base of the coupling part of the base plate. In other words, the base plate plane is defined as the linear tangent to the point of mounting a monitor device. The base plate plane P is illustrated in FIGS. 16, 25 and 41.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, for example a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, volume and rapidness of moisture propagation in the adhesive material provided for attaching the base plate to the skin surface of a user. Depending on the nature of the pattern of moisture propagation in the adhesive, the ostomy system and devices thereof enable providing information to the user about a reduction of adhesion, and in turn enable providing an indication to the user of the extent of adhesion loss and thus the remaining time frame for replacing the ostomy appliance without experiencing leakage and/or potential for skin irritation.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled for example with a mechanical and/or an adhesive coupling, for example to allow that a plurality of ostomy pouches can be utilized (exchanged) with one base plate. Further, a two-part ostomy appliance may facilitate correct application of the base plate to skin, for example to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, for example integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, for example by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, for example together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted centre adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a centre point.

The first adhesive layer may be made of a first composition. The first composition may comprise one or more polyisobutenes and/or styrene-isoprene-styrene. The first composition may comprise one or more hydrocolloids.

The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, for example to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, for example in the range from 0.2 mm to 1.2 mm.

The first adhesive layer may have a primary thickness in a primary part of the first adhesive layer, for example in a primary region within a primary radial distance or in a primary radial distance range from the centre point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, for example 30 mm.

The first adhesive layer may have a secondary thickness in a secondary part of the first adhesive layer, for example in a secondary region outside a secondary radial distance or in a secondary radial distance range from the centre point of the stomal opening. The secondary thickness may be in the range from 0.2 mm to 1.0 mm, such as about 0.5 mm.

The secondary radial distance may be in the range from 20 mm to 50 mm, such as in the range from 25 mm to 35 mm, for example 30 mm.

The base plate and/or the sensor assembly part may comprise a second layer. The second layer may be a second adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a centre point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, for example in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, for example some or all the electrodes, may be arranged between the first adhesive layer and the second adhesive layer. The electrodes may be arranged in an electrode assembly, for example an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, for example the electrode assembly, may comprise a first electrode, a second electrode and optionally a third electrode. The base plate and/or the sensor assembly part, for example the electrode assembly, may comprise a fourth electrode and/or a fifth electrode. The base plate and/or the sensor assembly part, for example the electrode assembly, optionally comprises a sixth electrode. The base plate and/or the sensor assembly part, for example the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (for example silver, copper, gold, titanium, aluminium, stainless steel), ceramic (for example ITO), polymeric (for example PEDOT, PANI, PPy), and carbonaceous (for example carbon black, carbon nanotube, carbon fibre, graphene, graphite) materials.

Two electrodes of the electrode assembly may form a sensor. The first electrode and the ground electrode (for example first electrode part of the ground electrode) may form a first sensor or first electrode pair. The second electrode and the ground electrode (for example second electrode part of the ground electrode) may form a second sensor or second electrode pair. The third electrode and the ground electrode (for example third electrode part of the ground electrode) may form a third sensor or third electrode pair. The fourth electrode and the ground electrode (for example fourth electrode part of the ground electrode) may form a fourth sensor or fourth electrode pair. The fifth electrode and the ground electrode (for example fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, for example printed, on the proximal side of the support layer. One or more electrodes may be formed, for example printed, on the distal side of the support layer. The electrode assembly, such as the support layer of the electrode assembly, may have a stomal opening, such as an electrode assembly stomal opening and/or a support layer stomal opening, with a centre point.

The support layer may comprise polymeric (for example polyurethane, PTFE, PVDF) and/or ceramic (for example alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly, may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, for example to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (for example polyurethane, PTFE, PVDF) and/or ceramic (for example alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a centre point.

The base plate and/or the sensor assembly part may comprise a top layer. The top layer is a protective layer protecting the adhesive layer(s) from external strains and stress when the user wears the ostomy appliance. The electrodes, for example some or all the electrodes, may be arranged between the first adhesive layer and the top layer. The top layer may have a stomal opening, such as a top layer stomal opening, with a centre point. The top layer may have a thickness in the range from 0.01 mm to 1.0 mm, for example in the range from 0.02 mm to 0.2 mm, such as 0.04 mm.

The base plate and/or the sensor assembly part comprises a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part is configured to electrically and/or mechanically couple the ostomy appliance and the monitor device.

The monitor interface of the base plate and/or the sensor assembly part may comprise, for example as part of a first connector of the monitor interface, a coupling part for forming a mechanical connection, such as a releasable coupling between the monitor device and the base plate and/or the sensor assembly part. The coupling part may be configured to engage with a coupling part of the monitor device (for example a monitor device coupling part) for releasably coupling the monitor device to the base plate and/or the sensor assembly part.

The monitor interface of the base plate and/or the sensor assembly part may comprise, for example as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The centre point may be defined as a centre of the coupling ring.

The base plate and/or the sensor assembly part may have a stomal opening, for example with a centre point. The stomal opening of the base plate and/or the sensor assembly part may be formed collectively of co-axially positioned stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part.

The stomal opening may be a through-going passage of the base plate and/or the sensor assembly part. The stomal opening may be arranged substantially in the centre of the base plate and/or the sensor assembly part. The stomal opening(s) of the layers of the base plate and/or the sensor assembly part may be arranged substantially in the centre of the respective layer. The stomal opening is configured to receive a stoma of the user and/or the stomal opening is configured to allow output from the stoma to pass through the stomal opening an into an ostomy pouch attached to the base plate. For example, the stomal opening is configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate and/or the sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, for example the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, for example the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, for example to be applied in the first criteria set. The first threshold set may comprise a first primary threshold value. The first threshold set may comprise a first secondary threshold value. The first threshold set may comprise a first tertiary threshold value.

The first criteria set may be given by $$(P\_1\_1 < TH\_1\_1),$$

$$(P\_2\_1 > TH\_1\_2), \text{ and}$$

$$(P\_3\_1 > TH\_1\_3),$$

wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate and/or the sensor assembly part. The first threshold values (TH_1_1, TH_1_2 and TH_1_3) may be the same or different, for example depending on the electrode configuration of the base plate and/or the sensor assembly part. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, for example to be applied in the second criteria set. The second threshold set may comprise a second primary threshold value. The second threshold set may comprise a second secondary threshold value. The second threshold set may comprise a second tertiary threshold value.

The second criteria set may be given by (P_1_1<TH_2_1), (P_2_1<TH_2_2), and (P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part. The second threshold values (TH_2_1, TH_2_2 and TH_2_3) may be the same or different, for example depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by (P_1_1>TH_D_1), (P_2_1>TH_D_2), and (P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, for example depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, for example the first adhesive layer is eroded to the third radial distance of the third electrode pair.

The third criteria set may be given by (P_1_1<TH_3_1), (P_2_1<TH_3_2), and (P_3_1<TH_3_3)

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, $TH\_3\_2$ is a third secondary threshold value, $P\_3\_1$ is a third primary parameter based on the third parameter data and indicative of the resistance between the third electrode pair, $TH\_3\_3$ is a third tertiary threshold value, and wherein the third operating state is indicative of high degree of radial erosion on the base plate and/or the sensor assembly part. The third threshold values ($TH\_3\_1$, $TH\_3\_2$ and $TH\_3\_3$) may be the same or different, for example depending on the electrode configuration of the base plate and/or the sensor assembly part. The third primary criterion ($P\_1\_1 < TH\_3\_1$) and/or the third secondary criterion ($P\_2\_1 < TH\_3\_2$) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by $$(P\_4\_1 < TH\_4\_4)$$

wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, for example for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, for example with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part (may alternatively be denoted a device coupling part or a monitor device coupling part) for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, for example the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, for example wirelessly connecting, the monitor device to one or more accessory devices. The second interface may comprise an antenna and a wireless transceiver, for example configured for wireless communication at frequencies in the range from 2.4 to 2.5 GHZ. The wireless transceiver may be a Bluetooth transceiver, i.e. the wireless transceiver may be configured for wireless communication according to Bluetooth protocol, for example Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, for example the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, for example as part of a first connector of the docking monitor interface, a coupling part for forming a mechanical connection, such as a releasable coupling between the monitor device and the docking station. The coupling part may be configured to engage with a coupling part of the monitor device (for example a monitor device coupling part) for releasably coupling the monitor device to the docking station.

The docking monitor interface of the docking station may comprise, for example as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a base plate and/or a sensor assembly part for an ostomy appliance, such as a base plate and/or a sensor assembly part as described above. The base plate and/or the sensor assembly part may comprise: a top layer, a first adhesive layer, an electrode assembly comprising a plurality of electrodes; and a monitor interface configured for connecting the base plate and/or the sensor assembly part to a monitor device. The base plate and/or the sensor assembly part may comprise additional layers and/or features as described above. The base plate and/or the sensor assembly part may extend substantially in a base plate plane. For example, layers of the base plate and/or the sensor assembly part, such as the top layer and/or the first adhesive layer may extend in the base plate plane.

The monitor interface may comprise a plurality of terminals electrically connected to the plurality of electrodes and configured to connect with respective terminals of the monitor device. The monitor interface may comprise a coupling part configured for coupling between the monitor device and the base plate and/or the sensor assembly part.

Also disclosed is a monitor device, such as a monitor device as described above, such as a monitor device for connecting to a base plate and/or a sensor assembly part of an ostomy appliance, such as the base plate and/or the sensor assembly part as described above, such as a base plate and/or a sensor assembly part extending substantially in a base plate plane. The monitor device may comprise: a monitor device housing; electronic circuitry; and an appliance interface configured for connecting the monitor device to the base plate and/or the sensor assembly part. The monitor device may comprise additional features, such as features described above. The electronic circuitry may be configured to receive ostomy data from a plurality of electrodes of the base plate and/or the sensor assembly part.

The appliance interface may comprise a plurality of terminals for connecting with the plurality of electrodes of the base plate and/or the sensor assembly part. The appliance interface may comprise a monitor device coupling part configured for coupling between the monitor device and the base plate and/or the sensor assembly part.

Also disclosed is an ostomy system comprising a base plate and/or a sensor assembly part and a monitor device, such as the base plate and/or the sensor assembly part as disclosed above, and the monitor device as disclosed above. The ostomy system may further comprise an ostomy pouch.

The coupling part may be configured to engage with a monitor device coupling part of the monitor device, and/or the monitor device coupling part may be configured to engage with a coupling part of the base plate and/or the sensor assembly part, by applying an engagement force on the monitor device in an engagement direction relative to the base plate and/or the sensor assembly part. The engagement force may be applied by a user of the base plate and/or monitor device. The engagement direction may form an engagement angle with the base plate plane, for example at the position of the coupling part (for example in situations where the base plate is provided with a curvature). The engagement angle may be less than 45 degrees, such as less than 40 degrees, such as less than 30 degrees, such as less than 20 degrees. The engagement direction may be substantially parallel to the base plate plane.

In an embodiment, the base plate for an ostomy appliance comprises a top layer defining a base plate plane P. The base plate comprises a first adhesive layer adapted to adhere the base plate to peristomal skin of a user, an electrode assembly and a monitor interface configured to electronically connect with the electrode assembly, where the monitor interface comprises a coupling part configured to form a releasably mechanically and/or electronically coupling between the base plate and a monitor device.

The coupling part is configured to engage and/or disengage with the monitor device allowing the monitor device to be coupled to the base plate by a motion in a direction corresponding to an acute angle of 45 degrees or less relative to the base plate plane P.

Hereby, the applied force for engagement is primarily in a radial direction rather than in axial direction with respect to the base plate and the abdomen of a user.

The coupling part may be configured to couple the monitor device to the base plate by a linear sliding motion or by a rotational motion.

When mechanically coupling parts, where one of the parts are mounted to a base plate several circumstances has to be taken into consideration.

A secure and user-friendly coupling mechanism should be provided, such as a mechanism which allow the user to hear and/or feel that the coupling is achieved. For example, a coupling mechanism comprising a click or a friction portion may be provided, for which the user will know, by hearing a click sound and/or by overcoming a friction threshold, that the coupling has been correctly achieved. Thus, a force threshold to achieve such sound and/or feel, defines a lower threshold for an applied engagement force range.

The abdomen and the peristomal skin are often relatively soft and flexible, and tests have shown that it may be difficult to allow engagement of two coupling parts by applying a force towards the abdomen in axial direction, as the abdomen may not be able to comfortably provide a counter pressure allowing the coupling parts to engage properly. Additionally, since the skin surrounding a stoma may be sensitive, particularly in the time period following the surgical procedure creating the stoma, applying a force to the skin resulting in the skin and abdomen to be significantly depressed may be painful and may even be destructive to the skin.

The amount of force necessary to engage and/or disengage the coupling parts is determined by the structure of the coupling parts and is a function of the amount of force necessary to (frictionally) engage the coupling parts of the monitor device and the base plate, which in turn, is limited, as indicated above, by the amount of force which can be acceptably applied to the skin (of the user) under the base plate.

A test has been performed to access how a constant force applied to an ostomy appliance system comprising a base plate on a substrate resembling an abdomen affects the ostomy appliance system, and how the system is affected in variable angles relative to the base plate plane P.

It has been desirable to evaluate an ostomy appliance system ability to provide a counter force to an applied pressure force, which will permit engagement of the coupling parts, without causing unnecessary discomfort to a user.

The tests performed showed that it may be advantageous to provide coupling parts by utilizing forces more in a direction parallel than perpendicular to the abdomen skin surface, i.e. more parallel than perpendicular to the base plate plane P.

By the present invention it is achieved that the forces applied for coupling a monitor device to a base plate are distributed more uniformly across the entire base plate and the adhesive layer surface, and the depression into the abdomen of a user is reduced. This in turn allows the necessary force needed to engage and/or disengage the coupling parts to be sufficient to provide the needed feedback in terms of the user feeling overcoming a friction threshold and/or hearing of a click, while at the same time reducing discomfort associated by depression of the peristomal skin of a user. Furthermore, the coupling will be made easier, if depression can be reduced.

For example, the monitor device, such as the monitor device coupling part, and the base plate and/or the sensor assembly part, such as the coupling part of the base plate and/or the sensor assembly part, may be transferred from being decoupled to being coupled by applying an engagement force on the monitor device in a direction where, for example, adhesive layers of the base plate and/or the sensor assembly part, provides for sufficient counterforce in order for the user to couple the monitor device to the base plate.

The coupling part may be configured to disengage with the monitor device coupling part of the monitor device, and/or the monitor device coupling part may be configured to disengage with a coupling part of the base plate and/or the sensor assembly part, by applying a disengagement force on the monitor device in a disengagement direction relative to the base plate and/or the sensor assembly part. The disengagement force may be applied by a user of the base plate and/or monitor device. The disengagement direction may be opposite the engagement direction. Alternatively, the disengagement direction may be perpendicular to the engagement direction. The disengagement direction may form a disengagement angle with the base plate plane, for example at the position of the coupling part (for example in situations where the base plate is provided with a curvature). The disengagement angle may be between 0 and 45 degrees, such as between 0 and 30 degrees, such as between 0 and 15 degrees. The disengagement direction may be substantially parallel to the base plate plane. The disengagement angle may be ±45 degrees with respect to the base plate plane.

For example, the monitor device, such as the monitor device coupling part, and the base plate and/or the sensor assembly part, such as the coupling part of the base plate and/or the sensor assembly part, may be transferred from being coupled to being decoupled by applying a disengagement force on the monitor device in a direction where, for example, adhesive layers of the base plate and/or the sensor assembly part, provides for sufficient counterforce in order for the user to decouple the monitor device.

Coupling and/or decoupling of the monitor device to the base plate and/or the sensor assembly part by application of a force which provides for sufficient counterforce, facilitates the user's ability to couple and/or decouple the monitor device, and reduce the necessity for providing a counterforce, for example by tightening abdominal muscles or similar. Thus, an easier coupling and/or decoupling of the monitor device to the base plate and/or the sensor assembly part is provided.

Providing for an easier coupling of the monitor device to the base plate and/or the sensor assembly part, may be useful for an ostomy user, since the ostomy appliance may be situated on the body in a position complicating coupling of the monitor device. For example, the ostomy appliance may be partly hidden, such that the user needs to use a mirror in order to see what he/she is doing in coupling the monitor device to the base plate and/or the sensor assembly part.

Also, the ostomy appliance may be positioned to restrict the possibility for the user to use both hands. It is therefore a further advantage of the present disclosure, that it may facilitate the coupling of the monitor device to the base plate and/or the sensor assembly part using only one hand.

Furthermore, the present disclosure exploits the adhesive properties of the base plate and adherence to the skin of the user in order to provide a sufficient counter force for coupling of the monitor device to the base plate and/or the sensor assembly part. Hence, specific user requirements and/or impact of individual circumstances are reduced, thereby providing a more reliable coupling method.

The monitor device may initially be positioned in an attachment position relative to the base plate and/or the sensor assembly part to couple the monitor device and the base plate and/or the sensor assembly part. From the attachment position, the monitor device is engaging with the base plate and/or the sensor assembly part, for example the monitor device coupling part is engaging with the coupling part of the base plate and/or the sensor assembly part to become coupled. After being engaged with the base plate and/or the sensor assembly part, for example after the monitor device coupling part is engaged with the coupling part of the base plate and/or the sensor assembly part, the monitor device is positioned in a coupled position relative to the base plate and/or the sensor assembly part. In the coupled position, the monitor device may be completely coupled to the monitor device.

The coupling part may be configured, such as further configured, to engage with the monitor device coupling part by a linear motion of the monitor device and/or the monitor device coupling part may be configured, such as further configured, to engage with the coupling part by the linear motion of the monitor device. The linear motion of the monitor device for engagement may be in the engagement direction. For example, the monitor device, such as the monitor device coupling part, and the base plate and/or the sensor assembly part, such as the coupling part of the base plate and/or the sensor assembly part, may be transferred from being decoupled to being coupled by a linear motion, such as a single linear motion, in the engagement direction of the monitor device relative to the base plate and/or the sensor assembly part.

The coupling part may be configured, such as further configured, to disengage with the monitor device coupling part by a linear motion of the monitor device and/or the monitor device coupling part may be configured, such as further configured, to disengage with the coupling part by the linear motion of the monitor device. The linear motion of the monitor device for disengagement may be in the disengagement direction. For example, the monitor device, such as the monitor device coupling part, and the base plate and/or the sensor assembly part, such as the coupling part of the base plate and/or the sensor assembly part, may be transferred from being coupled to being decoupled by a linear motion, such as a single linear motion, in the disengagement direction of the monitor device relative to the base plate and/or the sensor assembly part.

Using a linear motion to couple and/or decouple the monitor device to the base plate and/or the sensor assembly part may further facilitate a simple and easy coupling of the monitor device to the base plate and/or the sensor assembly part, for example only one simple movement may be needed to couple the monitor device to the base plate and/or the sensor assembly part.

Alternatively, the coupling part may be configured, such as further configured, to engage with the monitor device coupling part by a rotational motion of the monitor device and/or the monitor device coupling part may be configured, such as further configured, to engage with the coupling part by the rotational motion of the monitor device. The rotational motion of the monitor device for engagement may be about a rotation axis. For example, the monitor device, such as the monitor device coupling part, and the base plate and/or the sensor assembly part, such as the coupling part of the base plate and/or the sensor assembly part, may be transferred from being decoupled to being coupled by a rotational motion, such as a single rotational motion, about the rotation axis. The rotation axis may be substantially perpendicular to the engagement direction.

The coupling part may be configured, such as further configured, to disengage with the monitor device coupling part by a rotational motion of the monitor device and/or the monitor device coupling part may be configured, such as further configured, to disengage with the coupling part by the rotational motion of the monitor device. The rotational motion of the monitor device for disengagement may be about a rotation axis. For example, the monitor device, such as the monitor device coupling part, and the base plate and/or the sensor assembly part, such as the coupling part of the base plate and/or the sensor assembly part, may be transferred from being coupled to being decoupled by a rotational motion, such as a single rotational motion, about the rotation axis. The rotation axis for disengagement may be the same rotation axis as for engagement. The rotation axis for disengagement may be substantially perpendicular to the disengagement direction.

The rotational motion may be less than 360 degrees, such as less than 180 degrees, such as less than 120 degrees. For example, the rotational motion may be between 40-180 degrees, such as between 60-120 degrees. The rotational motion may be clockwise or counter-clockwise. The rotational motion may be from the attachment position, for example the initial position of the monitor device relative to the base plate and/or the sensor assembly part when initiating coupling of the base plate and/or the sensor assembly part and monitor device, to a coupled position, for example the final position of the monitor device relative to the base plate and/or the sensor assembly part when the monitor device and base plate and/or the sensor assembly part are fully coupled.

The monitor device may comprise electronic circuitry, for example electronic circuitry for receiving, processing, storing and/or transmitting signals and/or data. The electronic circuitry may, for example, include a processor, a wireless communication unit, memory etc. The electronic circuitry may be enclosed by the monitor device housing.

The coupling part of the base plate and/or the sensor assembly part and/or the monitor device coupling part of the monitor device may include a slot or a track or similar. The slot or track may be substantially linear. The slot or track may be configured to receive a protrusion of the corresponding coupling part, for example a protrusion of the coupling part of the base plate and/or the sensor assembly part, and/or of the monitor device coupling part of the monitor device. For example, the coupling part of the base plate and/or the sensor assembly part may comprise the slot or track, and the monitor device coupling part of the monitor device may comprise the protrusion. Alternatively or additionally, the monitor device coupling part of the monitor device may comprise the slot or track, and the coupling part of the base plate and/or the sensor assembly part may comprise the protrusion.

The top layer and/or the first adhesive layer may be substantially planar, for example prior to being applied to a user's skin. The top layer and/or the first adhesive layer may extend in the base plate plane.

The engagement direction and/or the disengagement direction may be towards a stomal opening of the base plate and/or the sensor assembly part. For example, the engagement direction and/or the disengagement direction may be from an edge of the base plate and/or the sensor assembly part, such as from an edge of the top layer and/or first adhesive layer. The engagement direction and/or the disengagement direction may be a radial direction of the base plate and/or the sensor assembly part. Alternatively, the engagement direction and/or the disengagement direction may be substantially perpendicular to a radial direction of the base plate and/or the sensor assembly part.

The monitor device, such as the monitor device housing, may have a first surface and a second surface. The first surface may be opposite the second surface. The first surface and/or the second surface may be substantially flat. The monitor device may comprise a rim surface between the first surface and the second surface. The rim surface may be substantially perpendicular to the first surface and/or the second surface.

The monitor device coupling part may be provided at the rim surface, such as at a first part of the rim surface. For example, the monitor device coupling part may be provided by an opening in the rim surface, such as in the first part of the rim surface. Alternatively, the monitor device coupling part may be provided at the first surface and/or the second surface, such as an opening or a recess in the first surface and/or the second surface.

The plurality of terminals of the monitor device may be configured for electrically connecting with the plurality of electrodes of the base plate and/or the sensor assembly part, such as by electrically connecting with the plurality of terminals of the base plate and/or the sensor assembly part.

The base plate and/or the sensor assembly part, such as the monitor interface of the base plate and/or the sensor assembly part, such as the coupling part of the monitor interface, may comprise a locking mechanism. Alternatively or additionally, the monitor device may comprise a locking mechanism. The locking mechanism(s) may be configured to lock the monitor device in the coupled position with the base plate and/or the sensor assembly part. For example, the locking mechanism(s) may provide that the monitor device is maintained in the coupled position with the base plate and/or the sensor assembly part. The locking mechanism(s) may be configured to automatically lock the monitor device in the coupled position with the base plate and/or the sensor assembly part. For example, the locking mechanism(s) may be biased, for example spring biased, towards locking of the locking mechanism(s). For example, the locking mechanism may comprise biasing means, for example a spring, that biases the locking mechanism towards a locked position. The locking mechanism(s) may be configured to unlock the monitor device from the coupled position with the base plate and/or the sensor assembly part upon user interaction. Alternatively or additionally, the locking mechanism(s) may be configured to lock the monitor device in the coupled position with the base plate and/or the sensor assembly part upon user interaction.

The base plate and/or the sensor assembly part, such as the monitor interface of the base plate and/or the sensor assembly part, such as the coupling part of the monitor interface, may comprise a locking section. Alternatively or additionally, the monitor device may comprise a locking section. The locking section(s) may be configured to cooperate with a respective locking mechanism. For example, a locking section of the base plate and/or the sensor assembly part may be configured to cooperate with a locking mechanism of the monitor device, and/or a locking section of the monitor device may be configured to cooperate with a locking mechanism of the base plate and/or the sensor assembly part.

The locking section(s) may comprise a hole extending through a coupling part, such as the coupling part of the base plate and/or the sensor assembly part and/or the monitor device coupling part of the monitor device. Alternatively or additionally, the locking section(s) may comprise a protrusion protruding from a surface of the coupling part and/or monitor device coupling part. Alternatively or additionally, the locking section(s) may comprise a first indent in a first edge of the coupling part and/or monitor device coupling part and a second indent in a second edge of the coupling part and/or monitor device coupling part. The first edge may be opposite the second edge. Alternatively or additionally, the locking section(s) may comprise a recess in a surface of the coupling part and/or monitor device coupling part.

The monitor device may comprise an opening for receiving the coupling part of the base plate and/or the sensor assembly part. For example, the monitor device coupling part may be provided by the opening for receiving the coupling part of the base plate and/or the sensor assembly part. The locking mechanism may comprise a locking component positioned inside the opening, such as a pin configured to engage a hole of the locking section. Alternatively or additionally, the monitor device may comprise a recess for receiving the coupling part of the base plate and/or the sensor assembly part. For example, the monitor device coupling part may be provided by the recess for receiving the coupling part of the base plate and/or the sensor assembly part. The locking mechanism may comprise a locking component positioned inside the recess, such as a pin configured to engage a hole of the locking section.

The base plate and/or the sensor assembly part and/or the monitor device may comprise a locking element (may alternatively be denoted an unlocking element). The locking element(s) may form part of the locking mechanism(s). The locking element(s) may be configured to unlock and/or lock the locking mechanism(s), for example upon user interaction with the locking element(s). For example, the locking element(s) may comprise button(s) for user interaction. For example, the locking element(s) may be engaged to lock the locking mechanism and/or the locking element(s) may be engaged to unlock the locking mechanism. User interaction with the locking element(s) may comprise deflection of one or more buttons or sliding of a slider etc.

The locking element(s), such as each of the locking elements, may comprise a first button. The first button may be deflectable in a first direction.

The first direction may be substantially parallel to the engagement direction, and/or the first direction may be substantially parallel to the disengagement direction. For example, the first direction may be substantially the same as the engagement direction and/or the disengagement direction. Alternatively, the first direction may be substantially opposite the engagement direction and/or the disengagement direction. Alternatively, the first direction may be substantially perpendicular to the engagement direction, and/or the first direction may be substantially perpendicular to the disengagement direction.

The locking element(s) may comprise a second button, such as a first button and a second button. The second button may be deflectable in a second direction.

The first direction may be substantially opposite the second direction. The first direction and the second direction being opposite may provide that the first button and the second button may be deflected, for example engaged, simultaneously by the user pinching the monitor device.

The first direction and/or the second direction may be substantially perpendicular to the engagement direction, and/or the first direction may be substantially parallel to the disengagement direction. Thereby, the user may pinch the monitor device and push/pull in the engagement direction and/or the disengagement direction.

The locking element(s) may comprise a slider. The slider may be slidable in a first slider direction. The slider may be spring loaded and biased towards a second slider direction. The first slider direction may be opposite the second slider direction. The first slider direction and/or the second slider direction may be substantially perpendicular to the engagement direction and/or the disengagement direction. Alternatively, the first slider direction and/or the second slider direction may be substantially parallel to the engagement direction and/or the disengagement direction, such as opposite the engagement direction and/or the disengagement direction.

The coupling part(s), such as the monitor device coupling part and/or the coupling part of the base plate and/or the sensor assembly part, may form a USB type plug or port. For example, the coupling part(s) may conform with a USB standard.

The coupling part may be positioned such that upon coupling the monitor device to the base plate and/or the sensor assembly part the top layer is disposed between the monitor device and the skin of the user. The monitor device may be configured such that upon coupling the monitor device to the base plate and/or the sensor assembly part the top layer of the base plate and/or the sensor assembly part is disposed between the monitor device and the skin of the user.

The monitor device may be a source of skin irritation, for example if the monitor device is in contact with the skin and/or if the monitor device is moving against the skin. Thus, it may be an advantage of the present disclosure, that the monitor device may be positioned, such that the base plate and/or the sensor assembly part creates a protective layer between the skin and the monitor device. Hence, skin irritation caused by the monitor device, may be reduced or avoided.

The coupling part may be positioned such that the monitor device is coupled to the base plate and/or the sensor assembly part on a distal side of the top layer. The coupling part may be positioned distal to the top layer. The coupling part may be positioned such that the monitor device, when coupled to the base plate and/or the sensor assembly part, is positioned between an edge of the top layer and a stomal opening of the base plate and/or the sensor assembly part, such as a top layer stomal opening of the top layer. The coupling part may be positioned such that the monitor device, when coupled to the base plate and/or the sensor assembly part, is positioned between the coupling part and the stomal opening of the base plate and/or the sensor assembly part, such as the top layer stomal opening of the top layer. Thus, the coupling part may be positioned near the edge of the top layer, such as less than 5 cm, such as less than 2 cm, such as less than 1 cm, from the edge of the top layer. Alternatively, the coupling part may be positioned at a distance from the edge of the top layer, such as more than 2 cm, such as more than 5 cm from the edge of the top layer. The distance from the edge of the top layer may be greater than a first dimension, such as a height, of the monitor device.

The coupling part may be positioned to form a first area between the coupling part and an edge of the top layer. The first area may be greater than a cross sectional area of the monitor device, such as the largest cross-sectional area of the monitor device. The monitor device may be shaped to have a cross sectional area, for example the largest cross-sectional area of the monitor device, that is smaller than the first area of the base plate and/or the sensor assembly part. For example, the first area may be such that the monitor device is contained within the first area when coupled to the base plate and/or the sensor assembly part. The coupling part may be substantially rectangular. Hence, the first area between the coupling part and the edge of the top layer may have a straight side defined by the coupling part. For example, the first area may be substantially triangular or rectangular and/or the first area may resemble half of an ellipse and/or the first area may resemble a pentagon.

An ostomy pouch may be attached to the base plate, such as for a two-part ostomy appliance. Alternatively, the base plate and the ostomy pouch may be provided together, such as a one-part ostomy appliance. The base plate, the sensor assembly part, the monitor device and/or the ostomy pouch may be configured to position the monitor device between the ostomy pouch and the base plate and/or the sensor assembly part. For example, to further avoid skin contact between the monitor device and the skin of the user.

The monitor device and/or the base plate and/or the sensor assembly part may comprise an attachment element. The attachment element may be configured to attach to the ostomy pouch, such as a part of the ostomy pouch, of the ostomy appliance. By attaching the ostomy pouch to the monitor device and/or the base plate, such as to the base plate near the monitor device, the monitor device may be further shielded from the skin of the user. Also, the monitor device may be hidden by the ostomy pouch. Also, the monitor device may be more securely retained, such as to avoid decoupling of the monitor device from the base plate and/or the sensor assembly part during use. Furthermore, the user may be made aware of the monitor device upon changing the ostomy pouch and/or the base plate, and the risk of discarding the monitor device with the ostomy pouch and/or the base plate may be reduced.

The attachment element may be in the form of a clamp, such as a clamp configured to clamp to an edge of the ostomy pouch. Alternatively or additionally, the attachment element may be in the form of a slit configured to receive an edge of the ostomy pouch. Alternatively or additionally, the attachment element may be in the form of a Velcro element, such as a Velcro element configured to attach to an opposing Velcro element of the ostomy pouch. Alternatively or additionally, the attachment element may be in the form of a magnetic material, such as a magnetic material configured to attach to an opposing magnetic material of the ostomy pouch.

The coupling part may be substantially flat. For example, the coupling part may extend substantially in a plane, such as the base plate plane.

The coupling part may comprise a first surface and a second surface. The second surface may be opposite the first surface. The second surface may be facing the top layer, such as in a proximal direction, for example the second surface may be facing the skin of the user. The first surface may be facing away from the top layer, such as in a distal direction, for example the first surface may be facing away from the skin of the user. The second surface of the coupling part and the top layer may be separated, for example to allow at least a part of the monitor device to be positioned between the second surface of the coupling part and the top layer, such as when the monitor device is connected to the base plate and/or the sensor assembly part.

The plurality of terminals may be provided on the second surface of the coupling part. Alternatively or additionally, the plurality of terminals may be provided on the first surface of the coupling part.

The coupling part may comprise a first coupling part section and a second coupling part section. The coupling part may be configured to receive at least a part of the monitor device between the first coupling part section and the second coupling part section. The first coupling part section and the second coupling part section may be biased towards each other. For example, the first coupling part section may be biased towards the second coupling part section and/or the second coupling part section may be biased towards the first coupling part. The first coupling part section may be deflectable from the second coupling part section. Alternatively or additionally, the second coupling part section may be deflectable from the first coupling part section.

The coupling part may comprise a loop element forming a conduit between a first opening and a second opening. Alternatively, the coupling part may comprise a flexible element configured to form the loop element. The coupling part may be configured to receive at least a part of the monitor device through the first opening and/or the second opening. For example, the at least part of the monitor device may extend into the first opening, through the conduit and out of the second opening, when the monitor device is coupled to the base plate and/or the sensor assembly part.

The monitor device may be configured to engage with the loop element of the base plate and/or the sensor assembly part. For example, the monitor device coupling part may comprise a first clip element, for example forming a first slit configured to receive an element of the base plate and/or the sensor assembly part, such as the loop element of the base plate and/or the sensor assembly part. The first slit may be formed between the first clip element and the monitor device housing.

The loop element may be formed by the top layer and/or the electrode assembly of the base plate and/or the sensor assembly part. For example, the coupling part and/or the loop element may be formed as part of the top layer and/or the electrode assembly. The top layer and/or the electrode assembly may form the loop element. For example, a first top layer part of the top layer and/or a first electrode assembly part of the electrode assembly may form the loop element. The loop element may be provided by looping around the first top layer part of the top layer and/or the first electrode assembly part of the electrode assembly to attach to a distal side of the base plate and/or the sensor assembly part. For example, the loop element may comprise a first loop end. The first loop end may be connected to a distal side of the top layer and/or a distal side of the first adhesive layer and/or a distal side of another optional layer. For example, the first loop end may be connected to a loop attachment part, for example of the distal side of the top layer and/or the distal side of the first adhesive layer and/or the distal side of another optional layer. Thereby, the base plate and/or the sensor assembly part may be laid out planar and the first part of the top layer and/or the first part of the electrode assembly may be bended and attached to the distal side of the base plate and/or the sensor assembly part, such as the distal side of the top layer, to form the loop element. The first loop end may be connected to the loop attachment part by gluing or welding or similar attachment measures.

Forming the coupling part by a loop element may provide an advantageous coupling between the monitor device and the base plate and/or the sensor assembly part. Also, the loop element may provide an easy and convenient way for forming the coupling part of the base plate and/or the sensor assembly part.

The first electrode assembly part may extend through an opening in the top layer to form at least part of the coupling part, for example such as to allow forming of the loop element. The first electrode assembly part and/or the first top layer part may be cut from the electrode assembly and/or the top layer, respectively, for example by a U-shaped cut, to allow forming at least part of the coupling part, such as to allow forming of the loop element. The first electrode assembly part and/or the first top layer part may be a part near an edge of the first electrode assembly part and the top layer, respectively, to allow forming at least part of the coupling part, for example to be bend around to form the loop element.

The plurality of terminals may be provided on an inside surface of the loop element, such as facing the conduit. Alternatively, the plurality of terminals may be provided on an outside surface of the loop element.

The plurality of terminals of the monitor device may be positioned to allow connection between the plurality of terminals of the monitor device and the plurality of terminals of the base plate and/or the sensor assembly part, when the monitor device is coupled to the base plate and/or the sensor assembly part. For example, the plurality of terminals of the monitor device may be provided inside the first slit. For example, the plurality of terminals of the monitor device may be provided on the first clip element. Alternatively, the plurality of terminals of the monitor device may be provided on the monitor device housing. For example, the appliance interface may be formed as part of the monitor device housing and the plurality of terminals may be provided on the monitor device housing.

The coupling part may comprise a rim and/or a base. The rim may extend distally, such as in an axial direction, for example in a distal direction. The axial direction may be perpendicular to the base plate plane. The rim may extend from the base. The rim may have a longitudinal axis. For example, the rim may extend along the longitudinal axis. The rim may be substantially symmetrical about the longitudinal axis. The longitudinal axis may be substantially perpendicular to the base plate plane.

The monitor device coupling part may comprise a wall portion. The wall portion may define a recess, for example configured to receive the coupling part of the base plate and/or the sensor assembly part.

The monitor device coupling part and the coupling part of the base plate and/or the sensor assembly part may be configured to cooperate, for example as bayonet or Luer connectors.

The coupling part may comprise an alignment member. The alignment member may be configured to guide the monitor device from the attachment position to the coupled position. The alignment member may comprise one or more coupling threads, for example including a coupling thread. The coupling threads may be on an inner surface of the rim.

Alternatively or additionally, the coupling threads may be on an outer surface of the rim.

The monitor device coupling part may comprise one or more tabs. The one or more tabs may be configured to engage the alignment member of the coupling part of the base plate and/or the sensor assembly part. The one or more tabs may extend from the wall portion into the recess. The one or more tabs may be substantially rectangular, cylindrical, rounded, or spherical.

The one or more tabs may be actuatable, for example the monitor device, such as the monitor device coupling part, may comprise, such as further comprise, an actuatable tab. One of the tabs, such as the actuatable tag may be configured to protrude off from the wall portion of the monitor device coupling part and retract into the wall portion when actuated. One of the tabs, such as the actuatable tab may be latched onto an actuation member. The actuation member may be actuatable between an unactuated position and an actuated position. The actuation member may comprise at least one of a slider, a button, or a switch. For example, the actuation member may comprise a slider. Alternatively or additionally, the actuation member may comprise a button. Alternatively or additionally, the actuation member may comprise a switch. The actuatable tab may be spring-loaded. The actuation member may be spring-loaded, for example towards the unactuated position.

The coupling threads may comprise one or more channels, for example defined by one or more protrusions. Each of the one or more channels may have an entry opening, such as an entry opening near a distal end of the rim. Each of the one or more channels may be configured to receive the monitor device, such as the monitor device coupling part, such as an element of the monitor device coupling part, such as a tab or one or more tabs of the monitor device coupling part. The one or more channels may extend toward the base of the coupling part. The one or more channels may extend circumferentially around the rim. For example, the one or more channels may extend toward the base of the coupling part circumferentially around the rim. Each of the one or more channels may have a stop near the base. The stop may be configured to define the coupled position for the monitor device.

The one or more channels may be segmented, for example the alignment member may comprise a segmented channel, for example comprising a plurality of segments, for example having different directions.

The segmented channel may comprise a first segment with a first direction, and a second segment with a second direction. The second direction may be different from the first direction, such as 90 degrees different or such as 45 degrees different. For example, the segmented channel may comprise one or more longitudinal segments and/or one or more transversal segments. The longitudinal segments of the segmented channel may extend substantially parallel to the longitudinal axis of the rim. The transversal segments of the segmented channel may extend substantially circumferentially about the longitudinal axis.

The one or more channels may have variable width, for example the alignment member may comprise one or more variable width channels including a variable width channel. One or more of the channels, such as the variable width channel may comprise a wide region and a narrow region. The wide region may be wider than the narrow region. The narrow region may be narrower than the wide region.

The one or more channels may have variable depth, for example the alignment member may comprise one or more variable depth channels including a variable depth channel. One or more of the channels, such as the variable depth channel may comprise a deep region and a shallow region. The deep region may be deeper than the shallow region. The shallow region may be shallower than the deep region.

The one or more channels may be pocketed, for example the alignment member may comprise one or more pocketed channels including a pocketed channel. One or more of the channels, such as the pocketed channel may comprise a guiding region, a pocketing region, and a pocketing element. The guiding region may be separated from the pocketing region by the pocketing element such that for a tab of the monitor device to enter the pocketing region from the guiding region of a pocketed channel, the tab may pass the pocketing element.

The pocketing element may comprise one or more protuberances and/or a separation wall. The one or more protuberances and/or separation wall may comprise compliant materials (for example plastics) configured to elastically deform, for example when engaged by tabs of the monitor device and/or when applied a pocketing force or de-pocketing force by the user, for example by rotation of the monitor device relative to the base plate and/or the sensor assembly part. The one or more protuberances may form a gap smaller than the tabs of the monitor device, for example such that the protuberances prevent the tabs from passing when not deformed by the pocketing force or the de-pocketing force. The separation wall may extend from a first surface, for example an upper surface, of the pocketed channel to a second surface, for example a lower surface, of the pocketed channel.

The base plate and/or the sensor assembly part and/or the monitor device, such as the coupling part and/or the monitor device coupling part, may comprise one or more magnetic elements. The one or more magnetic elements of the coupling part may be configured to be magnetically coupled to one or more magnetic elements of the monitor device. The one or more magnetic elements of the monitor device coupling part may be configured to be magnetically coupled to one or more magnetic elements of the base plate and/or the sensor assembly part. The one or more magnetic elements may be at least one of ferromagnetic, paramagnetic, diamagnetic, ferromagnetic, or antiferromagnetic. The one or more magnetic elements of the coupling part may be arranged symmetrically, such as symmetrically around the rim of the coupling part. The one or more magnetic elements if the monitor device coupling part may be arranged symmetrically, such as symmetrically about the recess.

The coupling between the base plate and/or the sensor assembly part and the monitor device may be configured to be waterproof. For example, to prevent and/or restrict water and/or other liquids to interfere with electrical elements and/or electrical coupling between the base plate and/or the sensor assembly part and the monitor device. For example, the base plate and/or the sensor assembly part, such as the coupling part of the base plate and/or the sensor assembly part, may comprise, such as further comprise, one or more waterproofing elements. Alternatively or additionally, the waterproofing element may be provided to the monitor device, such as monitor device coupling part. The one or more waterproofing element may be releasably attached to the base plate and/or the sensor assembly part and/or monitor device.

The one or more waterproofing elements may comprise a ring, such as a sealing ring. The ring may comprise rubber, polyurethane and/or silicone material. Alternatively or additionally, the one or more waterproofing elements may comprise a conical region of the coupling part and/or the monitor device coupling part. The conical region may be compliant, for example configured to elastically deform, such as when pressured by an opposing surface or edge to create a waterproofed seal. The conical region may comprise rubber, polyurethane and/or silicone, such as rubber, polyurethane and/or silicone material.

The monitor device, such as the monitor device housing, may be curved, for example to indicate to the user the correct way of orientating the monitor device on the base plate and/or the sensor assembly part. For example, the monitor device may be curved such that a concave side, such as the most concave side, of the monitor device is to be facing towards the stomal opening of the base plate and/or the sensor assembly part.

Also disclosed is a coupling cap for the base plate and/or the sensor assembly part, such as a coupling cap for protection of the coupling part and/or terminals of the monitor interface, for example when the base plate and/or the sensor assembly part is not coupled to a monitor device. The coupling cap may be configured to releasably and structurally couple the coupling cap to the base plate and/or the sensor assembly part, such as the coupling part of the base plate and/or the sensor assembly part.

The coupling cap may comprise a wall portion, for example defining a recess, for example configured to receive the coupling part of the base plate and/or the sensor assembly part. The coupling cap may comprise one or more tabs, for example configured to engage an alignment member of the coupling part of the base plate and/or the sensor assembly part.

The one or more tabs may extend from the wall portion into the recess. The one or more tabs may be substantially rectangular, cylindrical, rounded, or spherical.

Also disclosed is a method of coupling a monitor device for an ostomy system, such as the monitor device as disclosed above, to a base plate and/or a sensor assembly part for the ostomy system, such as the base plate and/or the sensor assembly part as disclosed above. The method may comprise positioning the monitor device coupling part in alignment with the coupling part of the base plate and/or the sensor assembly part and engaging the coupling part of the base plate and/or the sensor assembly part with the monitor device coupling part by applying the engagement force on the monitor device in the engagement direction relative to the base plate and/or the sensor assembly part. It will be understood that a method of decoupling is also disclosed as the monitor device may be decoupled from the base plate and/or the sensor assembly part, by similar but opposite methodology.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, for example via network 12. The server device 10 may be operated and/or controlled by the ostomy appliance manufacturer and/or a service centre.

Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma centre point. The size and/or shape of the stomal opening 18 is typically adjusted by the user or nurse before application of the ostomy appliance to accommodate the user's stoma.

Figure 2:
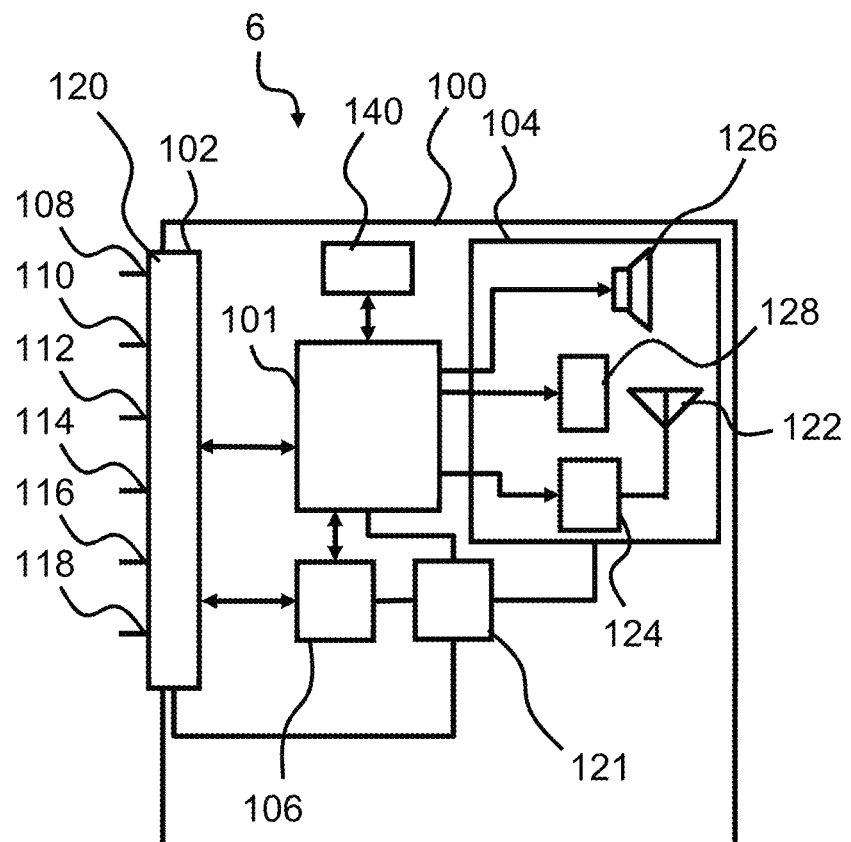
FIG. 2 illustrates an exemplary monitor device of the ostomy system.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic illustration of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, for example ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a monitor device coupling part 120 for forming a mechanical connection, such as a releasable coupling between the monitor device and the base plate. The monitor device coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, for example terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, for example all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
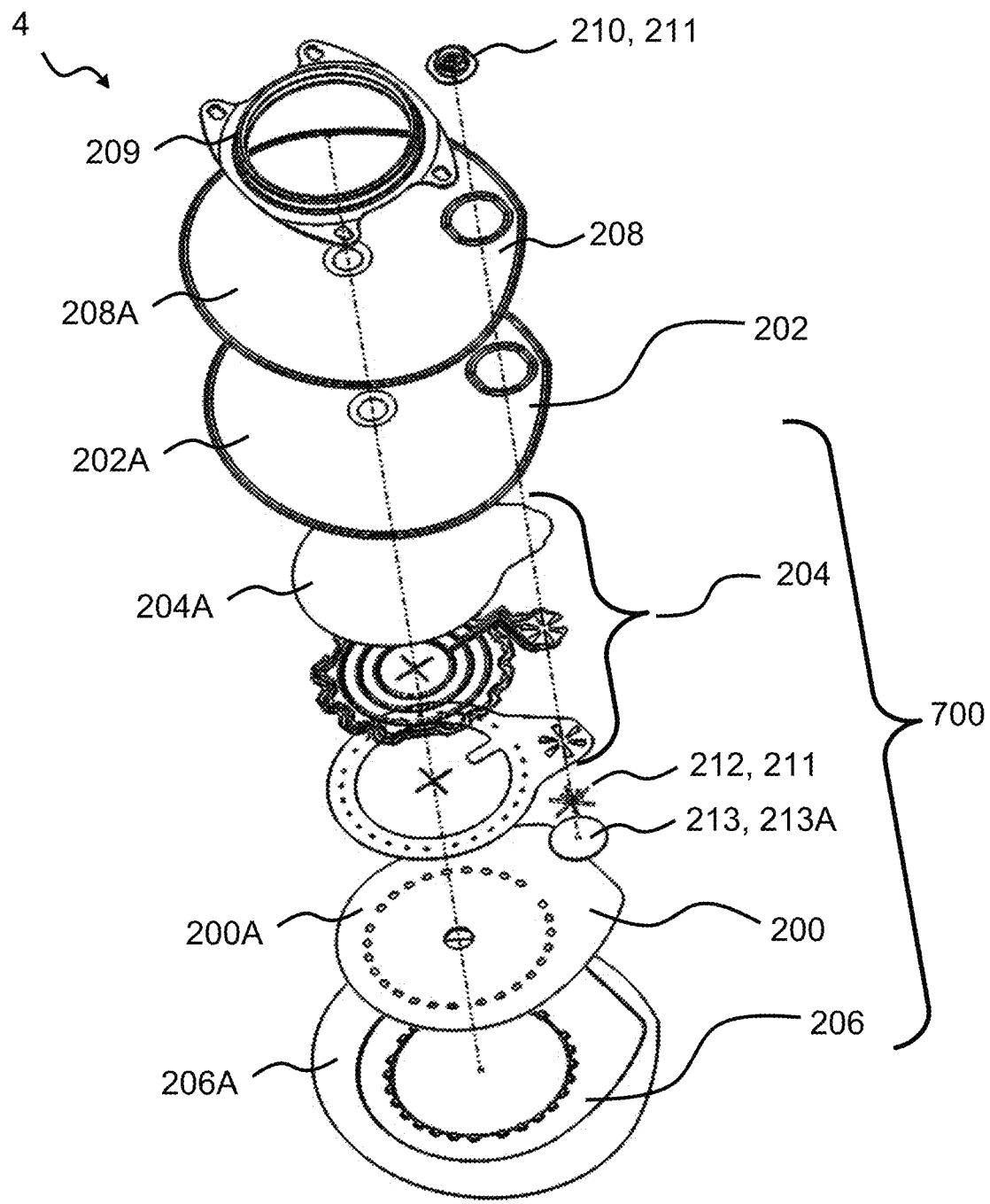
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device (for example a monitor device coupling part) for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, for example comprising one or more of the components as described, such as to provide a base plate like the base plate 4 as described. For example, a sensor assembly part 700 may be provided, for example comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
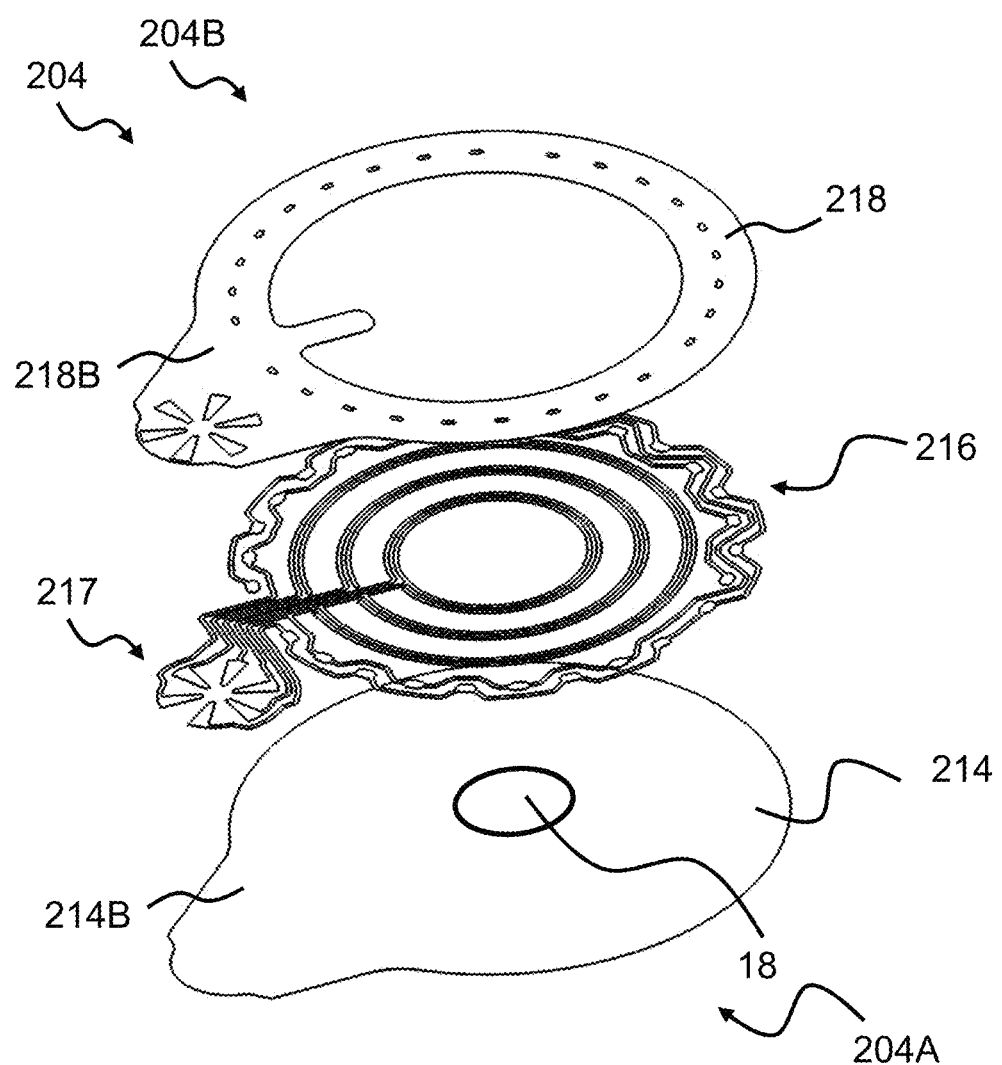
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly comprises a support layer 214 with proximal surface 214B and electrodes 216 including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are provided, such as formed, on a proximal side 214B of the support layer 214, for example the electrodes 216 may be positioned on the proximal side 214B of the support layer. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
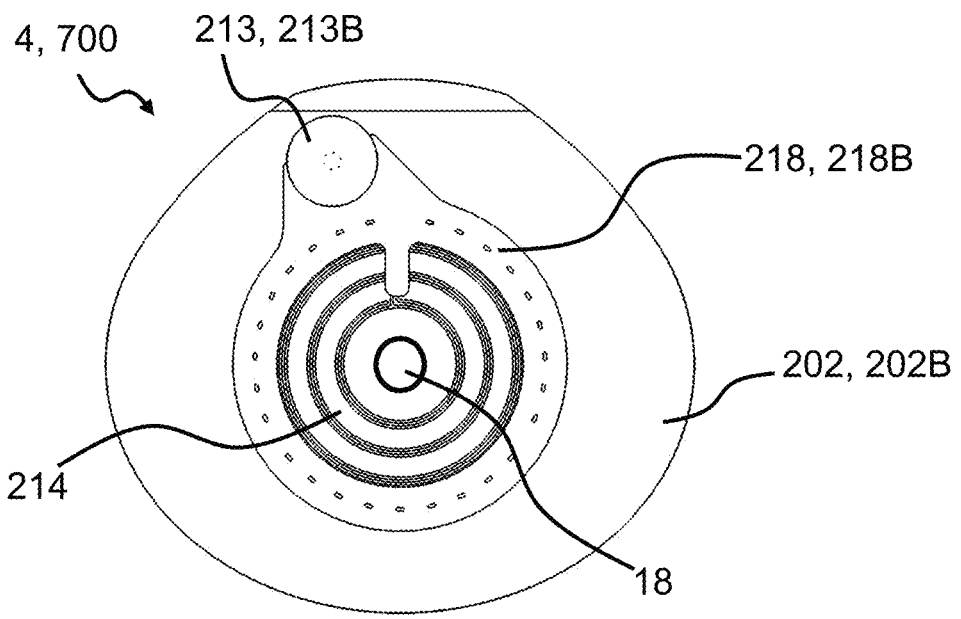
FIG. 5 is a proximal view of parts of a base plate and/or sensor assembly part.

FIG. 5 is a proximal view of proximal surfaces of parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 and/or the sensor assembly part 700 when seen in the axial direction and protects the first adhesive layer from mechanical stress from the terminal elements of the base plate and/or the sensor assembly part.

Figure 6:
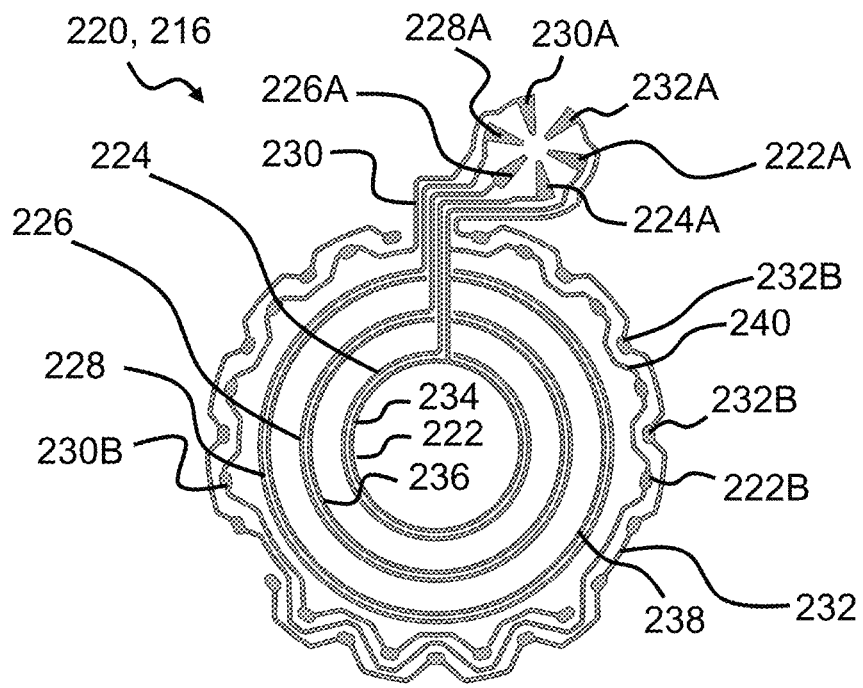
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B

Figure 7:
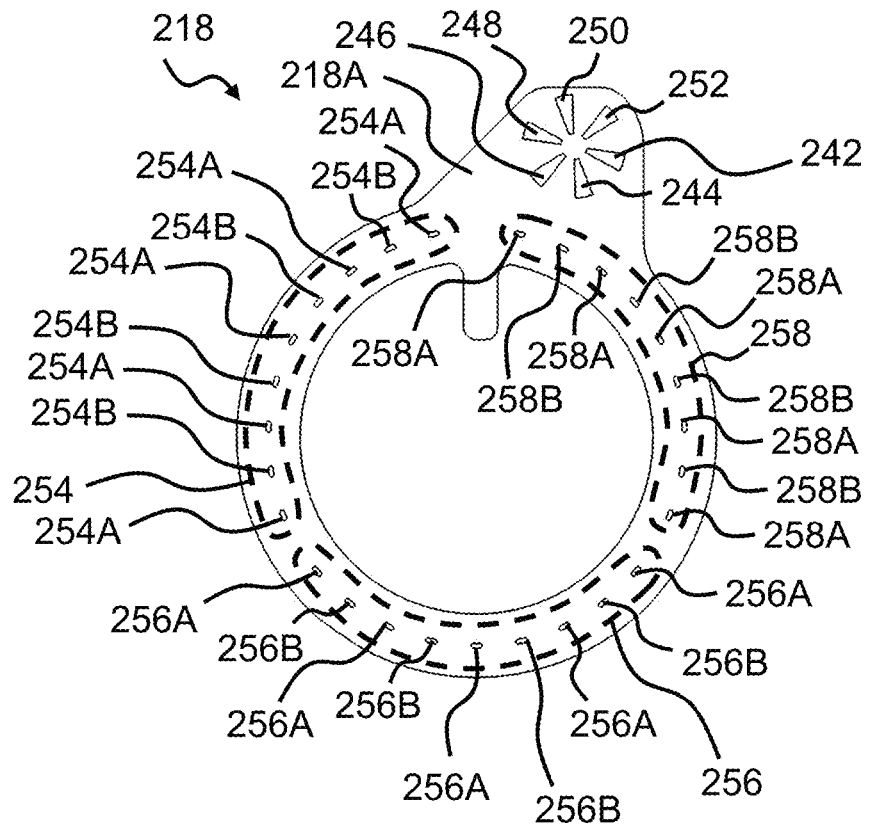
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
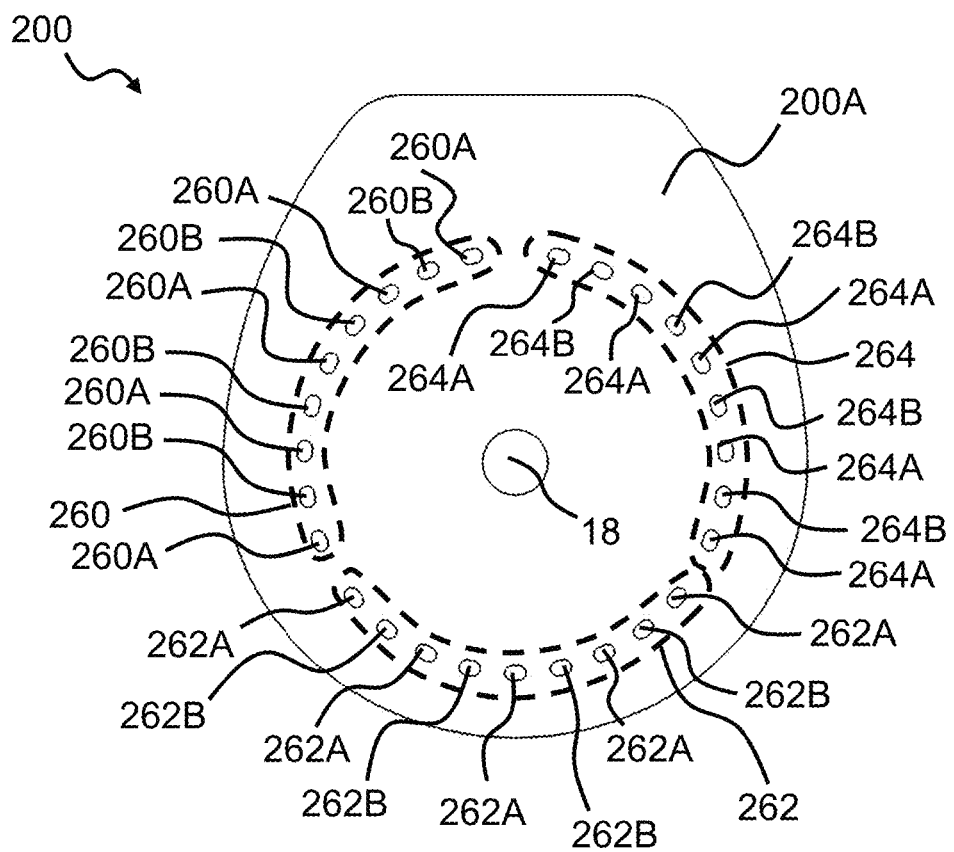
FIG. 8 is a distal view of an exemplary first adhesive layer.
Figure 9:
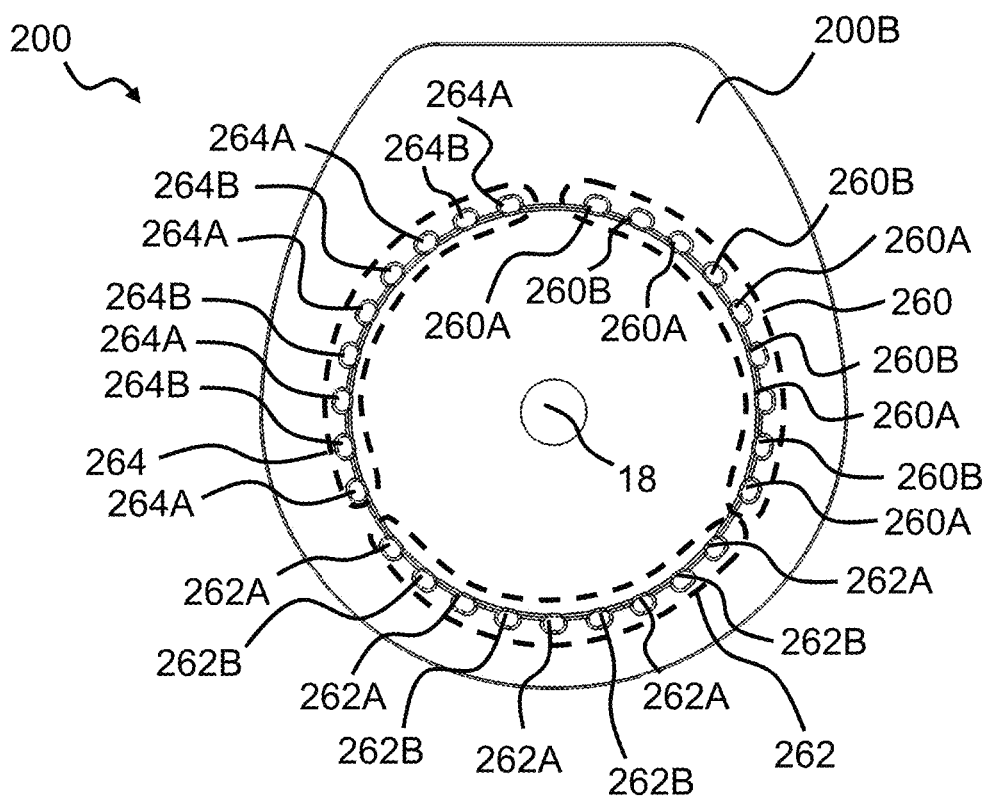
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
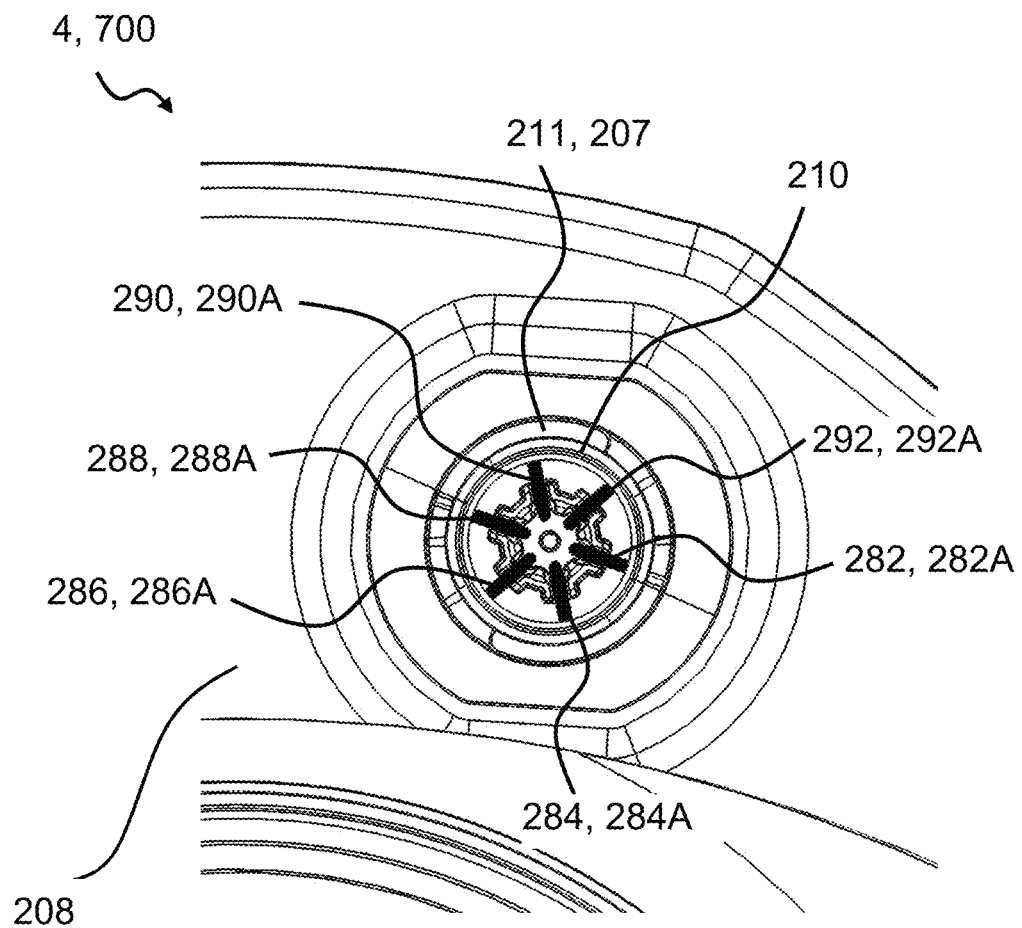
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface 207. The monitor interface 207 comprises the first connector 211. The first connector 211 comprises coupling part 210 configured to releasably couple the monitor device to the base plate and/or the sensor assembly part and thus forming a releasable coupling. The first connector 211 of the monitor interface 207 comprises a plurality of terminals formed by respective terminal elements for forming respective electrical connections with respective terminals of the monitor device.

The plurality of terminals of the first connector 211 of the monitor interface 207 comprises a ground terminal element 282 forming a ground terminal 282A, a first terminal element 284 forming a first terminal 284A, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11A:
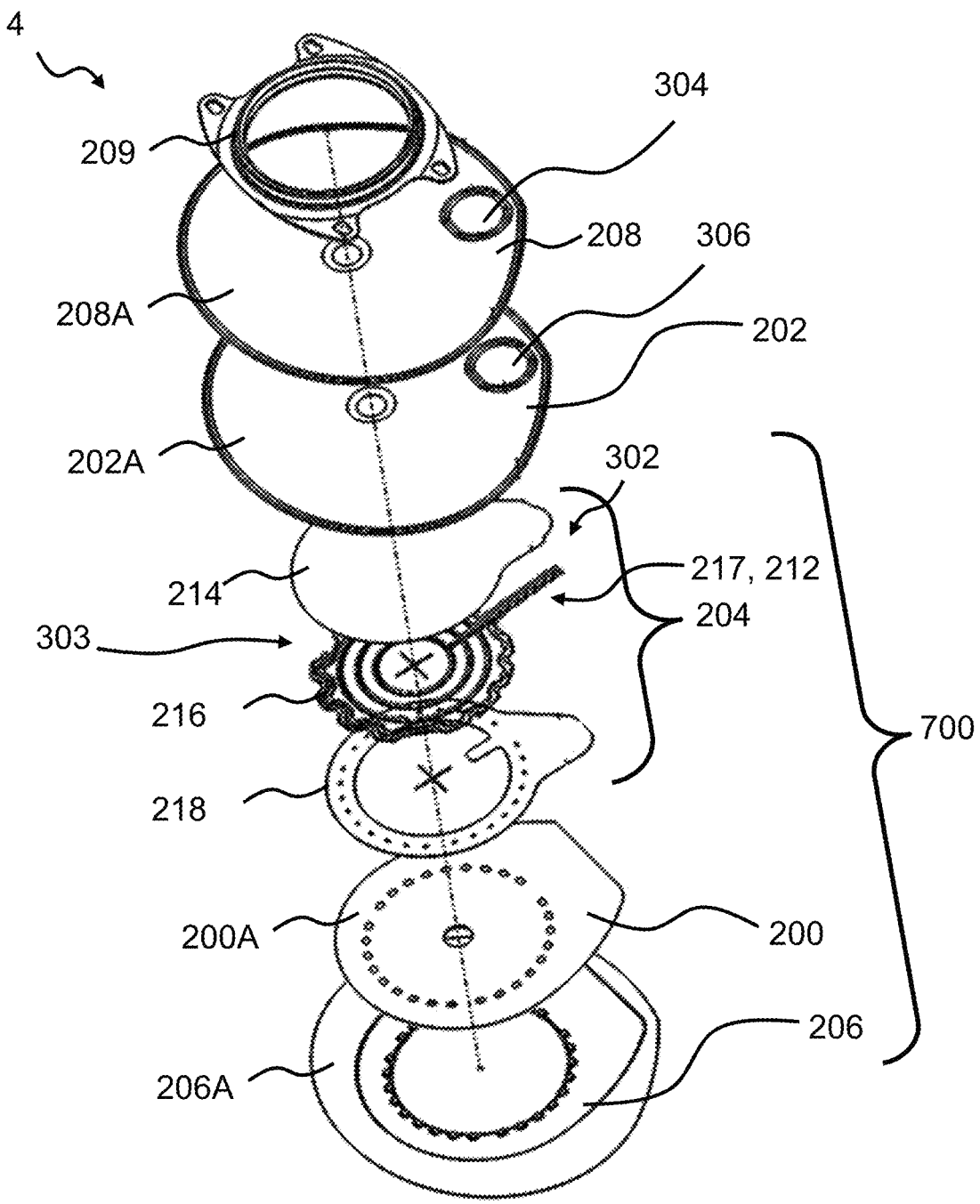
FIG. 11a illustrates an exploded view of an exemplary base plate.

FIG. 11a illustrates an exploded view of an exemplary base plate 4 of an ostomy appliance. The base plate 4 comprises a first adhesive layer 200. The base plate 4 optionally comprises a second adhesive layer 202, also denoted rim adhesive layer. The base plate 4 comprises a plurality of electrodes 216 arranged in an electrode assembly 204. The electrode assembly 204 is arranged between the first adhesive layer 200 and the second adhesive layer 202. The electrode assembly 204 optionally comprises a support layer 214. The electrodes may be formed on a proximal side of the support layer 214, such as by printing of conductive ink. The electrode assembly 204 optionally comprises a masking element 218, for example covering or overlapping with parts of the electrodes 216 when seen in the axial direction, for example from a proximal side of the electrodes 216. The electrode assembly has a first part 302 comprising connection parts 217 of the plurality of electrodes 216. The electrode assembly has a second part 303. The base plate 4 comprises a release liner 206. The base plate 4 comprises a top layer 208.

The base plate 4 optionally comprises a coupling ring 209 for coupling an ostomy pouch to the base plate 4. Alternatively, for example for a one-part ostomy appliance, an ostomy pouch may be directly fastened to the base plate 4.

The base plate 4 comprises a monitor interface configured for connecting, such as mechanically and/or electronically connecting, the base plate to a monitor device. The monitor interface comprises a plurality of terminals 212 configured to form electrical connections with respective terminals of the monitor device. For example, as illustrated, Alternatively, for example as shown in FIG. 3, terminal elements may be provided to form the plurality of terminals.

The top layer 208 comprises a top layer opening 304. The second adhesive layer 202 comprises a second adhesive layer opening 306. The top layer opening 304 and the second adhesive layer opening 306 are configured to allow for connection between the plurality of electrodes 216 of the electrode assembly 204 and terminals of a monitor device being coupled to the base plate 4. For example, the first part 302 of the electrode assembly 216 may extend through the top layer opening 304 and the second adhesive layer opening 306.

Figure 11B:
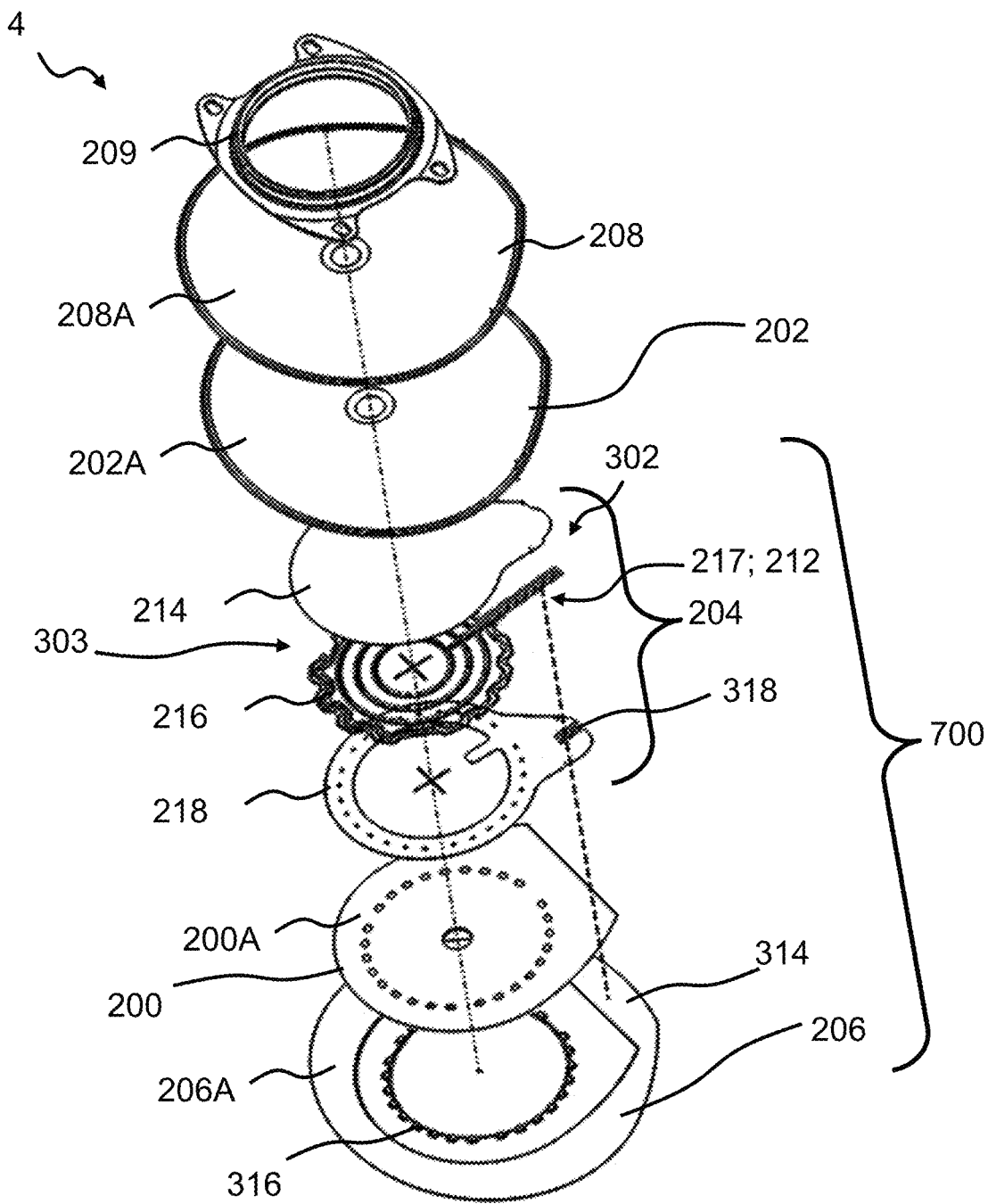
FIG. 11b illustrates an exploded view of an exemplary base plate.

FIG. 11b illustrates an exploded view of an exemplary base plate 4 of an ostomy appliance. The base plate 4 comprises a first adhesive layer 200. The base plate 4 optionally comprises a second adhesive layer 202, also denoted rim adhesive layer. The base plate 4 comprises a plurality of electrodes 216 arranged in an electrode assembly 204. The electrode assembly 204 is arranged between the first adhesive layer 200 and the second adhesive layer 202. The electrode assembly 204 optionally comprises a support layer 214. The electrodes 216 may be formed on a proximal side of the support layer 214, such as by printing of conductive ink on the proximal side of the support layer 214. The electrode assembly 204 optionally comprises a masking element 218, for example covering or overlapping with parts of the electrodes 216 when seen in the axial direction, for example from a proximal side of the electrodes 216. The electrode assembly 204 has a first part 302 comprising connection parts 217 of the plurality of electrodes 216. The electrode assembly 204 has a second part 303. The second part 303 comprises sensing parts of the plurality of electrodes 216. The base plate 4 comprises a release liner 206. The base plate 4 comprises a top layer 208. The base plate 4 optionally comprises a coupling ring 209 for coupling an ostomy pouch to the base plate 4. Alternatively, for example for a one-part ostomy appliance, an ostomy pouch may be directly fastened to the base plate 4.

The base plate 4 comprises a monitor interface configured for connecting, such as mechanically and/or electronically connecting, the base plate 4 to a monitor device. The monitor interface comprises a plurality of terminals 212 configured to form electrical connections with respective terminals of the monitor device. For example, as illustrated, Alternatively, for example as shown in FIG. 3, terminal elements may be provided to form the plurality of terminals 212.

As illustrated by the dashed line, the layers are aligned such that the first adhesive layer 200 is not covering a primary side, such as a distal side, of the first part 302 of the electrode assembly 204.

The release liner 206 comprises a first elevated part 314 and a plurality of protrusions 316. The first adhesive layer 200 may be provided by scraping a layer of a first composition, such as a first adhesive composition, onto the release liner 206. The increased height of the protrusions 316 and elevated part(s) 314 minimizes the distance between the scraping apparatus and the release liner 206 such that the first composition is not deposited in these areas. Thereby, the protrusions 316 accounts for the sensor point openings (for example sensor point openings 260, 262, 264 of FIG. 8) of the first adhesive layer 200, and the first elevated part 314 accounts for the first part 302, such as the primary side of the first part 302, of the electrode assembly 204 not being covered by the first adhesive layer 200.

Furthermore, the first adhesive layer 200 may typically show viscous properties, and the release liner 206 having the protrusions 316 and the first elevated part 314 provides that shape of the first adhesive layer 200, including the sensor point openings, is maintained while the release liner 206 is maintained.

The optional masking element 218 may be provided to insulate the plurality of electrodes 216, or parts of the plurality of electrodes 216. The masking element 218 has a plurality of terminal openings 318 to allow connection to the connecting parts 217 of the plurality of electrodes 216, for example from a proximal side of the electrode assembly 204.

As described in respect to FIG. 3, similarly, some parts of the illustrated base plate 4 of FIGS. 11a and 11b, may be provided as a separate assembly, such as a sensor assembly part 700 to be applied to an existing base plate, for example comprising one or more of the components as described, such as to provide a base plate like the base plate 4 as described.

Figure 12:
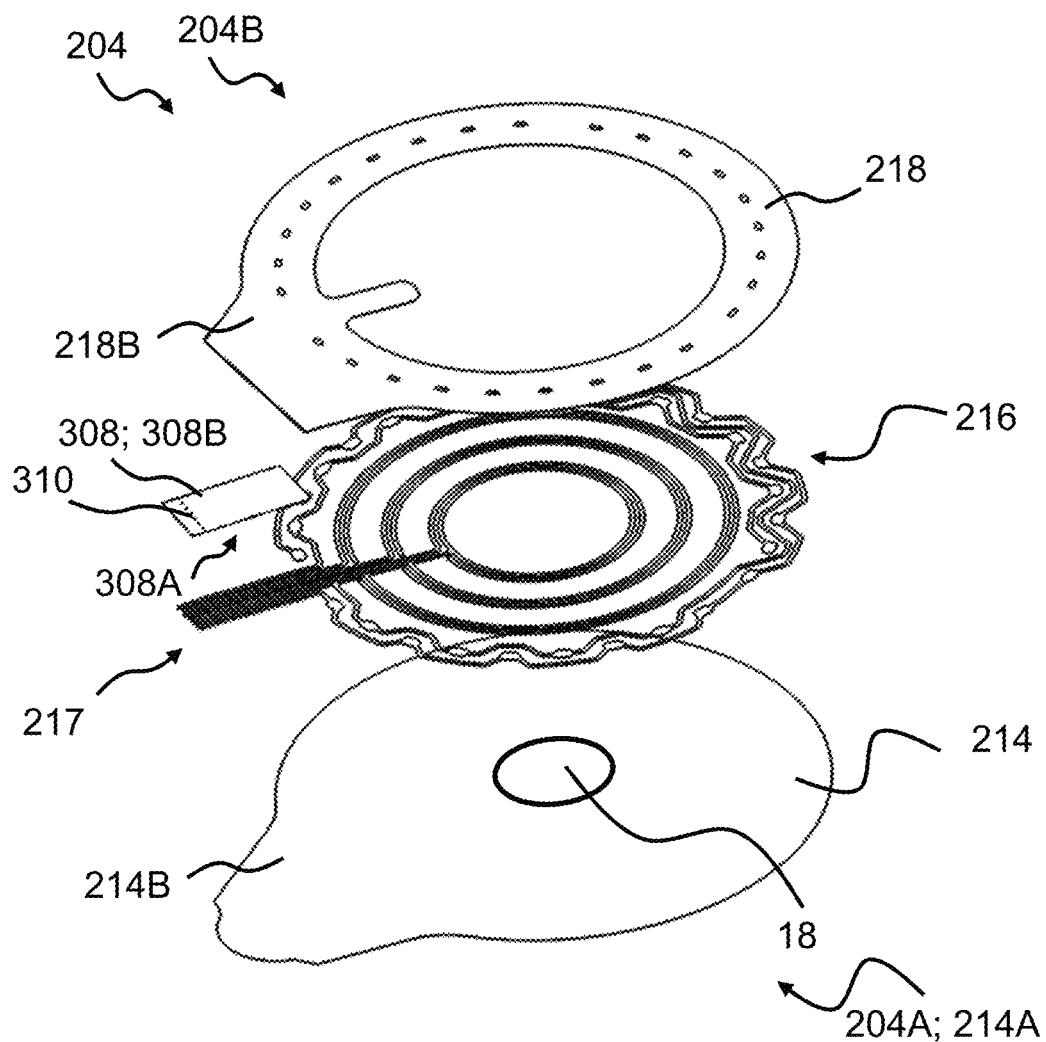
FIG. 12 illustrates an exploded view of an exemplary electrode assembly.

FIG. 12 illustrates an exploded view of an exemplary electrode assembly 204 of a base plate, such as the base plate 4 of FIG. 11a or FIG. 11b. The electrode assembly 204 has a distal side 204A and a proximal side 204B. The electrode assembly 204 comprises a support layer 214 with a proximal side 214B and a distal side 214A. The electrode assembly 204 comprises a plurality of electrodes 216. Each electrode of the plurality of electrodes 216 has a respective connection part 217 for connecting the electrodes 216 to respective terminal elements of the monitor interface. The electrodes 216 are provided, such as formed, on the proximal side 214B of the support layer 214, for example the electrodes 216 may be positioned on the proximal side 214B of the support layer 214. Further, electrode assembly 204 optionally comprises a masking element 218 with proximal side 218B and configured to insulate electrode parts of electrodes 216 from the first adhesive layer 200 of the base plate 4 (see FIG. 11a or FIG. 11b). The masking element 218 covers or overlap with parts of the electrodes 216 when seen in the axial direction, for example from the proximal side 204B. The masking element 218 may be configured not to cover or overlap the connecting parts 217 of the plurality of electrodes.

In some exemplary electrode assembly 204, such as the electrode assembly 204 of FIG. 12, the electrode assembly 204 comprises a reinforcement element 308. The reinforcement element 308 may be positioned proximal to the electrode assembly 216, such as proximal to the plurality of electrodes 216, such as proximal to the plurality of connection parts 217 of the plurality of electrodes 216. The reinforcement element 308 may form at least part of a first part of the electrode assembly 204. The reinforcement element 308 may be provided with openings 310 to provide conductive pathways between sides of the reinforcement element 308, such as between a proximal side 308B and a distal side 308A of the reinforcement element 308.

Figure 13:
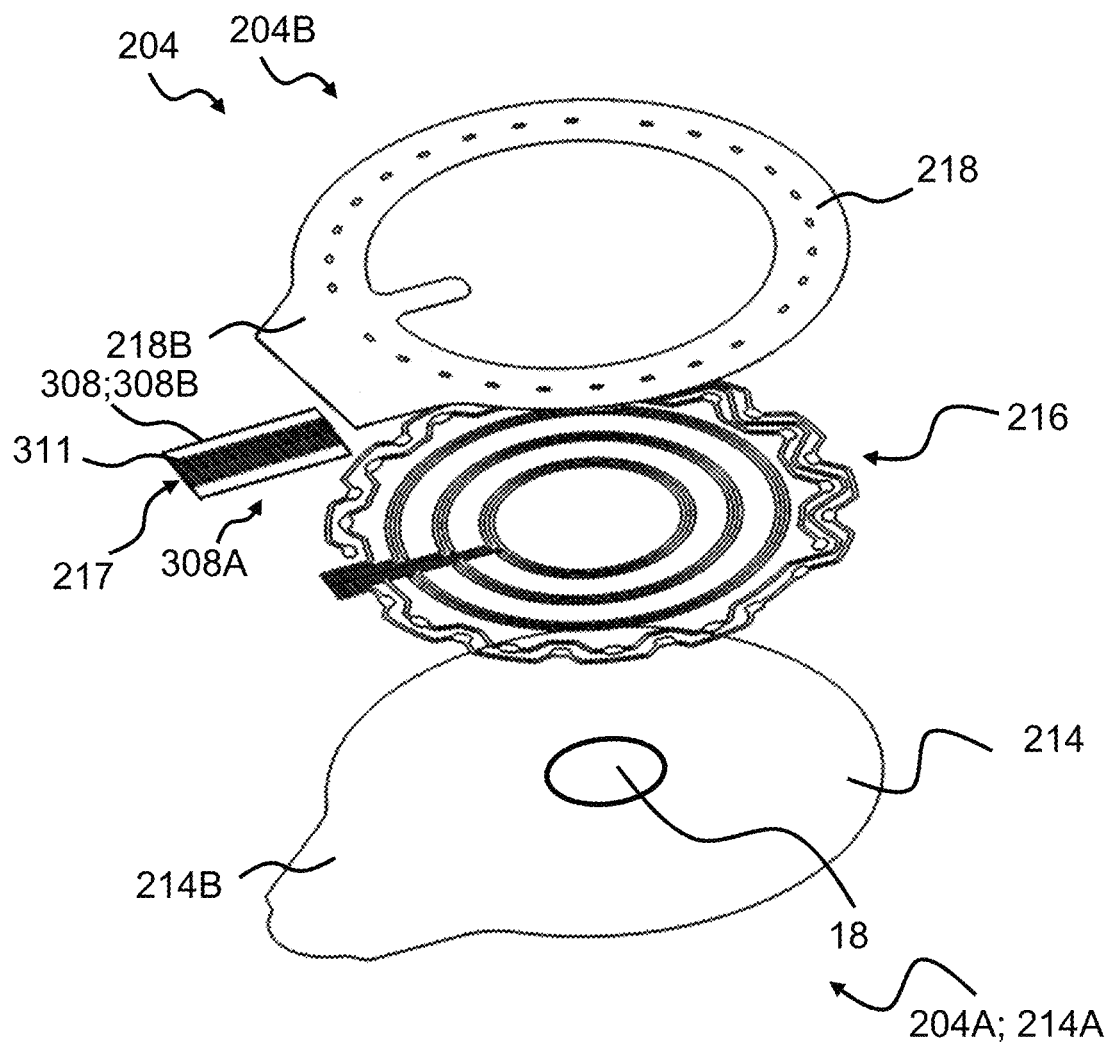
FIG. 13 illustrates an exploded view of an exemplary electrode assembly.

FIG. 13 shows an alternative to FIG. 12, wherein the reinforcement element 308 comprises a plurality of conductive paths 311. For example, the reinforcement element 308 may be a flex circuit. The plurality of conductive paths 311 may be connected to the plurality of electrodes 216. The plurality of conducive paths 311 thereby may form the connection parts 217 of the plurality of electrodes 216. The plurality of conductive paths 311 may provide conductive pathways between the proximal side 308B and the distal side 308A of the reinforcement element 308.

Figure 14:
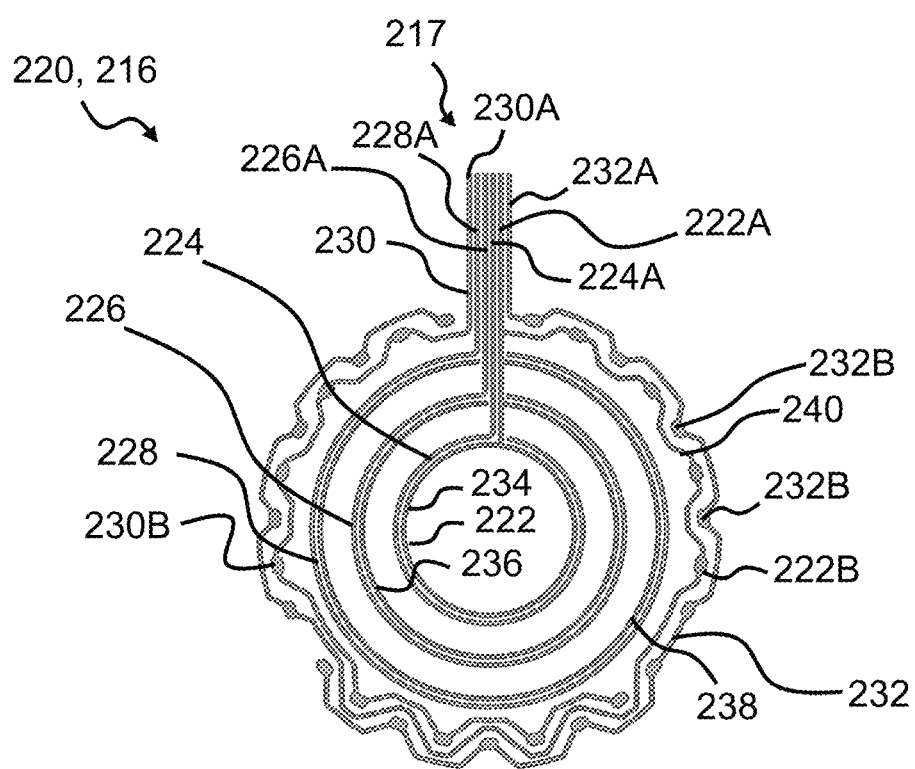
FIG. 14 shows an exemplary electrode configuration.

FIG. 14 shows an exemplary electrode configuration 220 of the plurality of electrodes 216, like the electrode configuration 220 as shown in FIG. 6, with the difference that the connection parts 217, such as the ground connection part 222A, the first connection part 224A, the second connection part 226A, the third connection part 228A, the fourth connection part 230A and/or the fifth connection part 232A, are straight connector parts.

Figure 15:
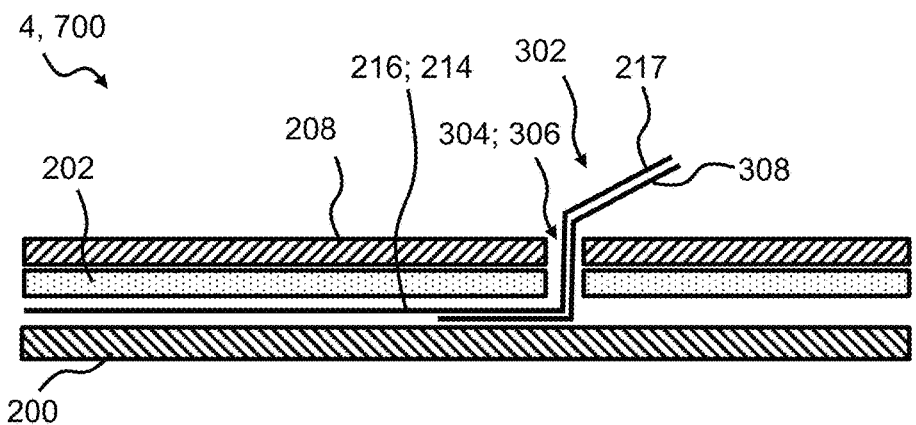
FIG. 15 shows a schematic representation of part of a base plate and a sensor assembly part.

FIG. 15, shows a sectional schematic representation of part of a base plate 4 and the sensor assembly part 700. The base plate 4 and the sensor assembly part 700 comprises a first adhesive layer 200, an optional second adhesive layer 202, and a top layer 208. An electrode assembly comprising a plurality of electrodes 216 is arranged between the first adhesive layer 200 and the top layer 208, such as between the first adhesive layer 200 and the second adhesive layer 202. For example, a second part of the electrode assembly is arranged between the first adhesive layer and the second adhesive layer 202 and the top layer 208. The electrode assembly further comprises an optional reinforcement element 308.

The top layer 208 and the second adhesive layer 202 comprise openings 304; 306. The top layer 208 comprises a top layer opening 304. The second adhesive layer 202 comprises a second adhesive layer opening 306. A first part 302 of the electrode assembly extends through the top layer opening 304 and the second adhesive layer opening 306. The first part 302 includes the connection parts of the plurality of electrodes and the reinforcement element 308. The first part 302 may include the support layer 214 or a part of the support layer. Connection to the connection parts 217 of the plurality of electrodes may be provided through the reinforcement element 308 and through the support layer 214.

FIG. 16, shows a sectional schematic representation of part of a base plate 4 and the sensor assembly part 700 as shown in FIG. 15, wherein the base plate 4 and the sensor assembly part 700 comprises a coupling part 210. The coupling part 210 is configured for forming a mechanical connection between the monitor device and the base plate 4 and the sensor assembly part 700. The first part 302 of the electrode assembly is extending into the coupling part 210, for example to allow the monitor device, such as terminals of the monitor device to connect to the electrodes 216 of the base plate 4 and the sensor assembly part 700. The base plate plane P is shown in the figure as a parallel plane to the top layer 208, and likewise, parallel with the base 504 of the coupling part 210.

In the example shown, the coupling part 210 is attached to the top layer 208. However, in an alternative example, the coupling part 210 is attached to the electrode assembly, in such situation the coupling part 210 may extend through the top layer opening 304 and the second adhesive layer opening 306.

Figure 17:
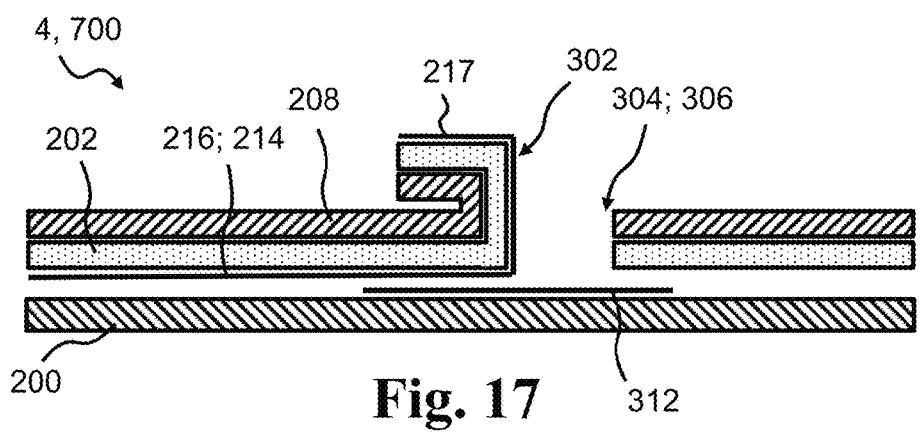
FIG. 17 shows a schematic representation of part of a base plate and a sensor assembly part.

FIG. 17, shows a sectional schematic representation of part of a base plate 4 and the sensor assembly part 700. The base plate 4 and the sensor assembly part 700 comprises a first adhesive layer 200, an optional second adhesive layer 202, and a top layer 208. An electrode assembly comprising a plurality of electrodes 216 is arranged between the first adhesive layer 200 and the top layer 208, such as between the first adhesive layer 200 and the second adhesive layer 202. For example, a second part of the electrode assembly is arranged between the first adhesive layer and the second adhesive layer 202 and/or the top layer 208.

The top layer 208 comprises a top layer opening 304. The second adhesive layer 202 comprises a second adhesive layer opening 306. The top layer opening 304 and the second adhesive layer opening 306 is provided by a U-shaped cut. A first part 302 of the electrode assembly is turned over, together with a part of the top layer 208 and the second adhesive layer 202 inside the U-shaped cut, to expose the connection parts 217 of the plurality of electrodes 216 on a distal side of the base plate 4 and the sensor assembly part 700. The first part 302 includes the connection parts 217 of the plurality of electrodes and extends through the top layer opening 304 and the second adhesive layer opening 306. The monitor device may thereby connect to the plurality of connection parts 217.

Although not shown in FIG. 17, the electrode assembly may further comprise an optional reinforcement element 308, for example as illustrated in FIGS. 15 and 16 and/or the base plate 4 and the sensor assembly part 700 may be provided with a coupling part 210, for example as shown in FIG. 16.

The base plate 4 and the sensor assembly part 700 comprises a back element 312. The back element 312 is provided between the first adhesive layer 200 and the electrode assembly and/or the plurality of electrodes 216 of the electrode assembly, such as between the first adhesive layer 200 and the first part 302 of the electrode assembly. The back element 312 may facilitate that the first part 302 of the electrode assembly is not adhering to the first adhesive layer, such as to allow the first part 302 of the electrode assembly to be turned. A back element 312 may similarly be applied to the exemplary base plates and/or the sensor assembly part 700 as described in relation to FIGS. 15 and/or 16.

Figure 18:
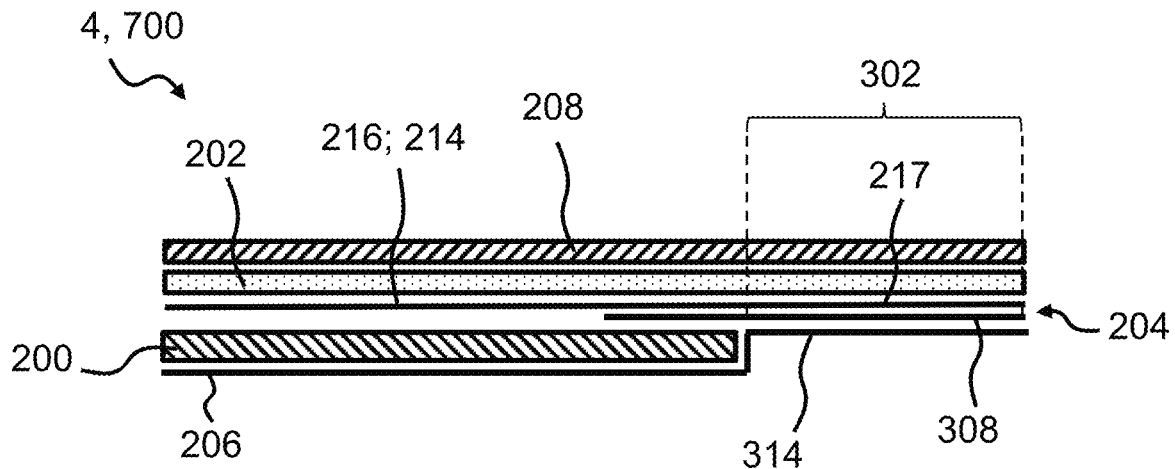
FIG. 18 shows a schematic representation of part of a base plate and a sensor assembly part.

FIG. 18, shows a sectional schematic representation of part of a base plate 4 and the sensor assembly part 700. The base plate 4 and the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer 200 and the second adhesive layer 202 and/or the top layer 208. The electrode assembly 204 further comprises an optional reinforcement element 308 and an optional release liner 206.

The first adhesive layer 200 is provided such that it does not cover a primary side of a first part 302 of the electrode assembly 204. For example, the release liner 206 comprises a first elevated part 314 such as to facilitate the formation of the first adhesive layer 202 to not cover the primary side of the first part 302 of the electrode assembly 204. The primary side of the first part 302 may be a proximal side of the first part 302. The first part 302 includes the connection parts of the plurality of electrodes 216 and the reinforcement element 308 or part of the reinforcement element 308. The first part 302 may include part of the support layer 214.

Figure 19:
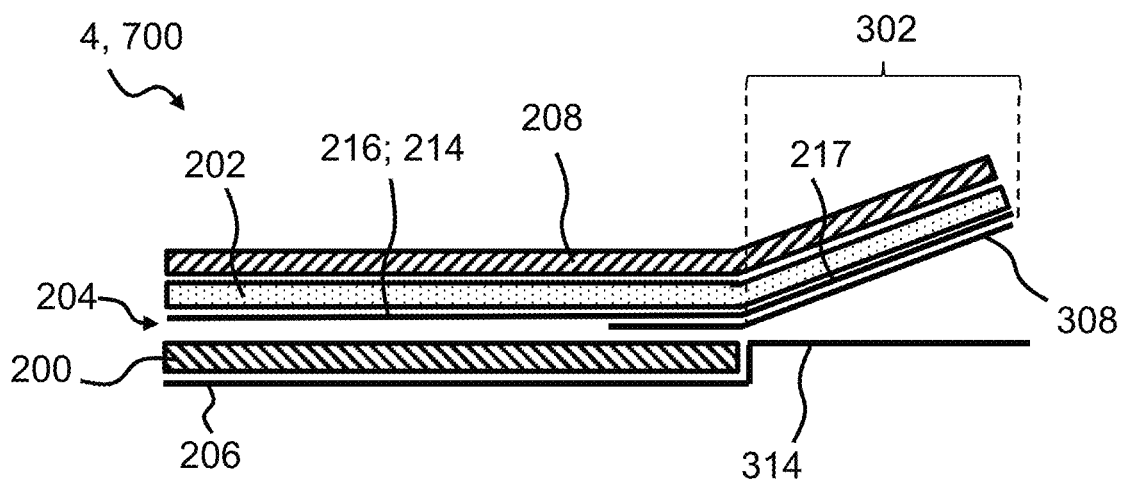
FIG. 19 shows a schematic representation of part of a base plate and a sensor assembly part.

FIG. 19, shows a sectional schematic representation of part of a base plate 4 and the sensor assembly part 700 as shown in FIG. 18, further illustrating that the connection parts 217 may be accessible, for example by slightly bending the first part 302 of the electrode assembly 204 in a distal direction. Alternatively, the release liner 206 may be removed so the first part 302 of the electrode assembly 204 is accessible from a proximal side.

Because the first adhesive layer 200 is not covering the first part 302 of the electrode assembly 204, the first part 302 is not adhered to the release liner or any other proximally positioned layers. Therefore, the connection parts 217 may be accessible, for example for connection with a monitor device. Connection to the connection parts 217 of the plurality of electrodes 216 may be provided through the reinforcement element 308, or the connection parts 217 may be formed by conductive paths of the reinforcement element 308.

Figure 20:
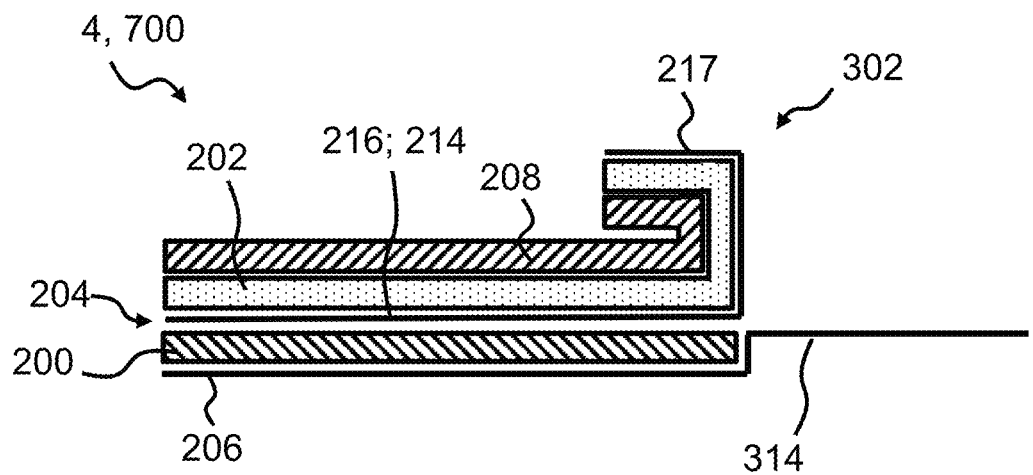
FIG. 20 shows a schematic representation of part of a base plate and a sensor assembly part.

FIG. 20, shows a sectional schematic representation of part of a base plate 4 and the sensor assembly part 700. The base plate 4 and the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer and the second adhesive layer 202/the top layer 208. Although not illustrated, the electrode assembly 204 may comprise a reinforcement element 308, for example as illustrated in FIGS. 18 and 19. Thus, the base plate 4 and the sensor assembly part 700 of FIG. 20 may correspond to the base plate 4 and the sensor assembly part 700 of FIGS. 18 and 19.

The first part 302 of the electrode assembly 204, together with the top layer 208 and the optional second adhesive layer, has been turned over to expose the connection parts 217 of the plurality of electrodes 216 on a distal side of the base plate 4. Thus, the primary side of the first part 302 initially being a proximal side (as shown in FIG. 18) is, after the first part 302 has been turned, facing distally.

Figure 21:
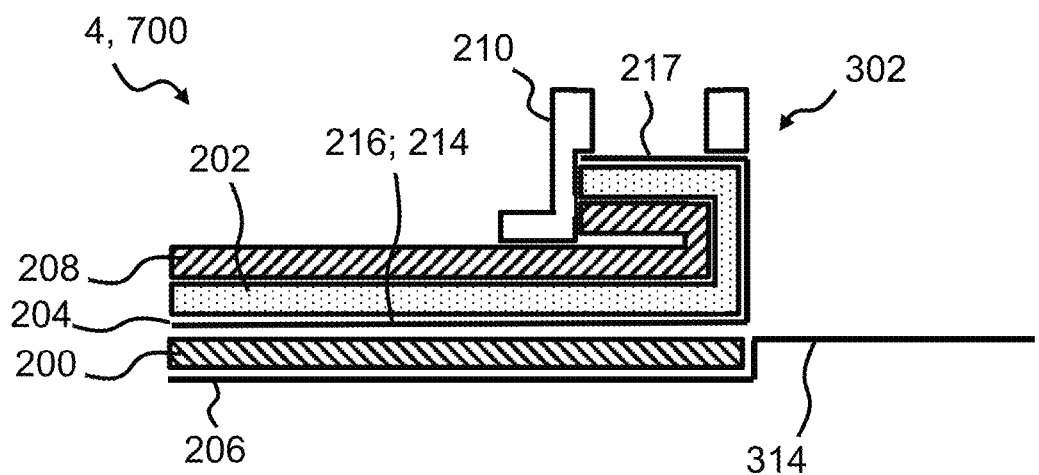
FIG. 21 shows a schematic representation of part of a base plate and a sensor assembly part.

FIG. 21, shows a sectional schematic representation of part of a base plate 4 and the sensor assembly part 700 as shown in FIG. 20, wherein the base plate 4 and the sensor assembly part 700 comprises a coupling part 210. The coupling part 210 is configured for forming a mechanical connection between the monitor device and the base plate 4 and the sensor assembly part 700. The first part 302 of the electrode assembly 204 is extending into the coupling part 210, for example to allow the monitor device, such as terminals of the monitor device to connect to the electrodes 216 of the base plate 4 and the sensor assembly part 700. The coupling part 210 is positioned to cover the connection parts 217 of the plurality of electrodes 216. The coupling part 210 may be attached to the top layer 208 and/or the coupling part 210 may be attached to the electrode assembly 204.

Figure 22:
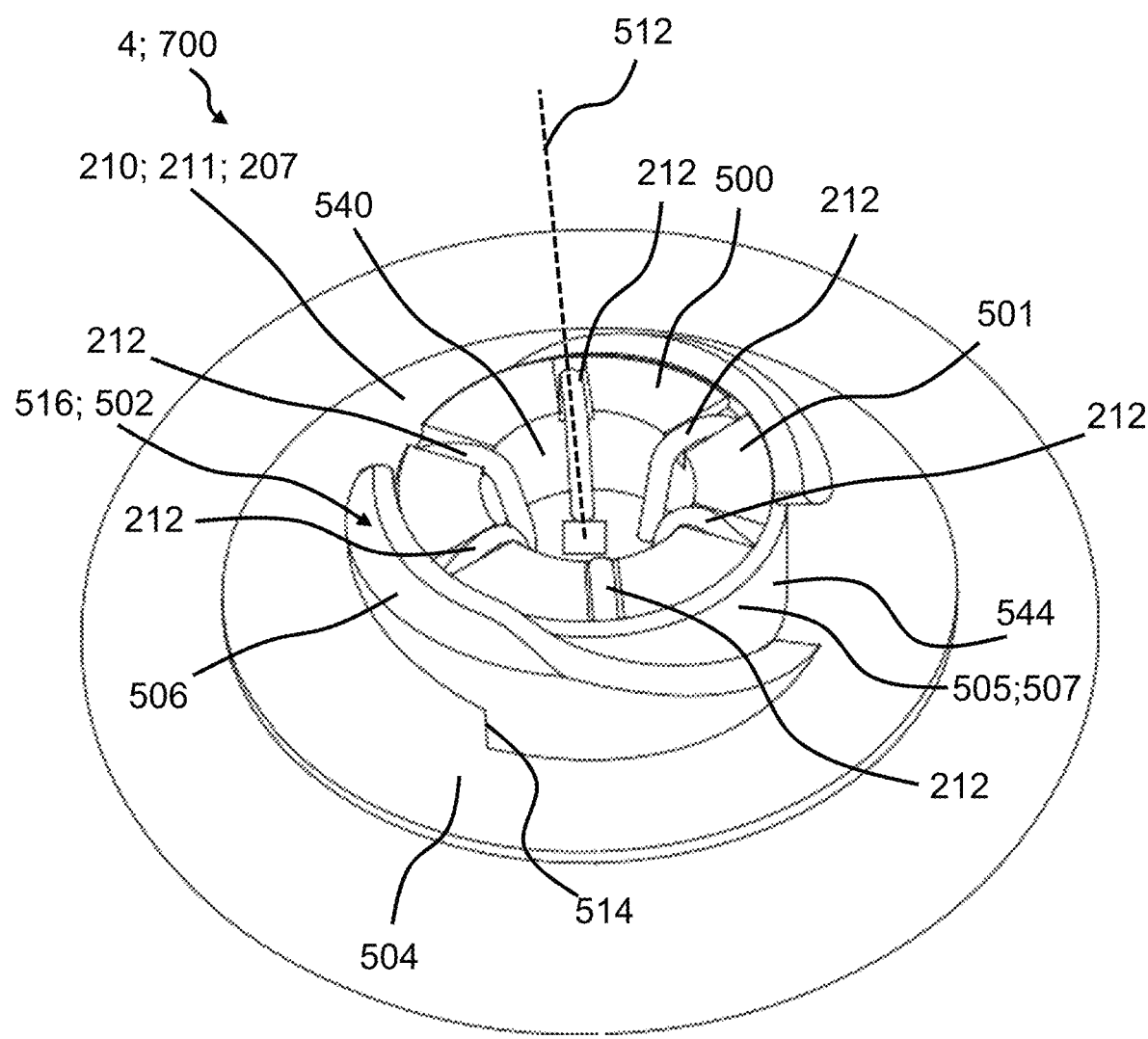
FIG. 22 is a schematic representation of a part of a base plate and a sensor assembly part,
FIG. 23 schematically illustrates a monitor device.

FIG. 22 is a schematic representation of a part of a base plate 4 and a sensor assembly part 700 including a first connector 211, as part of the monitor interface 207. As shown, the first connector 211 includes the coupling part 210 and the plurality of terminals 212. The illustrated example of the coupling part 210 includes a rim 500 and a base 504. The rim 500 extends distally from the base plate 4 along a longitudinal axis 512. The longitudinal axis 512 may be substantially perpendicular to the base 504 and/or the base plate 4, such as a first adhesive layer and/or a top layer of the base plate 4. For example, the longitudinal axis 512 may be substantially perpendicular to a base plate plane, for example extended by the base plate and/or one or more layers of the base plate 4, such as the first adhesive layer and/or the top layer. The base 504 may be substantially parallel to the base plate 4, such as a first adhesive layer and/or a top layer of the base plate 4. For example, the base 504 may be substantially parallel the base plate plane. The coupling part 210 further includes an alignment member 516. The alignment member 516 may, as illustrated, comprise coupling threads 502. The alignment member 516, such as the coupling threads 502 of the alignment member 516, may be on an inner surface 540 of the rim 500 or on an outer surface 544 of the rim 500, as illustrated. The coupling threads 502 include one or more slots or channels 505 (two are shown in the illustrated example) defined by projections or protrusions 506 from the rim 500. Each channel has an entry opening 507 adjacent the top or distal end 501 of the rim 500 and extends proximally toward the base 504 as it wraps in a circumferential direction around the rim 500. Each channel 505 may have a stop 514, for example near the base 504. Similar to the alignment member 516 of the base plate 4, a monitor device 6, such as the monitor device 6 of FIG. 1 and/or FIG. 23 may also comprise one or more alignment members configured to couple the monitor device to the base plate.

Figure 23:
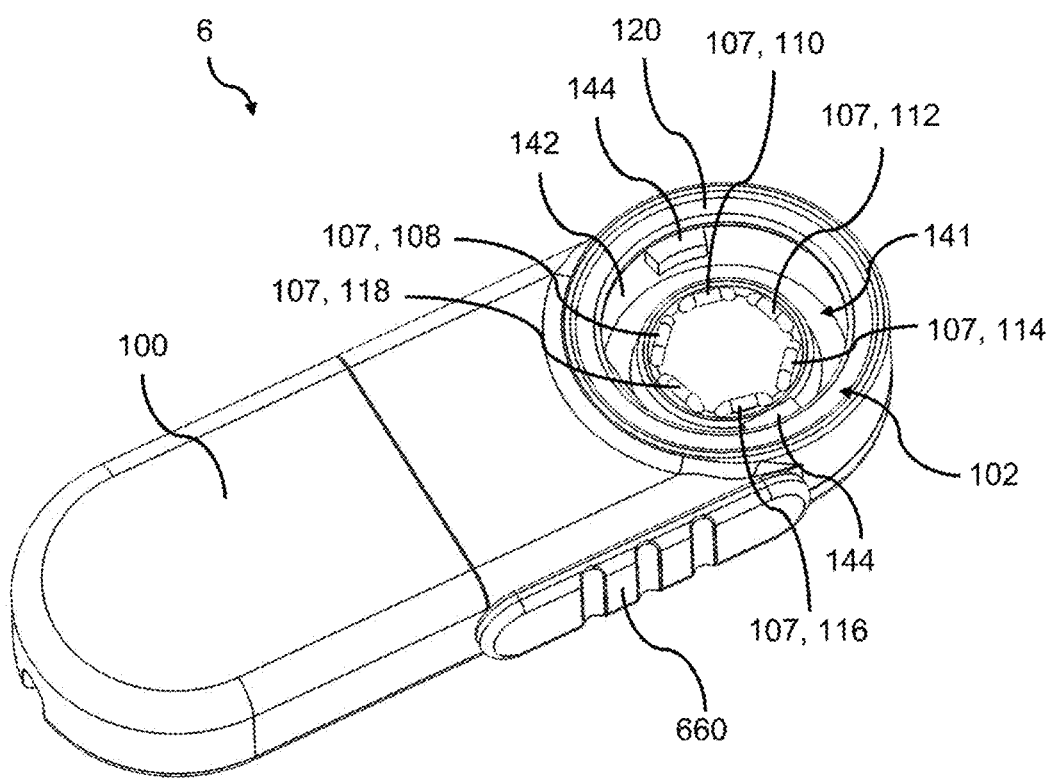

FIG. 23 schematically illustrates a monitor device 6 including a first interface 102. As shown, the first interface 102 comprises a monitor device coupling part 120 and a plurality of terminals 107, such as a ground terminal 108, a first terminal 110, a second terminal 112, a third terminal 114, a fourth terminal 116 and a fifth terminal 118. The first interface 102, for example, the monitor device coupling part 120 of the first interface 102, is configured to releasably and structurally (for example, mechanically) couple the monitor device 6 to other components of the ostomy system, such as a base plate. For example, the first interface 102 and/or the monitor device coupling part 120 of the first interface 102 may be configured to releasably and structurally couple the monitor device to the monitor interface 207 of a base plate 4 (see, for example FIG. 22). The illustrated example of the monitor device coupling part 120 comprises a recess 141 defined by a wall portion 142 in the monitor device 6. One or more tabs 144 extends from the wall portion 142 into the recess 141. The illustrated example includes two tabs 144. In examples, the one or more tabs 144 may be substantially rectangular, cylindrical, rounded, or spherical.

To facilitate mechanical connection of the monitor device coupling part 120 with the first connector 211 of the base plate 4, as illustrated in FIG. 22, the recess 141 may be sized to fit over the rim 500 of the coupling part of the base plate, with the tabs 144 aligned with the entry openings 507 in the slots 505 of the monitor interface 207 of the base plate. The monitor device coupling part 120 of the monitor device 6 and the coupling part 210 of the base plate 4 are configured to cooperate as what are sometimes referred to as bayonet or luer connectors.

Also illustrated is an actuation member 660 of the monitor device 6. The actuation member 660 may comprise a slider, as illustrated. Alternatively or additionally, the actuation member could comprise a button and/or a switch. One of the tabs 144 may be latched onto the actuation member 660, such that actuation of the actuation member may cause the respective tab 144 to retract into the wall portion 142, facilitating decoupling of the monitor device 6, for example from a base plate.

Figure 24A:
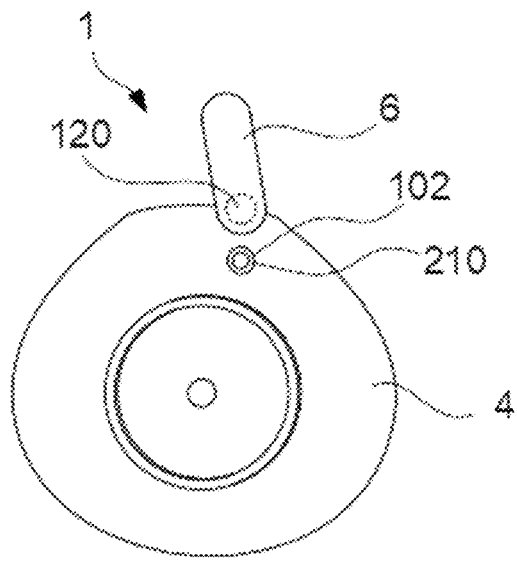
FIGS. 24A-24C illustrate a sequence of steps for an exemplary connection of a monitor device to a base plate.
Figure 24B:
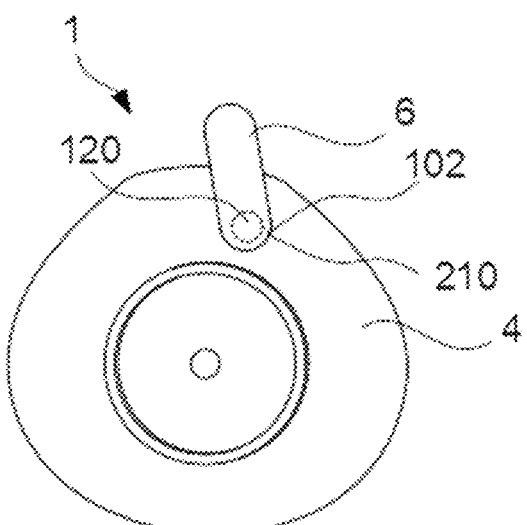
Figure 24C:
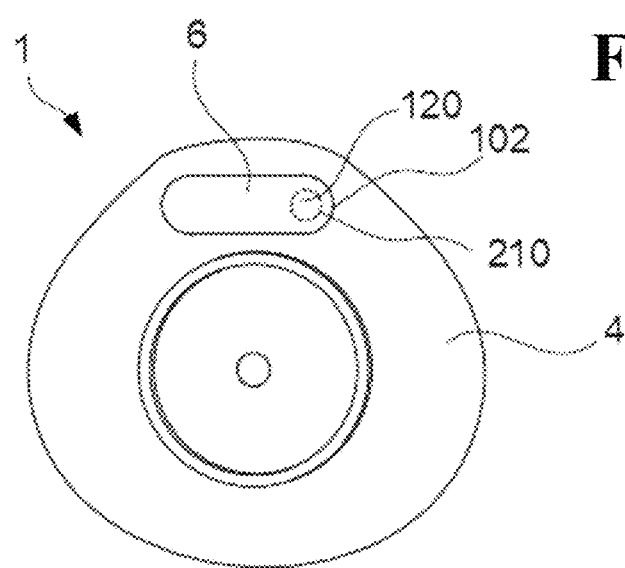

FIGS. 24A-24C illustrate a sequence of steps for an exemplary connection of a monitor device 6 to a base plate 4, such as the monitor device 6 as illustrated in FIG. 23 and the base plate 4 as illustrated in FIG. 22. FIG. 24A illustrates the monitor device 6 and the base plate 4 being decoupled. FIG. 24B illustrates the monitor device 6 being in an attachment position relative to the base plate 4. FIG. 24C illustrates the monitor device 6 and the base plate 4 being coupled.

As shown in FIGS. 24A and 24B, when attaching the monitor device 6 to the base plate 4, the monitor device 6 is moved from a detached position and orientation (FIG. 24A), wherein the monitor device 6 is separate from the base plate 4, to an attachment position and orientation (FIG. 24B) wherein the monitor device coupling part 120 of the monitor device 6 is over and in alignment with the coupling part 210 of the base plate 4. Tabs 144 of the monitor device coupling part 120 (see FIG. 23) may be aligned or registered with the entry openings 507 of the channels 505 of the base plate coupling part 210 (see FIG. 22), when the monitor device 6 is in the attachment position.

To fully couple the monitor device 6 to the base plate 4, the monitor device 6 is rotated to a coupled position and orientation (FIG. 24C). During the rotation of the monitor device 6 from the attachment position to the coupled position, the tabs 144 of the monitor device (see FIG. 23) may be guided in the channels 505 of the base plate (see FIG. 22), causing the monitor device coupling part 120 of the monitor device 6 to mechanically engage and connect to the first connector 211 of the base plate 4. The rotation may be smaller than 180 degrees, such as less than 90 degrees, as illustrated. The rotation may be at least partly clockwise and/or at least partly counter-clockwise. In the illustrated example, the rotation of the monitor device 6 is stopped to register the monitor device at the coupled position (FIG. 24C) by the tabs 144 engaging the stops 514 of the base plate coupling part 210 (see FIGS. 22 and 23).

To remove the monitor device 6, the monitor device 6 may be rotated from the coupled position (FIG. 24C) to the attachment position (FIG. 24B) with respect to the base plate 4.

The tabs 144 of the monitor device coupling part 120 are thereby moved to the entry openings 512 in the slots 504 of the base plate first connector 211 (see FIG. 11). The monitor device 6 can then be disengaged and removed from the base plate 4.

In addition to the monitor device 6, one or more other ostomy accessories may be coupled to the coupling part 210 of the base plate 4 similar to the rotational connection described in FIGS. 24A-24C. Similarly, in addition to the base plate 4, the monitor device 6 may be coupled to one or more other ostomy accessories similar to the rotational connection described in FIG. 24A-24C. The one or more ostomy accessories may include but not limited to a diagnostic device, a cleaning device, a repairing device, a protector, a coupling cap, a power source, an energy storage device, and a data transfer device.

The coupling part 210 is attached to the base plate 4 in a distance radially inwards from the periphery of the base plate larger than 5 mm, such as larger than 10 mm, such as larger than 15 mm from the periphery. Hereby, peeling of the adhesive layer is reduced, as well of the risk of the base plate 4 detaches from the peristomal skin of a user is reduced.

FIG. 25 is a cross-sectional schematic illustration of a first interface 102 of an exemplary monitor device 6 and a first connector 211 of an exemplary base plate 4 and/or sensor assembly part 700 in a coupled position, for example such as the monitor device 6 and base plate 4 as described in relation to FIGS. 22-24. As shown, the monitor device coupling part 120 of the monitor device 6 is structurally coupled to the coupling part 210 of the base plate 4 and/or sensor assembly part 700 in the connected position. Additionally, the plurality of terminals 212 of the base plate 4 and/or sensor assembly part 700 is electrically coupled to the plurality of terminals 107 of the monitor device in the connected position. In the connected position, the tabs 144 of the monitor device 6 are engaged with the channels 505 of the base plate 4 and/or sensor assembly part 700, and the rim 500 of the base plate 4 and/or sensor assembly part 700 is coupled to the recess 141 of the monitor device 6. The base plate plane P is illustrated by a dotted line. The base plate plane P is parallel to the extent of the top layer 208, and well as parallel with the base 504 of the coupling part 210. The electrode assembly 204 is positioned between the top player 208 and the first adhesive layer 200. The first adhesive layer 200 adapted to adhere the base plate 4 to the peristomal skin of a user.

Figure 26:
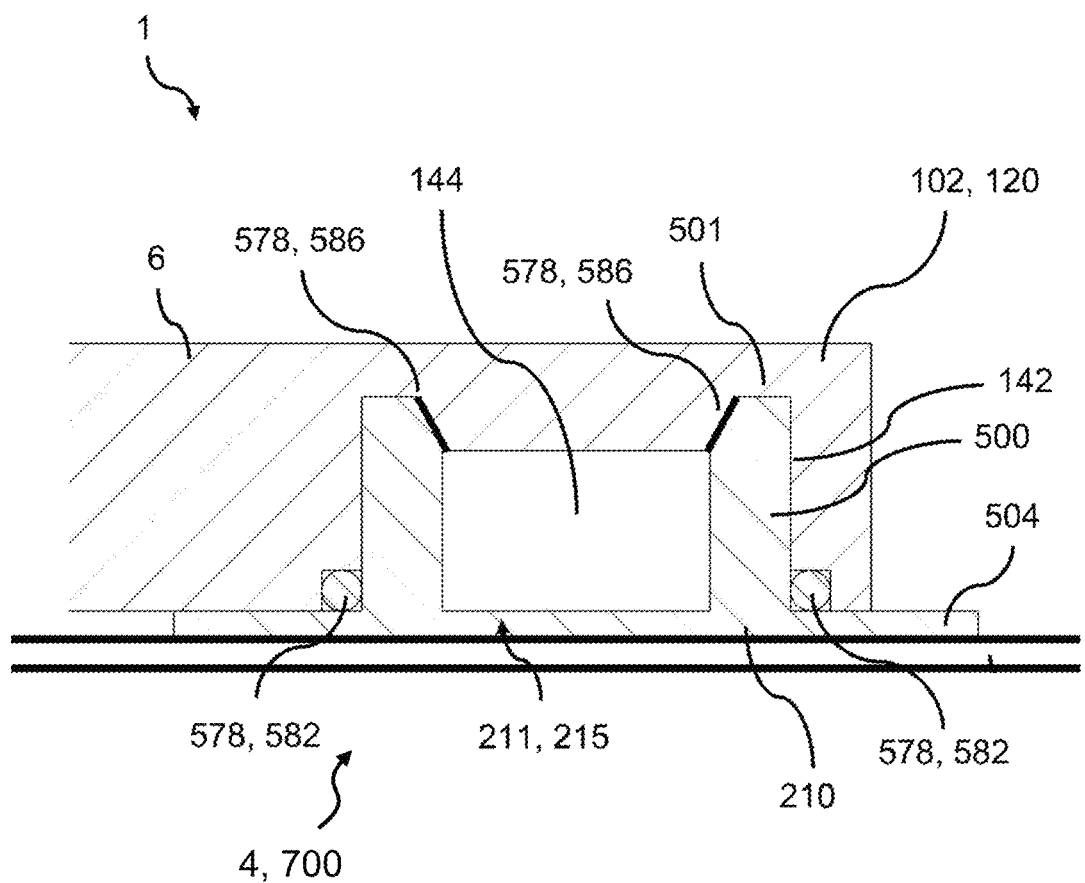

FIG. 26 schematically illustrates waterproofing elements 578 of the base plate 4 and/or sensor assembly part 700 and/or monitor device 6. As shown, the base plate 4 and/or the monitor device may comprise one or more waterproofing elements 578. The waterproofing element(s) 578 is configured to create a substantially waterproof seal between the monitor device 6 and the base plate 4 and/or sensor assembly part 700 at the coupling parts 210, 120. Such a seal may prevent undesired substances, such as output and/or cleaning solution, from contaminating the plurality of terminals 107, 212. The one or more waterproofing elements 578 may comprise a ring 582. The ring 582 may be shaped in circle, oval, or polygon. The ring 582 may comprise rubber, polyurethane, and/or silicone. The one or more waterproofing elements 578 may comprise a conical region 586. The conical region 586 may be deformable. The conical region 586 may comprise rubber, polyurethane, and/or silicone.

The waterproofing element 578 may be configured to engage the monitor device coupling part 120 of the monitor device 6 when the waterproofing element is part of the base plate 4 and/or sensor assembly part 700. Similarly, the waterproofing element 578 may be configured to engage the coupling part 210 of the base plate 4 and/or sensor assembly part 700 when the waterproofing element is part of the monitor device 6.

The waterproofing element 578 may be releasably attached (for example replaceable by the user) to the base plate 4 and/or sensor assembly part 700 and/or the monitor device 6. For example, the waterproofing element 587 may be disposed on the base of the coupling part 210, as illustrated, on the distal end 501 of the rim 500, on the inner surface 540 of the rim 500, on the outer surface 544 of the rim, or any other reasonable disposition. The ring 582 may also be disposed on the monitor device, for example on the wall portion 142 of the recess 141.

Figure 27:
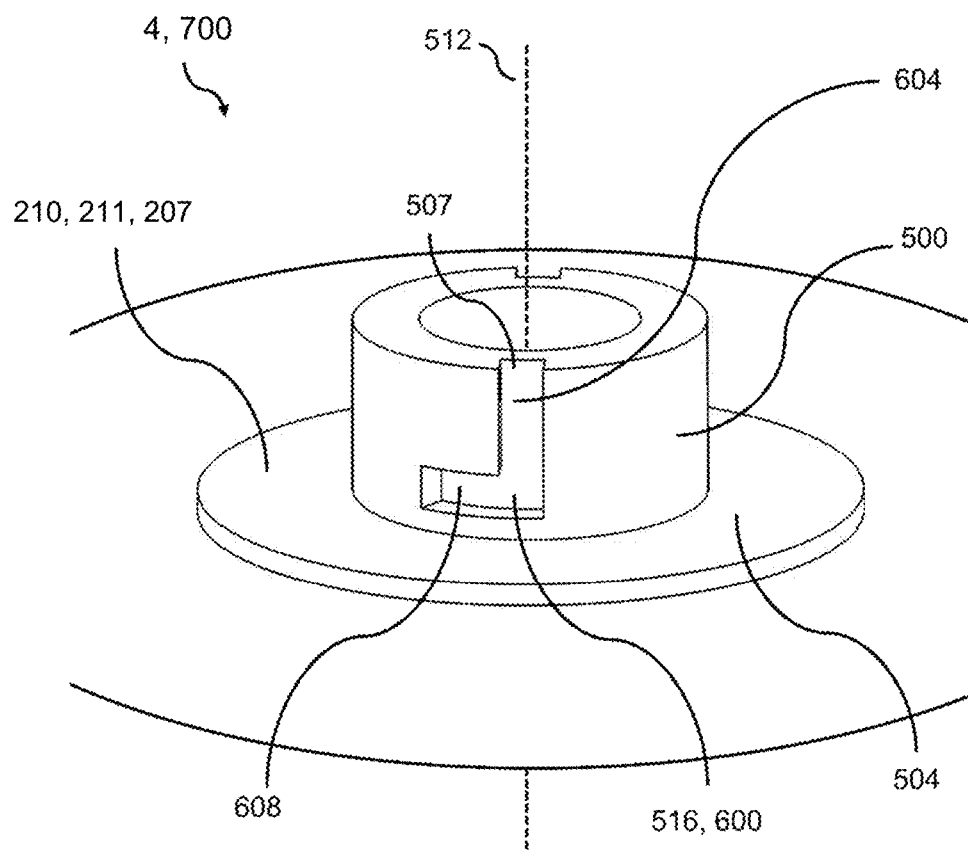

FIG. 27 schematically illustrates an exemplary coupling part 210 including a segmented channel 600, as a part of the alignment member 516. The monitor device 6 may be rotated about the longitudinal axis 512 of the rim 500 and/or pushed translationally towards the base 504 of the coupling part 210 to transition from the attachment position (FIG. 24B) to the coupled position (FIG. 24C). As illustrated, the segmented channel 600 may comprise one or more segments 604, 608, such as one or more longitudinal segments 604 extending substantially parallel to the longitudinal axis 512 of the rim 500 and/or one or more transversal segments 608 extending substantially circumferentially about the longitudinal axis 512. The transversal segments 608 may be perpendicular to the longitudinal segments 604, as illustrated.

A force may be exerted by the coupling part 210 of the base plate and/or sensor assembly part onto the monitor device coupling part 120 of the monitor device 6, for example when the user rotationally couples the base plate and/or the sensor assembly part and the monitor device from the attachment position (for example FIG. 24B) to the coupled position (for example FIG. 24C). The force may be exerted when the one or more tabs 144 of the monitor device 6 (for example as illustrated in FIG. 23) engage with the one or more channels 505 of the alignment member 516 of the base plate 4 and/or the sensor assembly part 700.

The user may apply an engagement force on the monitor device 6 in an engagement direction relative to the base plate and/or the sensor assembly part, for example in order to overcome the force exerted by the coupling part 210 onto the monitor device coupling part. In the illustrated example, the engagement force may be perpendicular to the base plate and/or the sensor assembly part while tabs of the monitor device is in the longitudinal segments 604, while the engagement force may be substantially parallel to the base plate and/or the sensor assembly part while the tabs of the monitor device is in the transversal segments 608. In order to ease coupling, the engagement force while in moving the monitor device along the longitudinal axis 512 may be rather small. On the other hand, the engagement force applied in order to rotate the monitor device about the longitudinal axis 512 may be easier overcome since a counterforce in this direction may be provided by the adhesion of the base plate 4 and/or the sensor assembly part 700 to the skin of the user.

Figure 28:
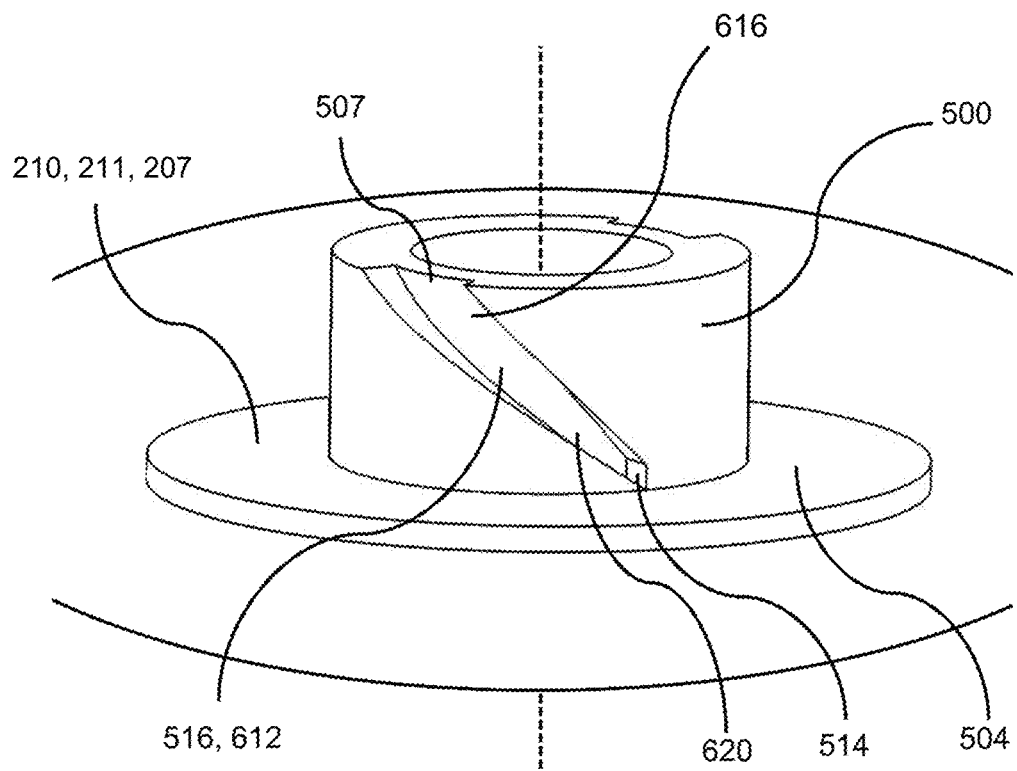

FIG. 28 schematically illustrates an exemplary coupling part 210 including a variable width channel 612, as a part of the alignment member 516. As illustrated, the variable width channel 612 may comprise a wide region 616 and a narrow region 620. The wide region 616 may be nearer to the entry opening 507 of the channel and configured to receive the tab 144 of the monitor device 6 (for example as illustrated in FIG. 23). At the wide region 616, the coupling part 210 creates little resistance against the rotational coupling from the attachment position to the coupled position. The narrow region 620 of the variable width channel 612 may be nearer to the base 504 of the coupling part 210 and/or the stop 514 of the channel. At the narrow region 620, the coupling part 210 creates more resistance, for example against rotational release from the coupled position to the attachment position. Such a variable width channel 612 may improve the coupling security between the monitor device 6 and the base plate 4 and/or the sensor assembly part 700.

Figure 29:
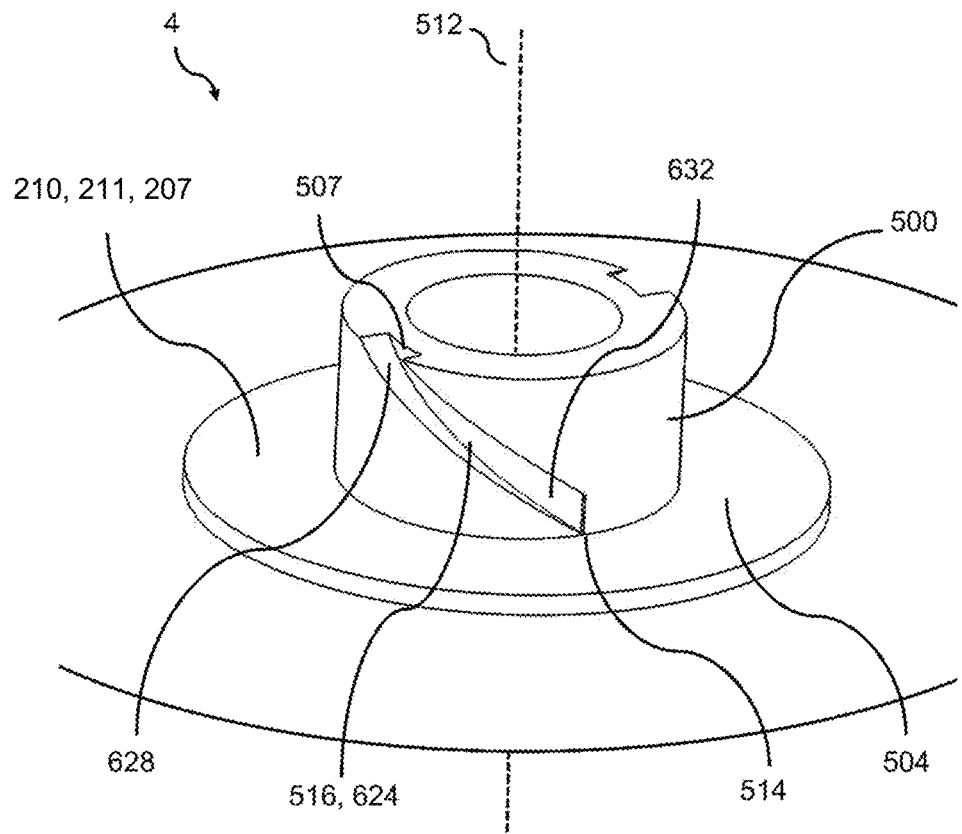

FIG. 29 schematically illustrates an exemplary a coupling part 210 including a variable depth channel 624, as a part of the alignment member 516. As illustrated, the variable depth channel 624 may comprise a deep region 628 and a shallow region 632. The deep region 628 may be nearer to the entry opening 507 of the channel and configured to receive the tab 144 of the monitor device 6 (for example as illustrated in FIG. 23). At the deep region 628, the coupling part 210 creates little resistance against the rotational coupling from the attachment position to the connected position. The shallow region 632 of the variable width channel 612 may be nearer to the base 504 of the coupling part 210 and/or the stop 514 of the channel. At the shallow region 632, the coupling part 210 creates more resistance against the rotational release from the connected position to the attachment position. Such a variable depth channel 624 may improve the coupling security between the monitor device 6 and the base plate 4 and/or the sensor assembly part 700.

Figure 30:
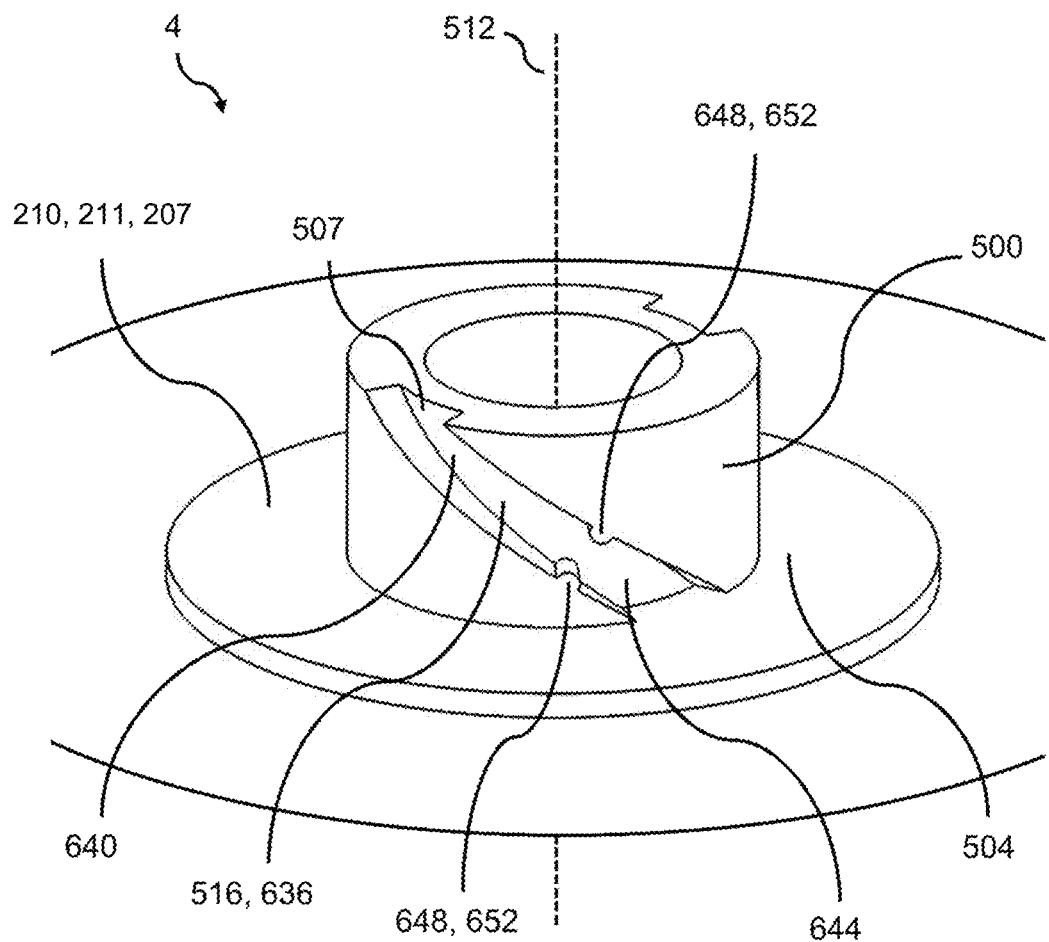

FIG. 30 schematically illustrates an exemplary coupling part 210 including a pocketed channel 636, as a part of the alignment member 516. As illustrated, the pocketed channel 636 may comprise a guiding region 640 and a pocketing region 644 separated by a pocketing element 648. The guiding region 640 may be configured to guide the tab 144 of the monitor device 6 (for example as illustrated in FIG. 23) from the entry opening 507 of the channel to the pocketing element 648. A pocketing force (for example, a rotational force about the longitudinal axis 512 of the rim 500), such as an engagement force, may be applied to the monitor device 6 to move the tab 144 past the pocketing element 648 and into the pocketing region 644 of the pocketed channel 636. Once the tab 144 is pocketed or secured in the pocketing region 644 of the pocketing channel, the monitor device 6 may be in the second or coupled position (for example FIG. 24C) relative to the base plate 4 and/or the sensor assembly part. A de-pocketing force (for example, opposite of the pocketing force), such as a disengagement force, may be applied to the monitor device 6 to move the tab 144 from the pocketing region 644 past the pocketing element 648 and into the guiding region 640.

The pocketing element 648 may comprise one or more protuberances 652, as illustrated. Alternatively or additionally, the one or more protuberances 652 may comprise compliant materials (for example plastics) configured to elastically deform when engaged by the tabs 144 of the monitor device 6 when the pocketing force or the de-pocketing force is applied.

The one or more protuberances 652 may form a gap smaller than the tab 144 such that the protuberances prevent the tab from passing when not deformed by the pocketing force or the de-pocketing force. In embodiments, the pocketing element 648 may comprise a separation wall separating the guiding region 640 and the pocketing region 644 of the pocketed channel 636.

As illustrated in FIGS. 28-30, the alignment member may be inclined with respect to the base plate and/or the sensor assembly part. Thus, the user may apply an engagement force on the monitor device in an engagement direction relative to the base plate and/or the sensor assembly part in order to couple the monitor device to the base plate 4 and/or the sensor assembly part 700. The engagement direction forms an engagement angle with the base plate 4 and/or the sensor assembly part 700, such as a base plate plane extended by the base plate and/or the sensor assembly part. For example, the engagement angle may be between 0 and 45 degrees, for example in order to ease coupling and/or release, since a counterforce in this direction may substantially be provided by the adhesion of the base plate 4 and/or the sensor assembly part 700 to the skin of the user.

Figure 31:
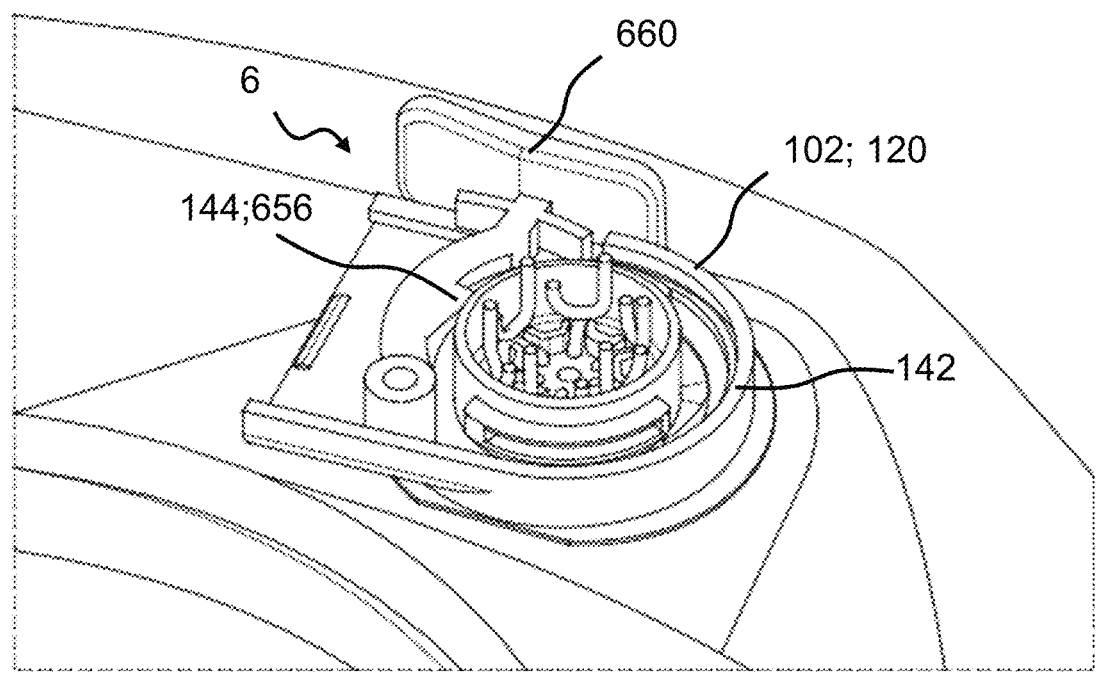

FIG. 31 schematically illustrates parts of the monitor device 6 including an optional actuatable tab 656. The actuatable tab 656 may be configured to protrude off from the wall portion 142 of the monitor device coupling part 120, which may be denoted as an unactuated position. The actuatable tab 656 may be configured to retract into the wall portion 142 when actuated into an actuated position. The actuatable tab 656 may be de-actuated, for example moved to the unactuated position, when the tab 144 is guided from the entry opening 507 through the guiding region 640 to the pocketing element 648 (as illustrated in FIG. 30). The actuatable tab 656 may be actuated to move the tab 144 from the guiding region 640 past the pocketing element 648 and into the pocketing region 652, where the actuatable tab may be de-actuated or released such that the actuatable tab resides in the pocketing region 652. The actuatable tab 656 may be de-actuated when the tab 144 is pocketed or secured in the pocketing region 644 to help avoid unintentional decoupling between the base plate and/or sensor assembly part and the monitor device. The actuatable tab 656 may be latched onto an actuation member 660. The actuation member 660 may comprise a slider, as illustrated, a button, or a switch. The actuatable tab 656 may be spring-loaded to exert a force against the coupling part 210 of the base plate 4 and/or the sensor assembly part 700 (for example in the coupled position as in FIG. 24C). For example, the actuatable tab 656 may be spring-loaded towards the unactuated position. Such a force may improve security of the coupling between the monitor device 6 and the base plate 4 and/or the sensor assembly part 700.

Figure 32:
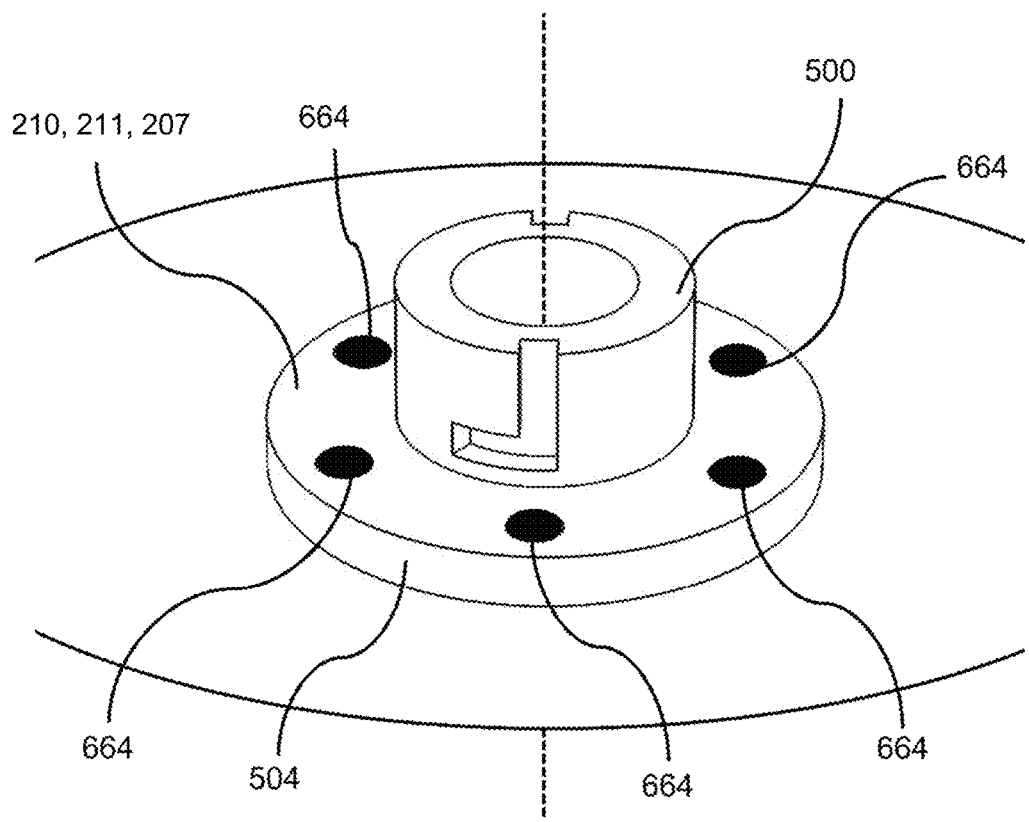
Figure 33:
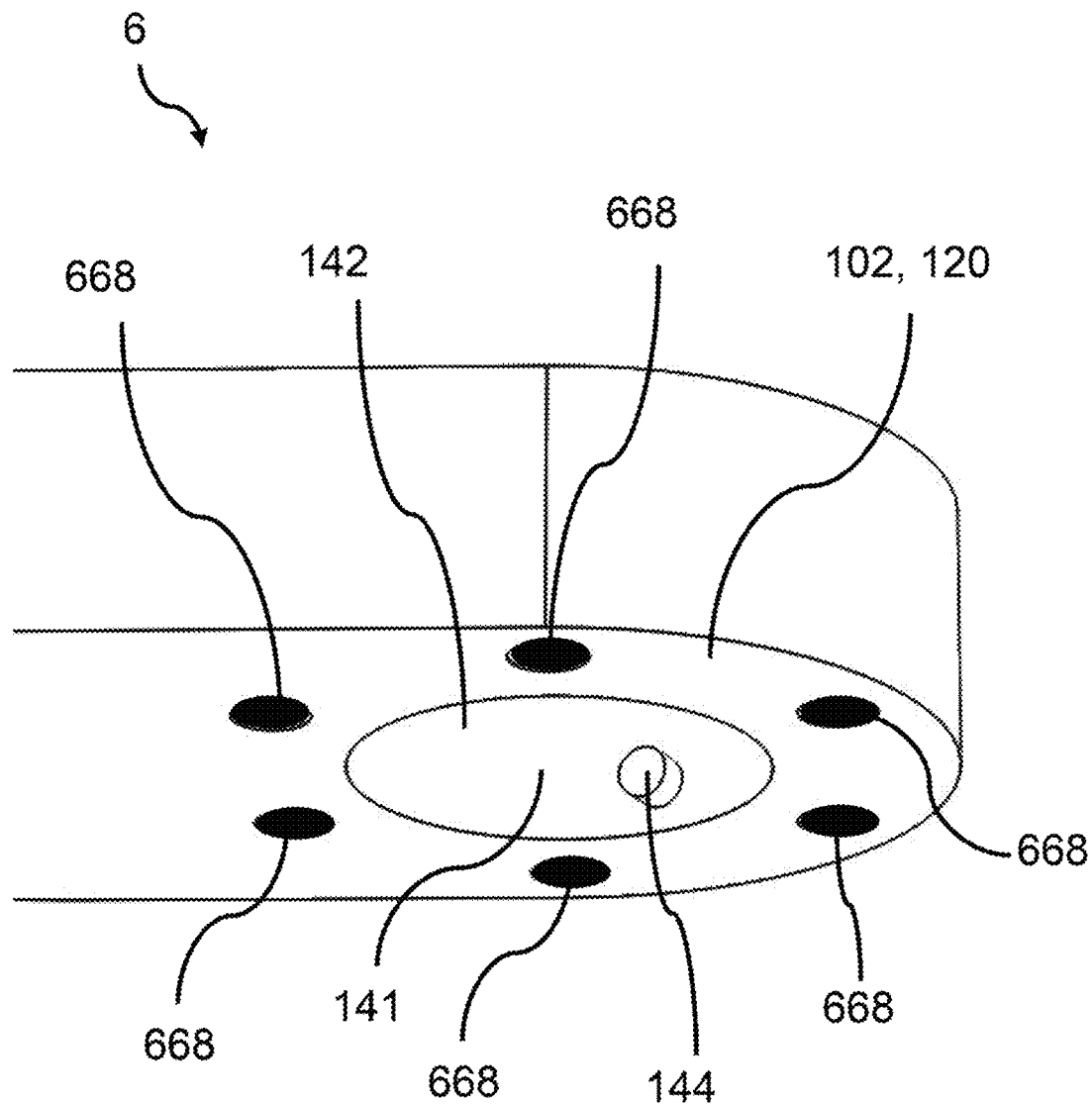
FIG. 33 illustrates part of an exemplary monitor device.

FIG. 32 illustrates a coupling member 210 including one or more magnetic elements 664, while FIG. 33 illustrates part of an exemplary monitor device 6 including one or more magnetic elements 668. FIGS. 32 and 33 are described collectively in the following.

The one or more magnetic elements 664 of the base plate 4 and/or the sensor assembly part 700 may be configured to be magnetically coupled to the one or more magnetic elements 668 of the monitor device. The magnetic coupling between the monitor device 6 and the base plate 4 and/or the sensor assembly part 700 may be configured to provide additional security to the coupling by requiring a disengagement force, larger than the attractive magnetic force between the one or more magnetic elements 664 of the base plate 4 and/or the sensor assembly part 700 and the one or more magnetic elements 668 of the monitor device 6, for example in the coupled position (FIG. 24C).

The one or more magnetic elements 664 of the base plate 4 and/or the sensor assembly part 700 and the one or more magnetic elements 668 of the monitor device 6 may be arranged symmetrically, for example ring-shaped, as illustrated in FIGS. 32 and 33, or asymmetrically. The one or more magnetic elements 664 of the base plate 4 and/or the sensor assembly part 700 may be disposed on or in the base 504 of the coupling part 210, as illustrated. However, any other reasonable disposition may be considered (for example on or in the rim 500). Similarly, the one or more magnetic elements 668 of the monitor device 6 may be disposed on or in the monitor device coupling part 120 in any reasonable arrangement.

The one or more magnetic elements 664, 668 are at least one of ferromagnetic, paramagnetic, diamagnetic, ferromagnetic, and antiferromagnetic.

Figure 34:
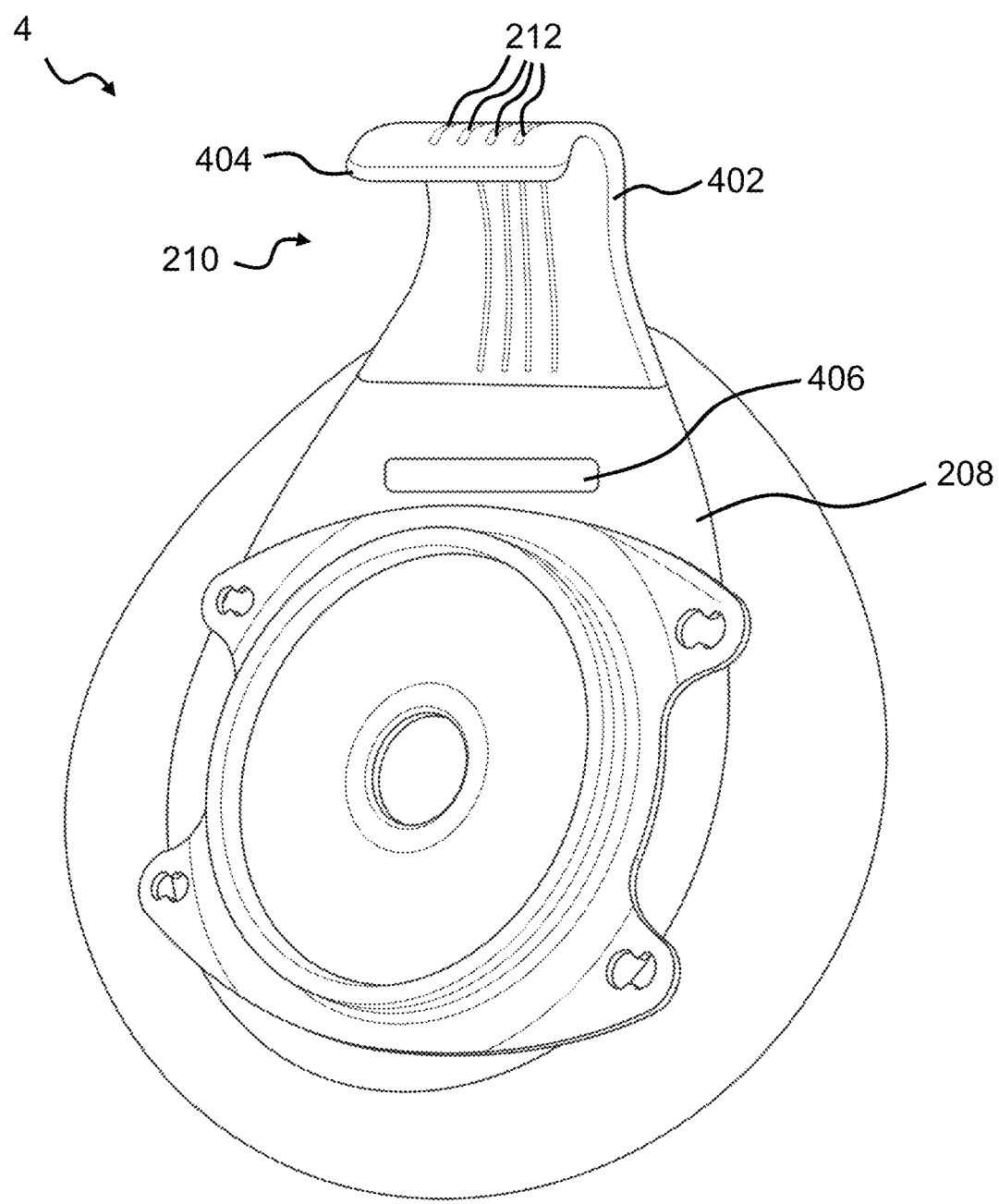
FIG. 34 shows a schematic representation of an exemplary base plate.

FIG. 34 shows a schematic representation of an exemplary base plate 4, such as a base plate 4 as illustrated in previous figures, such as FIGS. 15-20. The base plate 4 comprises a top layer 208, a first adhesive layer 200 (see for example FIGS. 11a and 11b) and an electrode assembly 204 (see for example FIGS. 11a and 11b) comprising a plurality of electrodes 216. The base plate 4 may comprise other optional layers as explained above, such as an optional second adhesive layer 204 (see for example FIGS. 11a and 11b), for example arranged between the top layer 208 and the electrode assembly 204.

The base plate 4 further comprises a monitor interface configured for connecting the base plate 4 to a monitor device. The monitor interface comprises a plurality of terminals 212 electrically connected to the plurality of electrodes. The plurality of terminals 212 is configured to connect with respective terminals of the monitor device. The monitor interface comprises a coupling part 210 configured for coupling between the monitor device and the base plate 4.

The coupling part 210 comprises a flexible element 402 configured to form a loop element. The flexible element 402 has a first loop end 404. The first loop end 404 is configured to be attached to a distal side of the top layer 208, such as the loop attachment part 406.

The flexible element 402 (and the loop element being formed by the flexible element 402) may be formed as illustrated for example in relation to FIGS. 15 and 17, wherein a hole is provided in the top layer 208 and the optional second adhesive layer 202. The flexible element 402 (and the loop element being formed by the flexible element 402) may thereby be formed by the electrode assembly 204 and optionally the top layer 208, such as a first part of the electrode assembly and a first part of the top layer 208.

Figure 35:
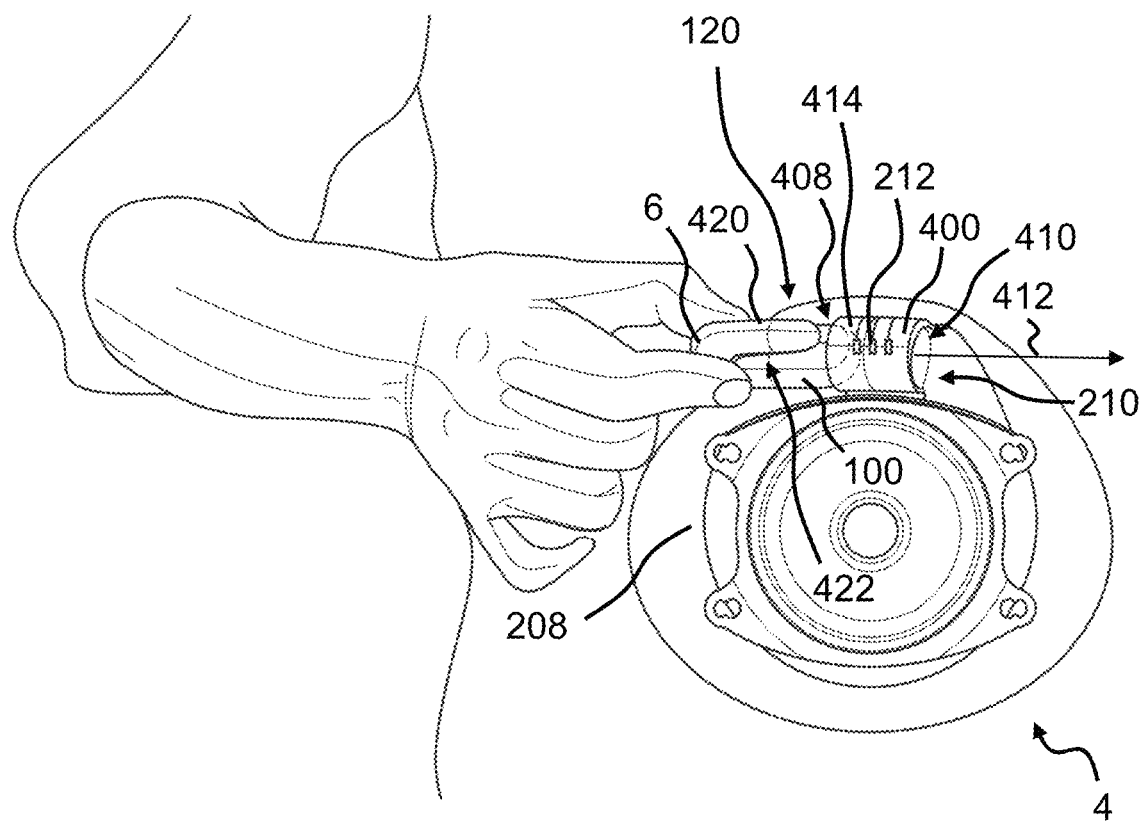
FIG. 35 shows a schematic representation of an exemplary base plate,
FIG. 36 schematically illustrates an exemplary base plate,
FIG. 37 schematically illustrates an exemplary base plate,
FIG. 38 schematically illustrates an exemplary base plate,
FIG. 39 schematically illustrates an exemplary base plate,
FIG. 40 schematically illustrates an exemplary base plate,
FIG. 41 schematically illustrates an exemplary base plate,
FIG. 42 schematically illustrates an exemplary base plate,
FIG. 43 schematically illustrates an exemplary base plate.

FIG. 35 shows a schematic representation of an exemplary base plate 4. The base plate 4 as illustrated in FIG. 35 may be the base plate 4 as illustrated in FIG. 34, and wherein the flexible element 402 has been positioned such that the first loop end 404 is attached to the loop attachment part 406 to form the loop element 400 as illustrated in FIG. 35.

The loop element 400 may be formed by the user, for example in accordance with the description in relation to FIG. 34. Alternatively, the loop element 400 may be made during manufacture of the base plate 4. Thus, the loop element 400 may be provided on the base plate 4 when provided to the user.

The loop element 400 forms a conduit between a first opening 408 and a second opening 410. The coupling part 210 may be configured to receive at least a part of the monitor device 6 through the first opening 408, as illustrated, by a linear motion in an engagement direction of the monitor device 6 relative to the base plate 4. For example, the coupling part 210 may be configured to receive the monitor device housing 100 of the monitor device 6 or a first clip element 420 of the monitor device 6.

The coupling part 210 may alternatively or additionally, be configured to receive the at least part of the monitor device 6 through the second opening 410. For example, the coupling part 210 may be configured to allow flexibility in that the user may decide which direction to couple the monitor device 6 to the base plate 4. Thus, the coupling part 210 may be configured to receive the at least part of the monitor device 6 by a linear motion in a first engagement direction 412 and a second engagement direction (not shown). The first engagement direction 412 may be opposite the second engagement direction.

The engagement direction(s), such as the first engagement direction 412 and/or the second engagement direction, may be substantially parallel to the base plate 4. For example, the base plate 4, such as the top layer 208 and the first adhesive layer is substantially planar, for example prior to being applied to a user's skin, and extend in a base plate plane, and the engagement direction(s) 412 is substantially parallel to the base plate plane. The engagement direction(s) 412 may form an engagement angle with the base plate, such as with the base plate plane, for example at the position of the coupling part 210, and the engagement angle may be less than 45 degrees, such as between 0 and 45 degrees.

The plurality of terminals 212 may be provided on an outside surface of the loop element 400 as illustrated. This may be advantageous if the plurality of electrodes is provided on a proximal side of the electrode assembly. Alternatively, the plurality of terminals 212 may be provided on an inside surface of the loop element 400, such as inside the conduit formed by the loop element 400, for example to shield the plurality of terminals 212 from user interaction.

FIG. 35 also shows an exemplary monitor device 6 for connecting to the base plate 4. The monitor device comprises a monitor device housing 100, electronic circuitry (see for example FIG. 2); and an appliance interface 102 comprising a monitor device coupling part 120 (see for example FIG. 2). The appliance interface is configured for connecting the monitor device 6 to the base plate 4. The appliance interface comprises a plurality of terminals 108, 110, 112, 114, 116, 118 (see for example FIG. 2) for connecting with a plurality of electrodes of the base plate, such as through a plurality of terminals 212 of the base plate 4.

The appliance interface 102 comprises a monitor device coupling part 120 configured for coupling, such as mechanical coupling, between the monitor device 6 and the base plate 4. In the illustrated example, the monitor device coupling part 120 comprises a first clip element 420 forming a first slit 422 configured to receive an element of the base plate 4, such as the loop element 400 and/or a part of the loop element 400, as illustrated. The first slit 422 is formed between the first clip element 420 and the monitor device housing 100.

The monitor device coupling part 120 is configured to engage with the base plate 4 by a motion in the engagement direction(s) 412 of the monitor device 6 relative to the base plate 4, as explained in further detail above.

The plurality of terminals of the monitor device 6 may be provided inside the first slit 422. The appliance interface may be formed as part of the monitor device housing 100. For example, the plurality of terminals may be provided on the monitor device housing 100. Alternatively or additionally, the plurality of terminals may be provided on the first clip element 420. The plurality of terminals of the monitor device 6 may be provided on the monitor device 6 to correspond to the positions of the plurality of terminals 212 of the base plate 4, and whether the loop element 400 of the base plate 4 is configured to receive the clip element 420 or the monitor device housing 100 of the monitor device 6.

Figure 36:
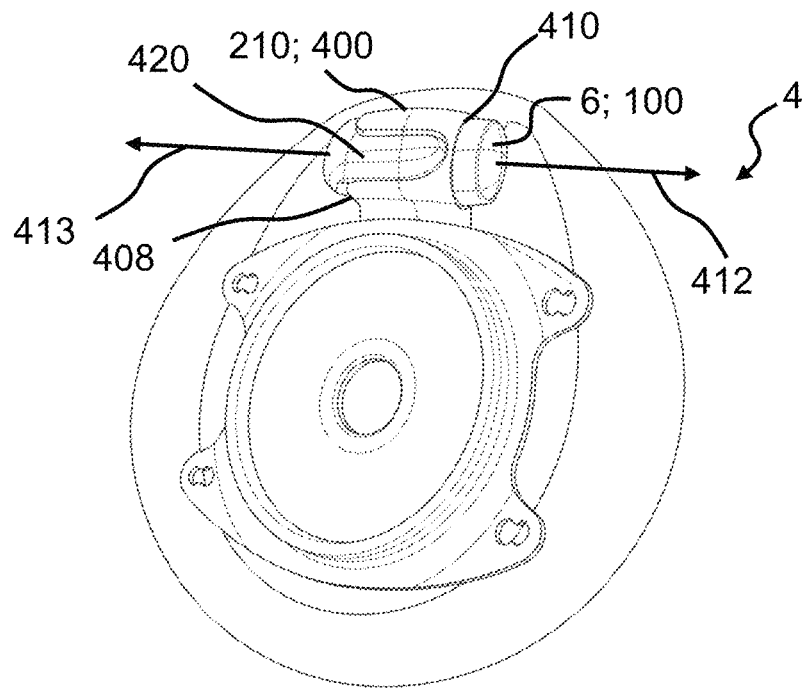

FIG. 36 schematically illustrates an exemplary base plate 4, such as the base plate 4 as explained in relation to FIGS. 34-35. The base plate 4 has a coupling part 210 comprising a loop element 400, and wherein a monitor device 6 is coupled to the base plate 4. The monitor device 6 having been coupled by insertion of the monitor device housing 100 into the loop element 400. Furthermore, it is shown that the monitor device 6 may extend into and through both the first opening 408 and the second opening 410 formed by the loop element 400.

The coupling part 210 is further configured to disengage with the monitor device 6 by a motion, such as a linear motion, in a disengagement direction 413 of the monitor device 6 relative to the base plate 4. The monitor device 6, such as the monitor device coupling part is configured to disengage with the base plate 4, such as with the coupling part 210 of the base plate 4, by a motion, such as a linear motion, in the disengagement direction 413 of the monitor device 6 relative to the base plate 4. The disengagement direction 413 may be substantially opposite the engagement direction 412, as illustrated.

The engagement direction 412 and/or the disengagement direction 413 may be substantially parallel to the base plate. For example, the base plate 4, such as the top layer 208 and the first adhesive layer is substantially planar, for example prior to being applied to a user's skin, and extend in a base plate plane, and the engagement direction and the disengagement direction 413 may be substantially parallel to the base plate plane.

The engagement direction 412 and/or the disengagement direction 413 may be substantially parallel to the base plate 4. For example, the base plate 4, such as the top layer 208 and the first adhesive layer is substantially planar, for example prior to being applied to a user's skin, and extend in a base plate plane, and the engagement direction 412 and/or the disengagement direction may be substantially parallel to the base plate plane. The engagement direction 412 and/or the disengagement direction 413 may form an engagement angle with the base plate, such as with the base plate plane, for example at the position of the coupling part 210, and the engagement angle may be less than 45 degrees, such as between 0 and 45 degrees.

Figure 37:
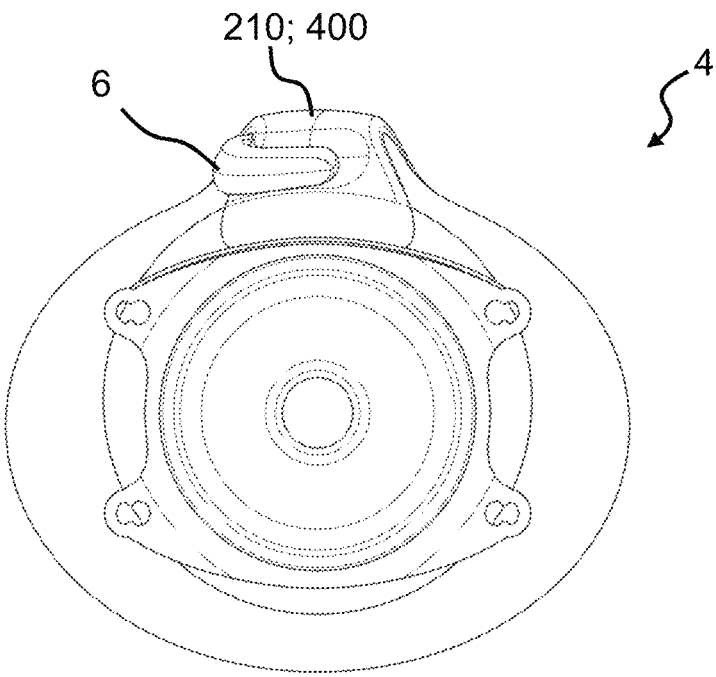

FIG. 37 schematically illustrates an exemplary base plate 4, such as the base plate 4 as explained in relation to FIGS. 34-36. However, with the difference that the loop element 400 of the base plate 4 may have been formed as illustrated in relation to FIGS. 18-20, wherein a first part 302 of the electrode assembly 204 is not covered by the first adhesive layer 200, to allow the first part 302 (together with part of the top layer and part of the optional second adhesive) to be bend around to form the loop element 400.

Figure 38:
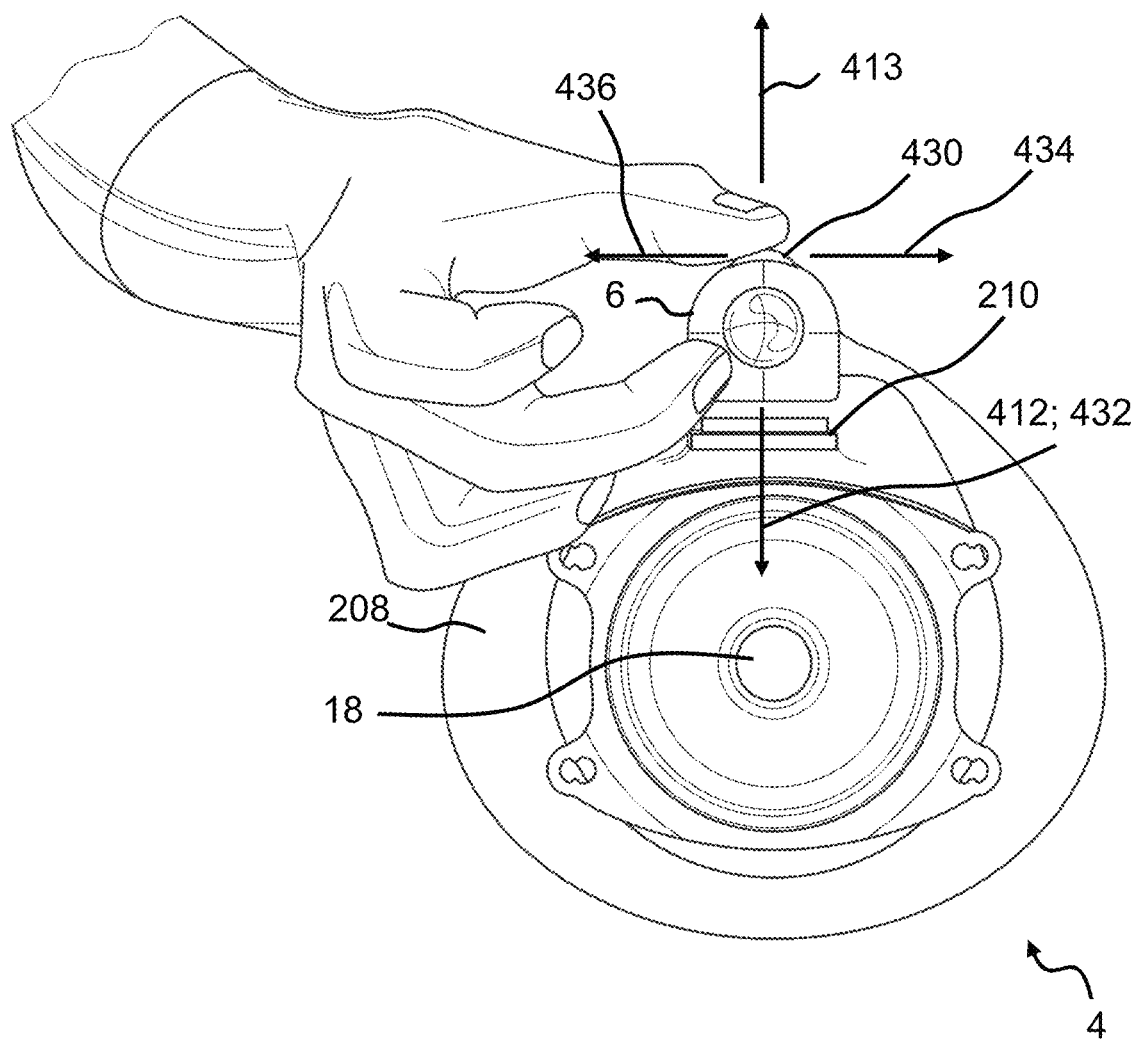

FIG. 38 schematically illustrates an exemplary base plate 4, such as the base plate as illustrated in FIG. 11a or FIG. 11b, and a monitor device 6, such as the monitor device as illustrated in FIG. 2.

The base plate 4 comprises a coupling part 210 configured for coupling between the monitor device 6 and the base plate 4. The coupling part 210 is configured to engage with the monitor device 6 by a motion, such as a linear motion, in an engagement direction 412 of the monitor device 6 relative to the base plate 4. The monitor device 6 is configured to engage with the coupling part 210 of the base plate 4 by the motion in the engagement direction 412 of the monitor device 6 relative to the base plate 4. In the present example, the engagement direction 412 is towards a stomal opening 18 of the base plate 4.

The coupling part 210 is configured to disengage with the monitor device by a motion, such as a linear motion, in a disengagement direction 413 of the monitor device 6 relative to the base plate 4. The monitor device 6 is configured to disengage with the coupling part 210 of the base plate 4 by the motion in the disengagement direction 413 of the monitor device 6 relative to the base plate 4. In the present example, the disengagement direction 413 is away from the stomal opening 18 of the base plate 4.

The top layer 208 and the first adhesive layer are substantially planar and extending in a base plate plane, for example prior to being applied to a user's skin. The engagement direction 412 and the disengagement direction 413 may be substantially parallel to the base plate plane. Alternatively or additionally, the engagement direction 412 and/or the disengagement direction 413 may form an engagement angle with the base plate plane, and the engagement angle may be less than 45 degrees, such as between 0 and 45 degrees.

As seen, the coupling part 210 of the base plate 4 is positioned such that when the monitor device 6 is coupled to the base plate 4 the top layer 208 is disposed between the monitor device 6 and the skin of the user.

The monitor device 6 and/or the base plate 4 comprises a locking mechanism configured to lock the monitor device 6 in a coupled position with the base plate 4. The locking mechanism comprises a locking element 430. The locking element 430 is, in the illustrated example, provided on the monitor device. However, in another exemplary monitor device and/or base plate, the locking element 430 may be provided on the base plate, such as on the coupling part of the base plate. The locking element 430 may be a button, such as a button deflectable in a first direction 432. The first direction 432 may be substantially parallel to the engagement direction 412, as illustrated. Alternatively, the locking element 430 may be a slider, for example slidable in a first slider direction 434 and/or a second slider direction 436. The first slider direction 434 and/or the second slider direction 436 may be substantially perpendicular to the engagement direction 412, as illustrated.

The locking element 430 is configured to unlock and/or lock the locking mechanism, such as to unlock the monitor device 6 in the coupled position with the base plate 4 and/or to lock the monitor device 6 in the coupled position with the base plate 4. For example, in the case of the locking element 430 being a slider, sliding the slider in the first slider direction 434 may lock the monitor device 6 in the coupled position with the base plate 4, and sliding the slider in the second slider direction 436 may unlock the monitor device 6 in the coupled position with the base plate 4. Alternatively, the locking mechanism may be biased, such as spring biased, towards locking of the monitor device 6 in the coupled position with the base plate 4, and the locking element 430 may be pressed or slide to unlock the monitor device 6 in the coupled position with the base plate 4.

Figure 39:
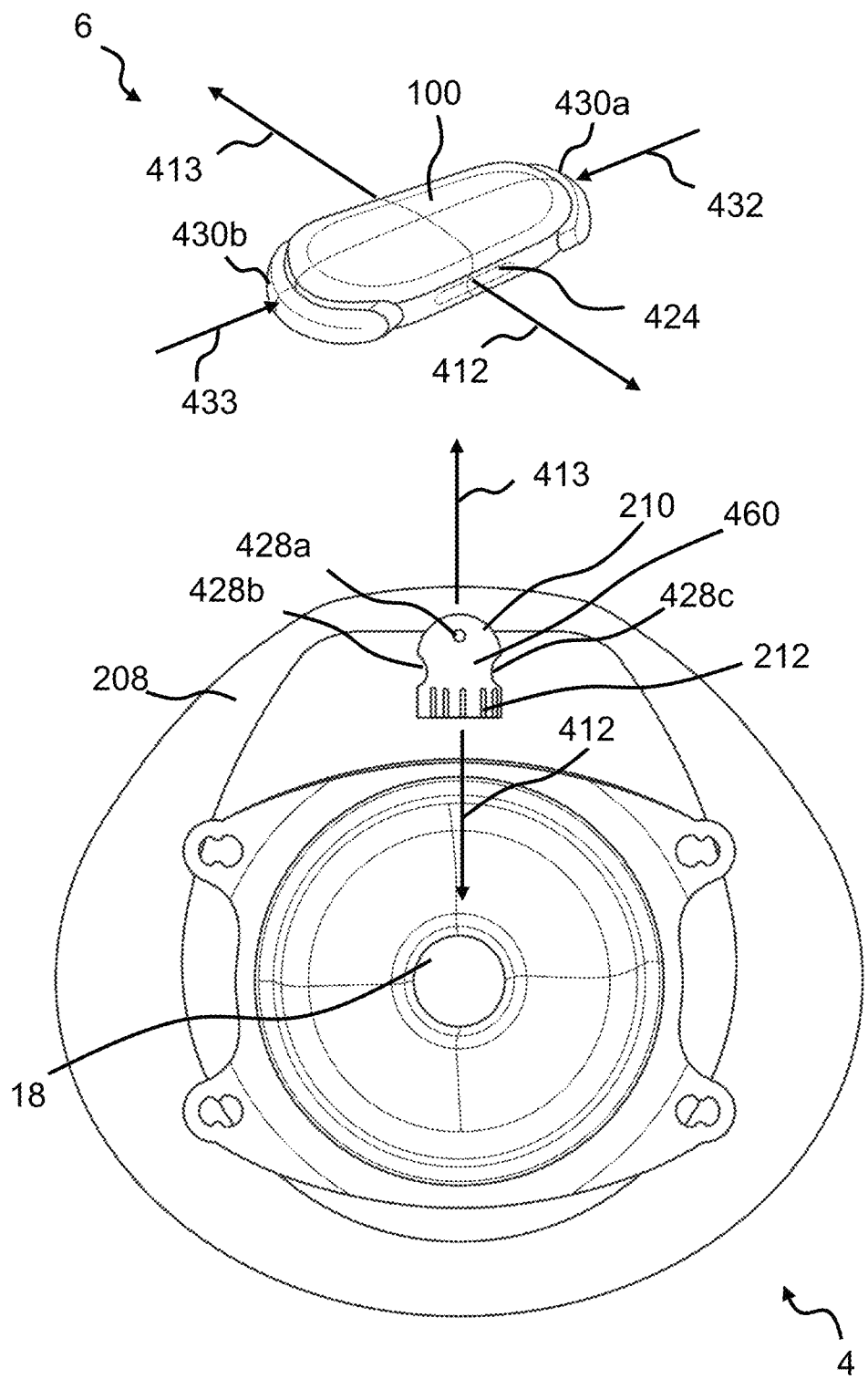

FIG. 39 schematically illustrates an exemplary base plate 4, such as the base plate as illustrated in FIG. 11*a* or FIG. 11*b*, and a monitor device 6, such as the monitor device as illustrated in FIG. 2.

The base plate 4 comprises a coupling part 210 configured for coupling between the monitor device 6 and the base plate 4. The coupling part 210 is configured to engage with the monitor device 6 by a motion, such as a linear motion, in an engagement direction 412 of the monitor device 6 relative to the base plate 4. The monitor device 6 comprises an opening 424, for example in a rim surface of the monitor device 6. The opening 424 may form a monitor device coupling part. The opening 424 is configured to receive the coupling part 210 of the base plate 4. The monitor device 6 is configured to engage with the coupling part 210 of the base plate 4 by the motion in the engagement direction 412 of the monitor device 6 relative to the base plate 4. The engagement direction 412 may be towards a stomal opening 18 of the base plate 4.

The plurality of terminals 212 of the base plate is provided on the coupling part 210. The plurality of terminals of the monitor device 6 may be provided inside the opening 424, such as to connect to the plurality of terminals 212 of the base plate 4 when the monitor device 6 is coupled to the base plate 4.

The coupling part 210 is configured to disengage with the monitor device 6 by a motion, such as a linear motion, in a disengagement direction 413 of the monitor device 6 relative to the base plate 4. The monitor device 6 is configured to disengage with the coupling part 210 of the base plate 4 by the motion in the disengagement direction 413 of the monitor device 6 relative to the base plate 4. The disengagement direction 413 may be away from the stomal opening 18 of the base plate 4.

The top layer 208 and the first adhesive layer are substantially planar and extending in a base plate plane, for example prior to being applied to a user's skin. The engagement direction 412 and/or the disengagement direction 413 may be substantially parallel to the base plate plane. Alternatively or additionally, the engagement direction 412 and/or the disengagement direction 413 may form an engagement angle with the base plate plane, and the engagement angle may be less than 45 degrees, such as between 0 and 45 degrees.

The monitor device 6 and/or the base plate 4 comprises a locking mechanism configured to lock the monitor device 6 in a coupled position with the base plate 4. The locking mechanism comprises a locking element 430 comprising a first button 430*a* and a second button 430*b*.

The first button 430*a* is deflectable in a first direction 432 and the second button 430*b* is deflectable in a second direction 433. The first direction 432 is substantially opposite the second direction 433. The first direction 432 and the second direction 433 are substantially perpendicular to the engagement direction 412 and/or the disengagement direction 413, such as to allow the user to pinch the first button 430*a* and second button 430*b* while engaging and/or disengaging the monitor device 6 to the base plate 4.

The locking element 430 is configured to unlock and/or lock the locking mechanism, such as to unlock the monitor device 6 while in the coupled position with the base plate 4 and/or to lock the monitor device 6 while in the coupled position with the base plate 4. For example, the first button 430*a* and the second button 430*b* is to be pressed simultaneously to lock and/or unlock the monitor device 6 in the coupled position with the base plate 4. For example, the first button 430*a* and the second button 430*b* may be pressed in order to lock the monitor device 6 in the coupled position with the base plate 4, and subsequently the first button 430*a* and the second button 430*b* may be pressed again to unlock the monitor device 6 in the coupled position with the base plate 4. Alternatively, the locking mechanism may be biased, such as spring biased, towards locking of the monitor device 6 in the coupled position with the base plate 4, and the first button 430*a* and the second button 430*b* may be pressed to unlock the monitor device 6 in the coupled position with the base plate 4.

The locking mechanism of the monitor device 6 is configured to cooperate with a locking section 428 of the base plate 4. The locking section 428 in the illustrated example comprises a hole 428*a* extending through the coupling part 210, a first indent 428*b* in a first edge of the coupling part 210 and a second indent 428*c* in a second edge of the coupling part 210. Thus, for example, the locking mechanism of the monitor device 6 may comprise a pin to engage with the hole 428*a* of the coupling part 210 of the base plate 4, and/or the locking mechanism of the monitor device 6 may comprise elements being deflectable perpendicular to the engagement direction 412, such as to engage with the first indent 428*b* and/or the second indent 428*c*.

Figure 40:
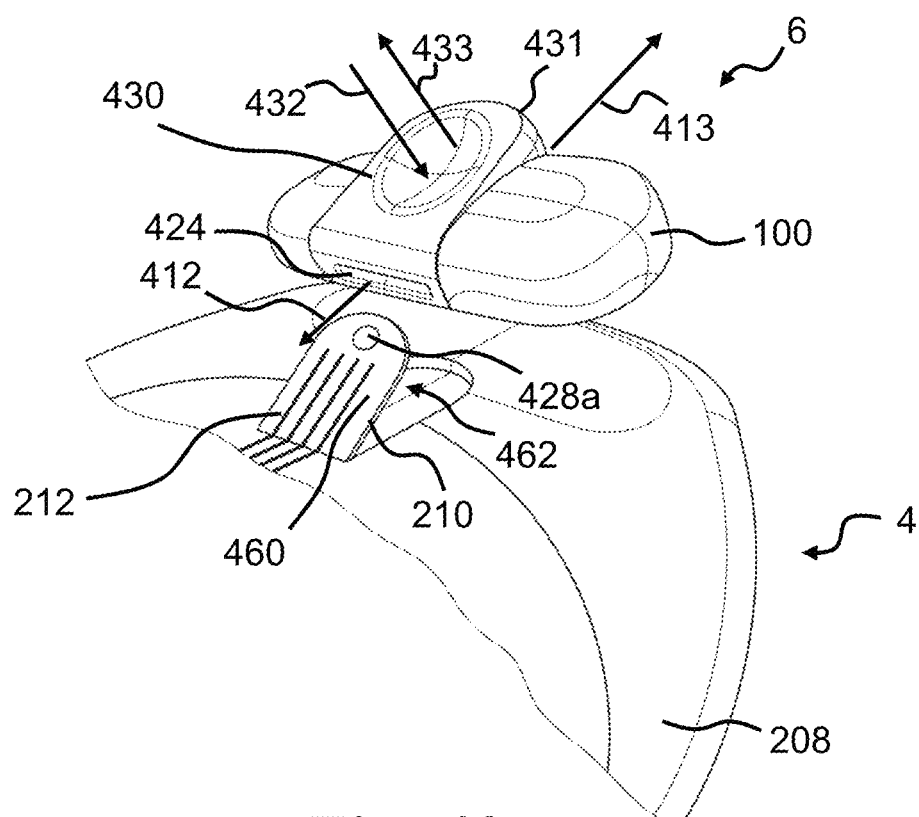

The coupling part 210 is substantially flat and comprises a first surface 460 and a second surface 462 (see FIG. 40). The second surface 462 is facing the top layer 208 and the first surface 460 is facing away from the top layer 208. The second surface 462 may be facing substantially in a proximal direction and the first surface 460 may be facing substantially in a distal direction. The plurality of terminals 212 may be provided on the first surface 460 and/or on the second surface 462 of the coupling part 210.

The second surface 462 of the coupling part 210 and the top layer 208 may be separated, such as to allow at least a part of the monitor device 6 to be positioned between the second surface of the coupling part 210 and the top layer 208, for example to allow the coupling part 210 to be received by the opening 424 of the monitor device 6.

FIG. 40 schematically illustrates part of an exemplary base plate 4, such as the base plate as illustrated in FIG. 11*a* or FIG. 11*b*, and a monitor device 6, such as the monitor device as illustrated in FIG. 2. The base plate 4 of FIG. 40 is substantially similar to the base plate 4 as illustrated in relation to FIG. 39.

The monitor device 6 as shown in FIG. 40 comprises an opening 424, for example in a rim surface of the monitor device 6. The opening 424 is configured to receive the coupling part 210 of the base plate 4. The monitor device 6 is configured to engage with the coupling part 210 of the base plate 4 by a motion, such as a linear motion, in the engagement direction 412 of the monitor device 6 relative to the base plate 4. The monitor device 6 is configured to disengage with the coupling part 210 of the base plate 4 by a motion, such as a linear motion, in the disengagement direction 413 of the monitor device 6 relative to the base plate 4.

The plurality of terminals 212 of the base plate is provided on the coupling part 210. The plurality of terminals of the monitor device 6 may be provided inside the opening 424, such as to connect to the plurality of terminals 212 of the base plate 4 when the monitor device 6 is coupled to the base plate 4.

The monitor device 6 comprises a locking mechanism configured to lock the monitor device 6 in a coupled position with the base plate 4. The locking mechanism of the monitor device 6 is configured to cooperate with the locking section 428 of the base plate 4. The locking section 428 in the illustrated example comprises a hole 428*a* extending through the coupling part 210. For example, the locking mechanism of the monitor device 6 may comprise a locking component, for example a pin, positioned inside the opening 424 and being configured to protrude through the hole 428*a*. As opposed to the example shown in FIG. 39, the locking section 428 of FIG. 40 does not comprise the indentations 428*b*, 428*c*. However, it is noted that the locking section 428 of FIG. 39 may optionally comprise the indentations 428*b*, 428*c*, as shown in FIG. 39.

The locking mechanism comprises a locking element 430 comprising a first button 430*a*. The locking element 430, such as the first button 430*a*, further comprises a locking element protrusion 431. The first button 430*a* is deflectable in a first direction 432 and the locking element protrusion 431 is configured for the user to pull/push the first button 430*a* in a second direction 433, opposite the first direction 432. The locking element 430 may be configured for a rotational movement about an axis substantially perpendicular to the engagement direction 412 and/or the disengagement direction 413. The axis of rotation of the locking element 430 may be substantially parallel to a base plate plane of the base plate 4.

The locking element 430 is configured to unlock and/or lock the locking mechanism, such as to unlock the monitor device 6 in the coupled position with the base plate 4 and/or to lock the monitor device 6 in the coupled position with the base plate 4. For example, the user may push the first button 430*a* in the first direction, for example to lock the locking mechanism, and the user may subsequently push/pull the first button 430*a* by the locking element protrusion 431 in the second direction, for example to unlock the locking mechanism.

Hence, the user may move the monitor device 6 in the engagement direction 412, such that the coupling part 210 is received in the opening 424, and hereafter, the user may push the first button 430*a* in the first direction to lock the locking mechanism, and the monitor device is locked, such as retained, in the coupled position with the base plate 4. Subsequently, in order to remove the monitor device 6 from the base plate 4, the user may push/pull the locking element protrusion 431 in the second direction 433 to unlock the locking mechanism, and the user may disengage the monitor device 6 from the base plate 4 by moving the monitor device 6 in the disengagement direction 413.

The locking element 430 may be configured to be positioned in a plurality of predefined positions, for example including a locked position and a first unlocked position. The predefined positions may be positions of the locking element 430 where a greater force is needed to change the position of the locking element 430. The plurality of predefined positions may include a second unlocked position, such as a cleaning position, where the locking element 430 is opened to allow cleaning of the interior of the opening 424. The locking element may be brought from the locked position to the first unlocked position by movement in the second direction 433, for example by an angular movement of the locking element 430 of between 10-75 degrees. The locking element may be brought from the first unlocked position to the second unlocked position by (further) movement in the second direction 433, for example by an angular movement of the locking element 430 of between 90-170 degrees. The locking element 430 may be brought from the second unlocked position to the first unlocked position by movement in the first direction 432, for example by an angular movement of the locking element 430 of between 90-170 degrees. The locking element 430 may be brought from the first unlocked position to the locked position by (further) movement in the first direction 432, for example by an angular movement of the locking element 430 of between 10-75 degrees. An angular distance between the locked position to the second unlocked position may be between 100-200 degrees.

Figure 42:
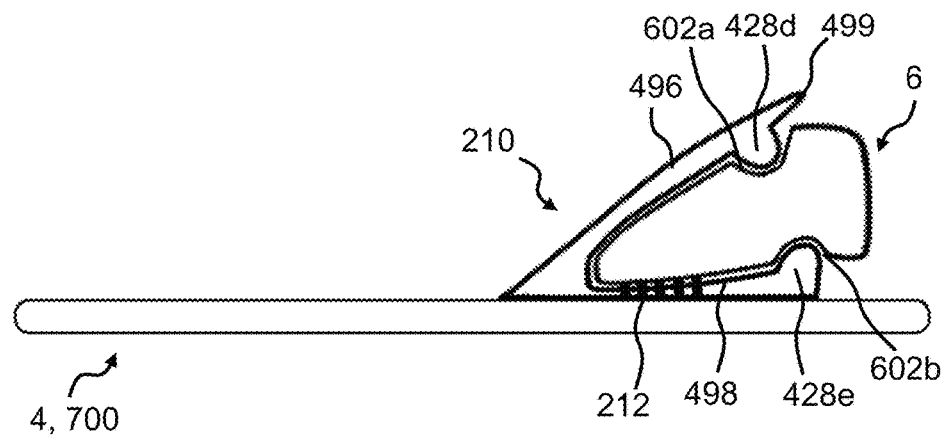

FIGS. 41 and 42 schematically illustrates an exemplary base plate 4 and/or an exemplary sensor assembly part 700, such as the base plate and/or sensor assembly part as illustrated in FIG. 11*a* or FIG. 11*b*. The base plate plane P is illustrated by a dotted line. The base plate plane P is parallel to the extent of the base plate 4.

The base plate 4 and/or sensor assembly part 700 comprises a coupling part 210 comprising a first coupling part section 496 and a second coupling part section 498. The coupling part 210 is configured to receive at least a part of the monitor device 6 between the first coupling part section 496 and the second coupling part section 498, as illustrated in FIG. 28. The first coupling part section 496 and the second coupling part section 498 are biased towards each other, for example by the elastic property of the coupling part 210 and/or by spring means. In the illustrated example, the first coupling part section 496 is deflectable from the second coupling part section 498. The first coupling part section 496 comprises a lever 499 to allow a user to bend the first coupling part section 496 away from the second coupling part section 498, such as to release the monitor device 6 from the coupling part 210. The exemplary monitor device 6, configured to engage with the illustrated exemplary coupling part 210, is wedge shaped to allow easy insertion between the first coupling part section 496 and the second coupling part section 498.

The coupling part 210 comprises a locking section 428 comprising a first protrusion 428*d* protruding from the first coupling part section 496 and a second protrusion 428*e* protruding from the second coupling part section 498. The monitor device 6 may comprise corresponding indents 602, such as a first indent 602*a* to receive the first protrusion 428*d* and a second indent 602*b* to receive the second protrusion 428*e*.

The plurality of terminals 212 of the base plate 4 and/or sensor assembly part 700 is provided in coupling part 210, such as between the first coupling part section 496 and the second coupling part section 498.

Figure 43:
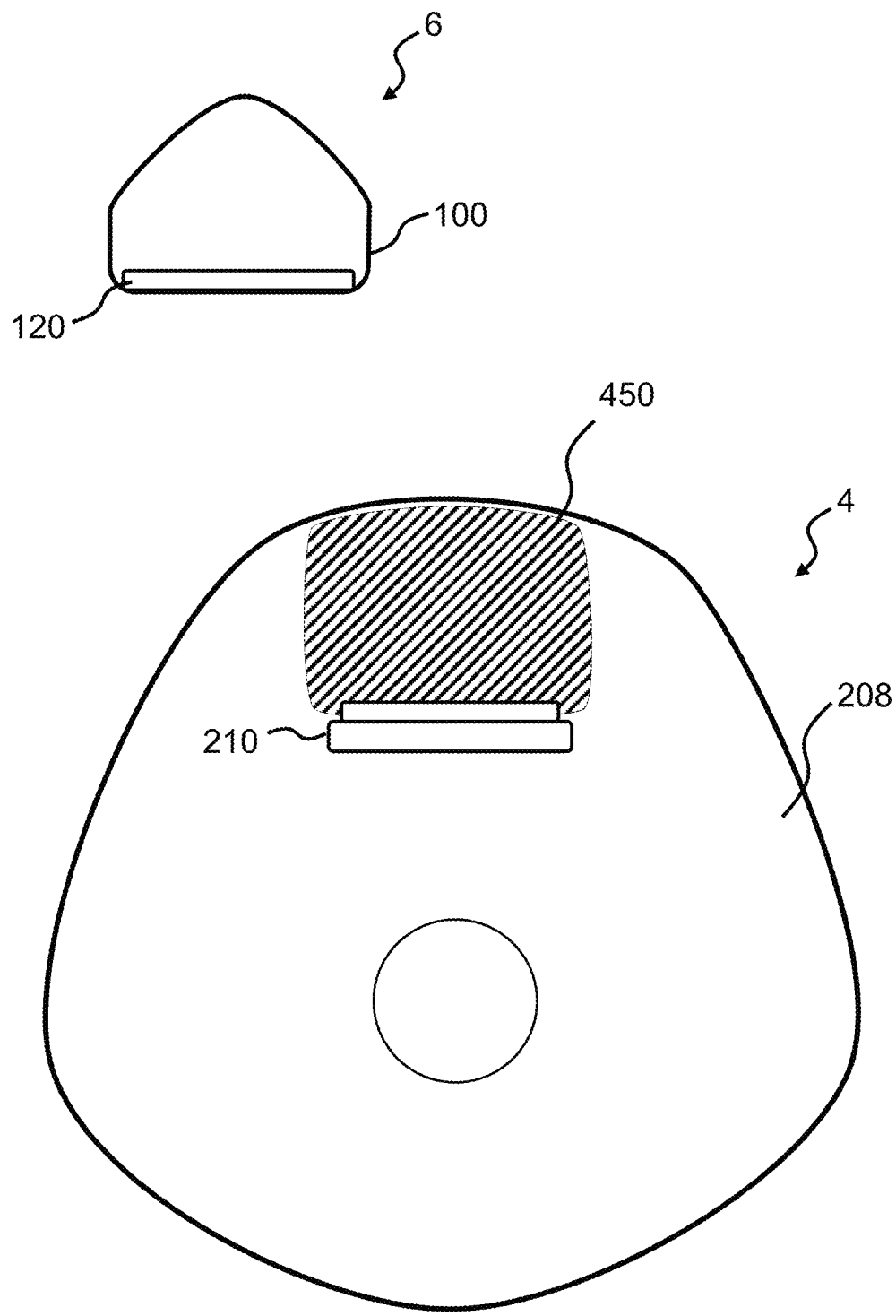

FIG. 43 schematically illustrates an exemplary base plate 4, such as a base plate 4 as illustrated in previous figures, such as in FIG. 11*a* or 11*b*, or FIGS. 15-20. The base plate 4 comprises a top layer 208, a first adhesive layer 200 (see for example FIGS. 11*a* and 11*b*) and an electrode assembly 204 (see for example FIGS. 11*a* and 11*b*) comprising a plurality of electrodes 216. The base plate 4 may comprise other optional layers as explained above, such as an optional second adhesive layer 204 (see for example FIGS. 11*a* and 11*b*), for example arranged between the top layer 208 and the electrode assembly 204.

FIG. 43 also shows a schematic illustration of an exemplary monitor device 6, such as a monitor device 6 as illustrated in FIG. 2, for connecting to the base plate 4. The monitor device 6 comprises a monitor device housing 100, electronic circuitry (see for example FIG. 2); and an appliance interface 102 (see for example FIG. 2). The appliance interface is configured for connecting the monitor device 6 to the base plate 4. The appliance interface comprises a plurality of terminals 108, 110, 112, 114, 116, 118 (see for example FIG. 2) for connecting with a plurality of electrodes 216 of the base plate 4, such as through a plurality of terminals 212 of the base plate 4. The appliance interface comprises a monitor device coupling part 120 configured for coupling, such as mechanical coupling, between the monitor device 6 and the base plate 4.

The base plate 4 further comprises a monitor interface configured for connecting the base plate 4 to a monitor device 6. The monitor interface comprising a plurality of terminals electrically connected to the plurality of electrodes. The plurality of terminals of the base plate is configured to connect with respective terminals of the monitor device. The monitor interface comprises a coupling part 210 configured for coupling between the monitor device and the base plate 4. The coupling part 210 of the base plate 4 and the coupling part 120 of the monitor device 6 is configured to be coupled, such as mechanically coupled, i.e. the coupling parts 120, 210 are compatible coupling parts.

The coupling part 210 of the base plate 4 is positioned distal to the top layer 208. The coupling part 210 of the base plate 4 is positioned such that when the monitor device 6 is coupled to the base plate 4 the top layer 208 is disposed between the monitor device 6 and the skin of the user. Furthermore, the monitor device 6 is configured, for example shaped and/or sized, such that when the monitor device 6 is coupled to the base plate 4 the top layer 208 of the base plate 4 is disposed between the monitor device 6 and the skin of the user.

For example, as illustrated, the coupling part 210 of the base plate is positioned to form a first area 450 between the coupling part 210 and an edge of the top layer 208. The coupling part 210 of the base plate is positioned such that the first area 450 is greater than a cross sectional area of the monitor device 6, such as the largest cross-sectional area of the monitor device 6, i.e. the cross-sectional area measured in a plane of the monitor device 6 wherein the monitor device 6 expands the largest area. The first area 450 is substantially rectangular. However, subject to the shape of the base plate, the first area 450 may be substantially triangular, pentagonal or similar. The monitor device 6 may be shaped and/or sized to have a cross sectional area smaller than the first area, as also illustrated.

Figure 44:
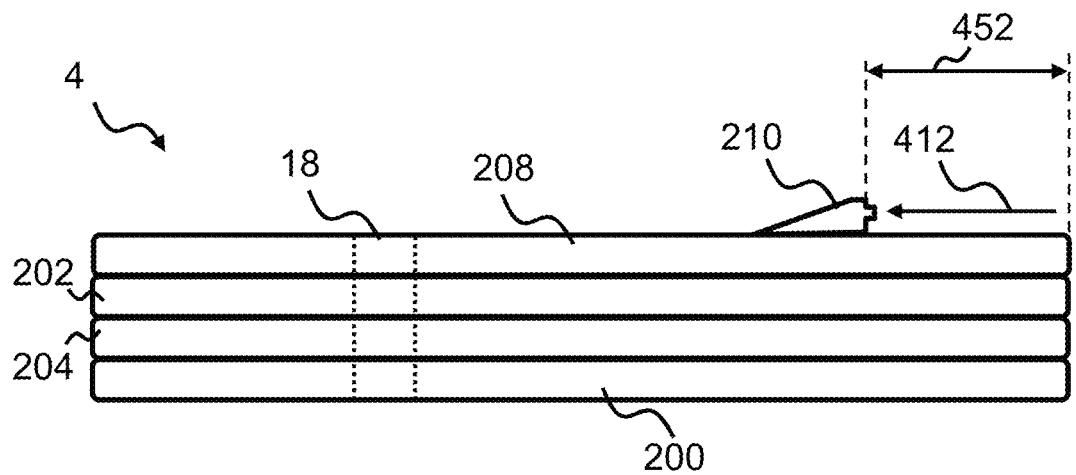
FIG. 44 shows a schematic representation of cross section of an exemplary base plate.

FIG. 44 shows a schematic representation of cross section of an exemplary base plate 4, such as the base plate 4 as illustrated in FIG. 38. The base plate 4 comprises a top layer 208, a first adhesive layer 200 and an electrode assembly 204 comprising a plurality of electrodes 216 (see for example FIGS. 11a and 11b). The base plate 4 may comprise other optional layers as explained above. For example, the base plate 4 comprises an optional second adhesive layer 204 arranged between the top layer 208 and the electrode assembly 204.

As illustrated, the coupling part 210, may be configured such that the monitor device is received in an engagement direction 412 being substantially parallel with the base plate 4, such as substantially along the base plate 4. It is furthermore shown that the coupling part 210 is positioned at a distance 452 from the edge of the top layer 208. The distance 452 is greater than a first dimension, such as a height, of the monitor device, such that the monitor device, when coupled to the coupling part 210, is separated from the skin by the base plate 4, such as the top layer 208.

Figure 45:
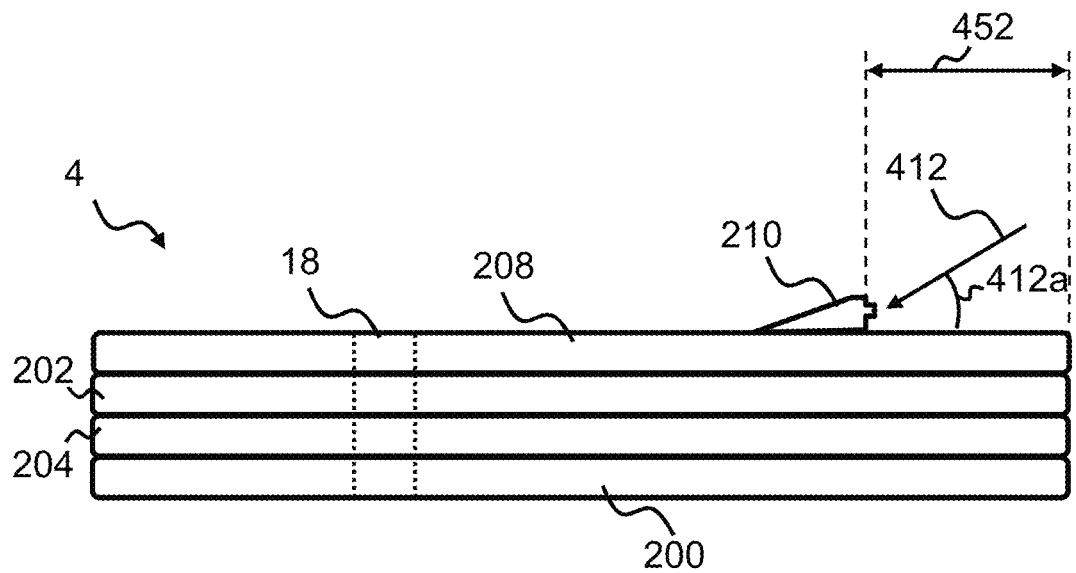
FIG. 45 shows a schematic representation of cross section of an exemplary base plate,
FIG. 46 schematically illustrates an exemplary base plate, monitor device and ostomy pouch,
FIGS. 47A-E schematically illustrates a test performed,
FIG. 48 graphically shows the results of the test performed.

FIG. 45 shows another schematic representation of cross section of an exemplary base plate 4 similar to the example of FIG. 44. However, with the difference that the engagement direction 412 is not specifically parallel to the base plate, but instead spans an engagement angle 412a with the base plate 4, such as a base plate plane defined by the base plate 4 and/or the layers 200, 202, 204, 208 of the base plate. The engagement angle 412a may be less than 45 degrees, such as between 0 and 45 degrees, in order to ease engagement and/or disengagement of the monitor device to the base plate 4.

Generally, for the above described figures, the user may apply an engagement force in the engagement directions 412 as illustrated, to couple the monitor device 6 and the base plate 4, for example by movement of the monitor device 6 in the respective engagement direction 412. Similarly, the user may apply a disengagement force in the disengagement directions 413 as illustrated, to couple the monitor device 6 and the base plate 4, for example by movement of the monitor device 6 in the respective disengagement direction 413.

Figure 46:
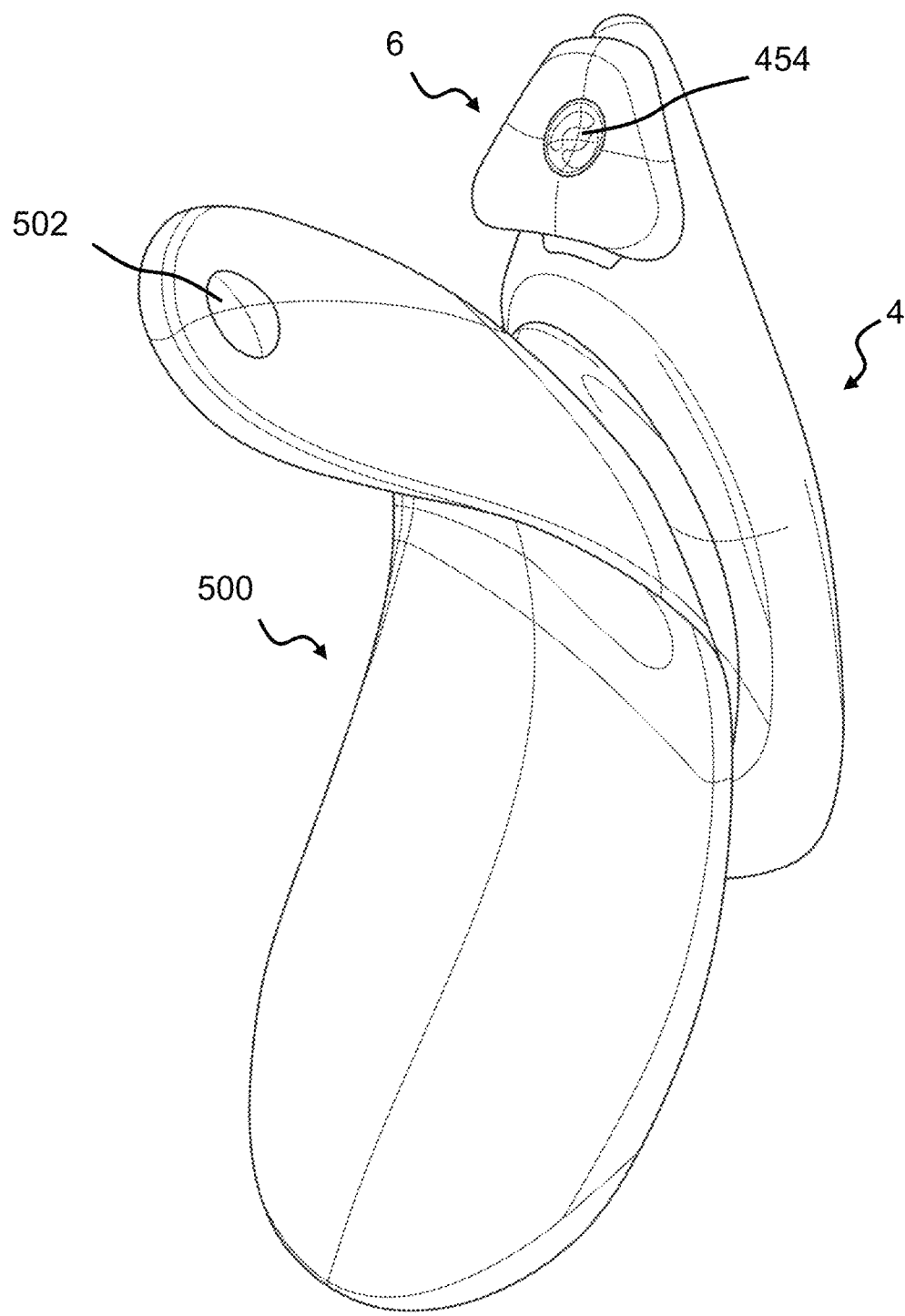

FIG. 46 schematically illustrates an exemplary base plate 4, such as the base plate as illustrated in relation to any of the previous figures, and a monitor device 6, such as a monitor device as illustrated in relation to any of the previous figures. Furthermore, FIG. 46 also schematically illustrates an exemplary ostomy pouch 500 coupled to the base plate 4.

The monitor device 6 comprises an attachment element 454. The attachment element 454 is configured to attach to the ostomy pouch 500. For example, as illustrated, the ostomy pouch 500 may comprise a retaining arrangement 502, such as a retaining arrangement 502 corresponding to the attachment element 454 of the monitor device. Thereby, the ostomy pouch 500 may be attached to the monitor device 6, for example when the monitor device 6 is coupled to the base plate 4, for example to protect and/or hide the monitor device by the ostomy pouch. In an alternative exemplary base plate, the attachment element 454 may be provided on the base plate 4, such as to attach the ostomy pouch, such as the retaining arrangement 502 of the ostomy pouch, to the base plate in order to hide and/or cover the monitor device 6 by the ostomy pouch.

The attachment element 454 and the retaining arrangement 502 may be Velcro elements or magnetic elements and/or magnet material. Alternatively, the attachment element 454 of the monitor device 6 or base plate 4 may be in the form of a clamp configured to clamp to an edge of the ostomy pouch. Alternatively, the attachment element 454 of the monitor device 6 or base plate 4 may be in the form of a slit configured to receive an edge of the ostomy pouch.

FIGS. 47A-47E show schematic illustrations of a test performed, when applying a force in the engagement direction towards a substrate resembling the properties of a human belly.

The test was performed with a texture analysing apparatus 1020 called "TXplus Texture Analyzer" having a loadcell of 50 N in compression mode. The test was performed in ambient temperature, approx. 20 degrees. The texture analysing apparatus 1020 was programmed to perform a force of 4 N at a speed of 5 mm/s. The pressure test was performed in angle intervals of 10 degrees from 90 to 10 degrees, wherein the angle was defined as the angle between the engagement direction of the force applied and a reference plane defined by the upper planar surface of the substrate.

The pressure test was performed on a substrate 1000 of silicone gel with shore A48, which corresponds to the average shore of an abdomen at the peristomal area. An adhesive base plate 1002 of the type SenSura Mio® 1-Piece Drainable Pouch from Coloplast A/S was adhered to an upper surface 1004 of the silicone gel substrate 1000.

A coupling part 1006 was positioned on top of the base plate 1002 at a distance of approx. 15 mm from the periphery 1008 of the base plate. The coupling part comprised a C-shaped base 1010, which was mounted to the base plate with a double-sided adhesive. The C-shaped base 1010 comprised an area of approximately 88 mm2 (dimensions; arm length 8 mm, body length 19 mm and width 2.5 mm). The coupling part 1006 comprised a flange 1012 flexibly connected to the C-shaped base 1010 allowing the plane defined by the flange 1012 to be positioned in an angle from 0 to 90 degrees relative to the C-shaped base 1010 and the base plate. The flange 1012 of the coupling part had a thickness of 1 mm, a width of 16 mm and height of 16 mm. The C-shaped base was mounted in an orientation having the arms extending in a direction towards the periphery 1008 of the base plate and the longitudinal body portion of the C-shaped part oriented towards the central part 1014 of the base plate 1002. Additionally, the flange 1012 was oriented with respect to the texture analysing apparatus such that when the apparatus applied a force to the flange, in an angled position, the force had a direction inwards towards the central part 1014 of the base plate 1002.

A fixture was connected to the texture analysing apparatus 1020. The fixture had a narrow groove, which was configured to engage with the flange 1012 of the coupling part to fixate and control the angle of the flange 1012 of the coupling part 1006 relative to the reference plane defined by the upper surface 1004 of the substrate 1000.

Figure 47A:
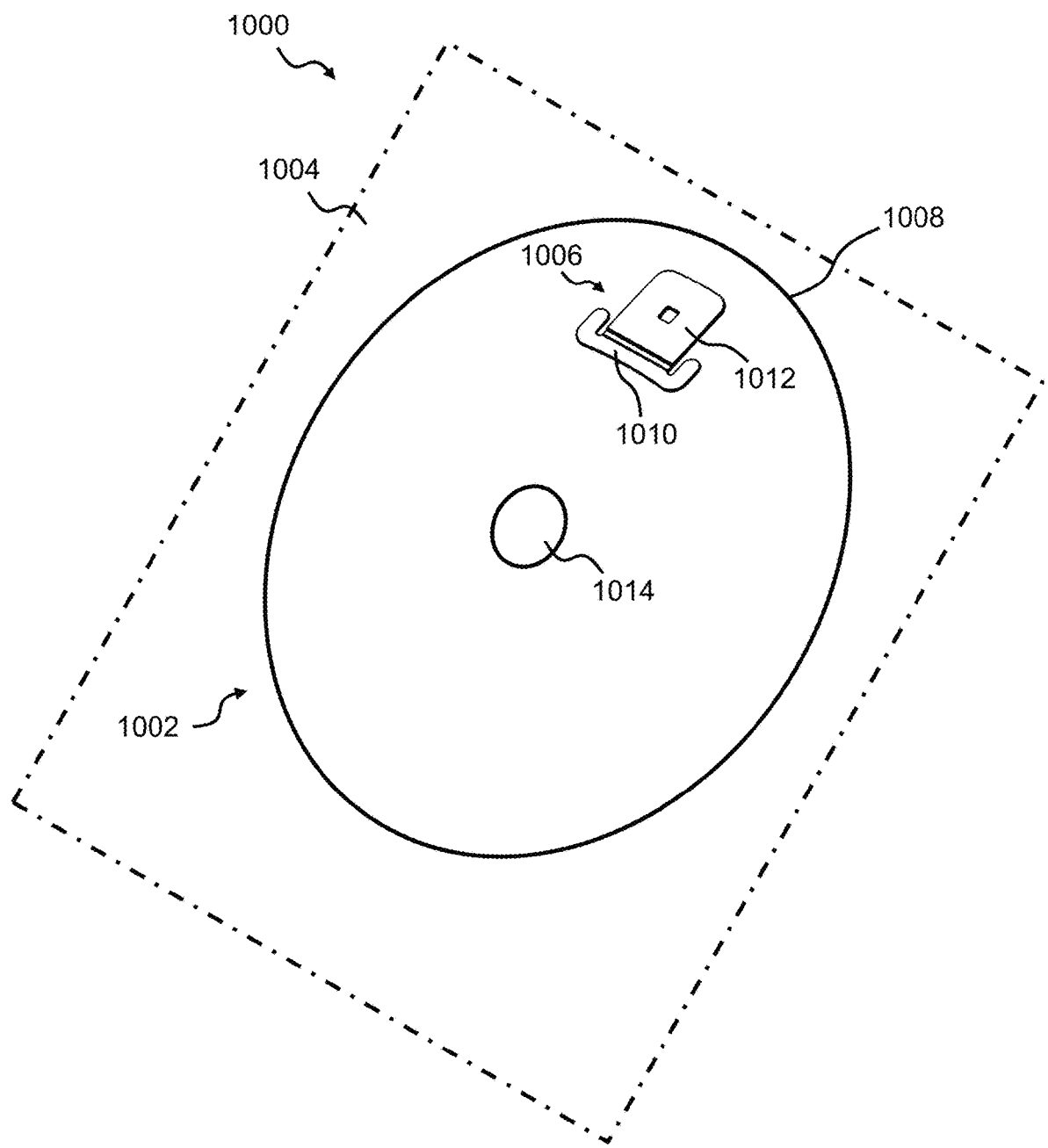
Figure 47B:
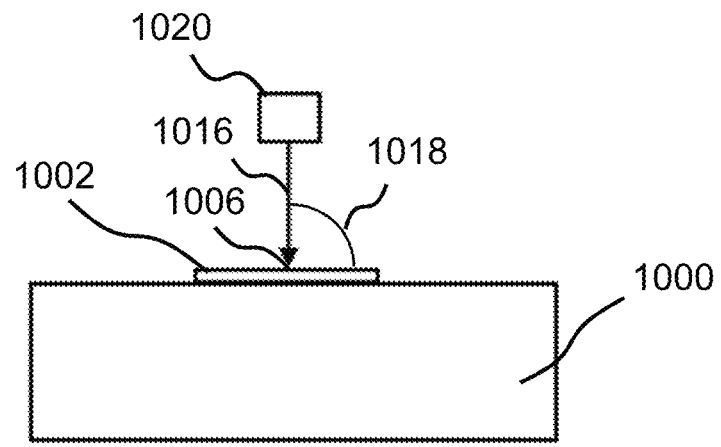
Figure 47C:
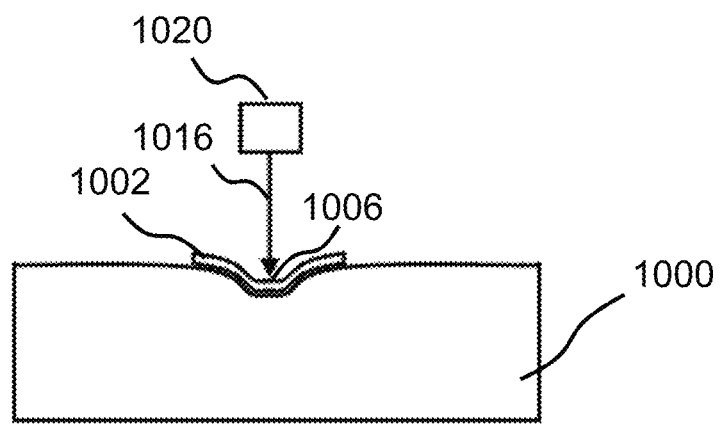
Figure 47D:
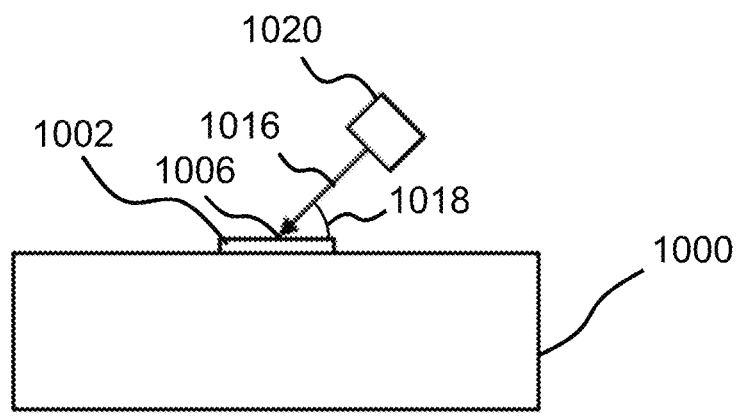
Figure 47E:
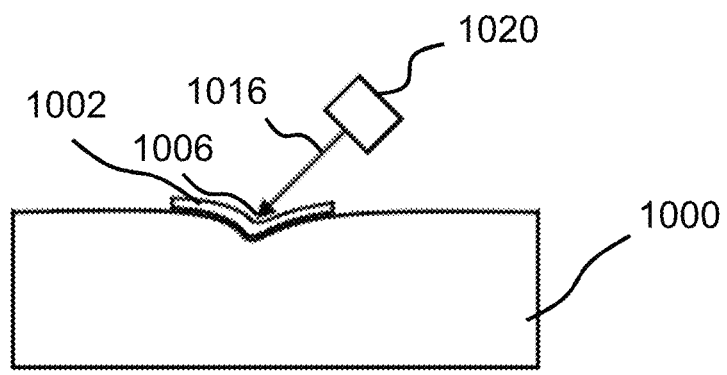

As schematically illustrated in FIGS. 47B-47E, the coupling part 1006 was exposed to the force 1016 applied by the texture analysing apparatus 1020, at angles 1018 ranging from 90 to 10 degrees, i.e. from perpendicular to the reference plane to almost parallel to the reference plane. For each of the angles, the depth of the depression into the base plate and substrate, along the direction of the force 1016, as illustrated in FIGS. 47C and 47E, caused by the force 1016 applied by the texture analysing apparatus 1020, was measured.

Figure 48:
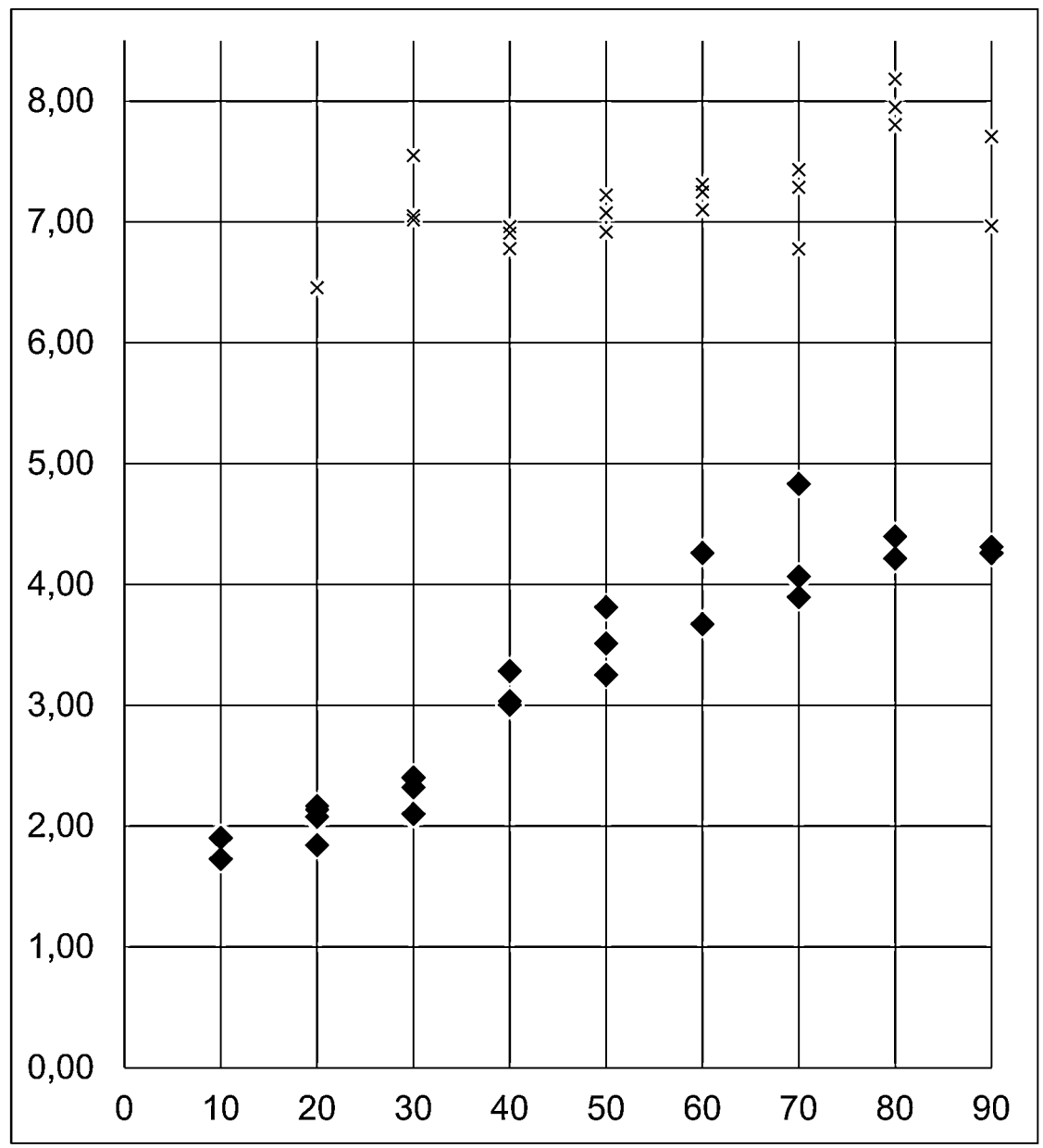

Results of the tests are graphically shown as diamonds in FIG. 48 and are furthermore tabulated below: The depth of the depression into the base plate and substrate, along the direction of the force, has been converted to a depth perpendicular to the substrate surface.

| Angle relative to reference plane | Depth in mm In direction of force applied | Depth in mm Perpendicular to substrate surface |
|---|---|---|
| 90 | 4.26 | 4.26 |
| 90 | 4.31 | 4.31 |
| 80 | 4.40 | 4.33 |
| 80 | 4.21 | 4.15 |
| 70 | 3.89 | 3.66 |
| 70 | 4.83 | 4.54 |
| 70 | 4.07 | 3.83 |
| 60 | 4.26 | 3.20 |
| 60 | 3.67 | 3.18 |
| 50 | 3.81 | 2.92 |
| 50 | 3.26 | 2.50 |
| 50 | 3.52 | 2.70 |
| 40 | 3.28 | 2.11 |
| 40 | 3.04 | 1.95 |
| 40 | 3.01 | 1.93 |
| 30 | 2.11 | 1.06 |
| 30 | 2.42 | 1.21 |
| 30 | 2.33 | 1.16 |
| 30 | 2.41 | 1.20 |
| 20 | 1.86 | 0.63 |
| 20 | 2.16 | 0.74 |
| 20 | 2.17 | 0.74 |
| 20 | 2.09 | 0.72 |
| 10 | 1.75 | 0.30 |
| 10 | 1.95 | 0.34 |

As shown by the results of the test, the user would displace the coupling point into the abdomen at different values depending on the angle of the applied force used to engage the monitor device with the base plate. Thus, the test significantly shows that it will be both easier and more comfortable to attach the monitor device with a force being more parallel than perpendicular to the abdomen, i.e. more parallel than perpendicular to the base plate plane. Hence, the angle of the engagement force should preferably be less than 45 degrees, or even more preferably less than 40 degrees, such as less than 30 degrees, such as less than 20 degrees.

The tests performed showed that it may be advantageous to provide coupling by utilizing forces more in a direction parallel than perpendicular to the skin surface, i.e. more parallel than perpendicular to a base plate plane P.

Additionally, the table illustrates that the depth of indent in an axial direction, approximately perpendicular to the skin of a user, is reduced concurrently with lowering the angle relative to the reference plane, i.e. with respect to the base plate plane/the user's abdomen. Furthermore, the test shows a halving of indent depth when the degrees were lowered from 90 degrees to 40 degrees, and the indent depth was further halved at 30 degrees.

Hereby, a radial direction of the applied force, for engagement between the complementary shaped coupling parts of the base plate and the monitor device, is preferred over a force in axial direction.

The base plate distributed more evenly the mechanical stress from a force required for coupling a monitor device to the base plate, thus limiting uncomfortably pressure into the abdomen of the user.

Furthermore, the test was also performed without the base plate. Thus, the test assesses the pressure resistance of the substrate alone. The results of this test are shown by crosses in FIG. 48 and are furthermore tabulated below:

| Angle relative to reference plane | Depth in mm |
|---|---|
| 90 | 6.97 |
| 90 | 7.71 |
| 80 | 8.18 |
| 80 | 7.81 |
| 80 | 7.95 |
| 70 | 6.78 |
| 70 | 7.29 |
| 70 | 7.43 |
| 60 | 7.31 |
| 60 | 7.10 |
| 60 | 7.25 |
| 50 | 7.22 |
| 50 | 6.92 |
| 50 | 7.08 |
| 40 | 6.96 |
| 40 | 6.91 |
| 40 | 6.78 |
| 30 | 7.02 |
| 30 | 7.05 |

-continued

| Angle relative to reference plane | Depth in mm |
|---|---|
| 30 | 7.55 |
| 20 | 6.46 |

As seen, the depth reached before meeting a sufficient counter force when not having applied a base plate seems to be approximately constant for all angles of engagement. Thus, the different results in depth measured, as cited in the first table, relates primarily to the properties of the base plate of the ostomy appliance system.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The use of the terms "first", "second", "third" and "fourth", "primary", "secondary", "tertiary" etc. does not imply any particular order but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Embodiments, and features of the various exemplary embodiments described in this application, may be combined with each other ("mixed and matched"), unless specifically noted otherwise.

Embodiments of the present disclose are set out in the following items:

1. A base plate for an ostomy appliance, the base plate (4) comprising:
   a top layer (208) defining a base plate plane;
   a first adhesive layer (200) adapted to adhere the base plate (4) to peristomal skin of a user;
   an electrode assembly (204); and
   a monitor interface (207) configured to electronically connect with the electrode assembly (204), where the monitor interface (207) comprises a coupling part (210) configured to form a releasably mechanically and/or electronically coupling between the base plate (4) and a monitor device (6);
   the coupling part (210) is configured to engage and/or disengage with the monitor device (6) allowing the monitor device (6) to be coupled to the base plate by a motion in a direction corresponding to an acute angle of 45 degrees or less relative to the base plate plane.

2. A base plate according to the preceding item, wherein the base plate comprising a locking mechanism configured to lock the monitor device in a coupled position with the base plate.

3. A base plate according to any of the preceding items, wherein the locking mechanism is biased towards locking of the locking mechanism.

4. A base plate according to any of the preceding items, wherein the base plate comprising a locking element configured to unlock and/or lock the locking mechanism upon user interaction with the locking element.

5. A base plate according to any of the preceding items, wherein the locking element comprises a first button being deflectable in a first direction, wherein the first direction is substantially parallel to the engagement direction.

6. A base plate according to any of the preceding items, wherein the locking element comprises a first button and a second button, the first button being deflectable in a first direction and the second button being deflectable in a second direction, wherein the first direction is substantially opposite the second direction.

7. A base plate according to any of the preceding items, wherein the first direction and the second direction are substantially perpendicular to the engagement direction.

8. A base plate according to any of the preceding items, wherein the locking element comprises a slider being slidable in a first slider direction, and wherein the slider is spring loaded and biased towards a second slider direction, wherein the first slider direction is opposite the second slider direction.

9. A base plate according to any of the preceding items, wherein the first slider direction and the second slider direction are substantially perpendicular to the engagement direction.

Exemplary embodiments of the present disclosure are set out in the following first items:

1. A base plate for an ostomy system, the base plate comprising:
   a monitor interface including:
      a plurality of terminals configured to electrically couple the base plate to a monitor device of the ostomy system, and
      a coupling part configured to releasably and structurally couple the base plate to the monitor device.

2. The base plate of first item 1, wherein the coupling part comprises a rim and a base.

3. The base plate of first item 2, wherein the rim extends distally and has a longitudinal axis.

4. The base plate of any of the preceding first items, wherein the coupling part comprises an alignment member configured to guide the monitor device from an attachment position to a secured position.

5. The base plate of first item 4, wherein the alignment member comprises a coupling thread.

6. The base plate of first item 5, wherein the coupling threads is on an inner surface of the rim.

7. The base plate of first item 5, wherein the coupling threads is on an outer surface of the rim.

8. The base plate of any of first items 5-7, wherein the coupling threads comprises one or more channels defined by one or more protrusions.

9. The base plate of first item 8, wherein each of the one or more channels has an entry opening near a distal end of the rim and configured to receive the monitor device.

10. The base plate of any of first items 8-9, wherein the one or more channels extend toward the base of the coupling part circumferentially around the rim.

11. The base plate of any of first items 8-10, wherein each of the one or more channels has a stop near the base.

12. The base plate of any of the preceding first items further comprises one or more waterproofing elements.

13. The base plate of first item 12, wherein the one or more waterproofing elements comprises at least one of a ring or a conical region of the coupling part.

14. The base plate of first item 13, wherein the ring comprises at least one of rubber, polyurethane, or silicone material.

15. The base plate first item 13, wherein the conical region is compliant.

16. The base plate of first item 15, wherein the conical region comprises at least one of rubber, polyurethane, or silicone.

17. The base plate any of first items 12-16, wherein the one or more waterproofing elements are releasably attached to the base plate.

18. The base plate of any of first items 4-17, wherein the alignment member comprises a segmented channel.

19. The base plate of first item 18, wherein the segmented channel may comprise one or more longitudinal segments and/or one or more transversal segments.

20. The base plate of any of first items 4-19, wherein the alignment member comprises a variable width channel.

21. The base plate of first item 20, wherein the variable width channel comprises a wide region and a narrow region.

22. The base plate of any of first items 4-21, wherein the alignment member comprises a variable depth channel.

23. The base plate of first item 22, wherein the variable depth channel comprises a deep region and a shallow region.

24. The base plate of any of first items 4-23, wherein the alignment member comprises a pocketed channel.

25. The base plate of first item 24, wherein the pocketed channel comprises a guiding region, a pocketing region, and a pocketing element.

26. The base plate of first item 25, wherein the guiding region is separated from the pocketing region by the pocketing element.

27. The base plate of any of first item 25-26, wherein the pocketing element comprises one or more protuberances and/or a separation wall.

28. The base plate of any of first items 1-27, wherein the coupling part comprises one or more magnetic elements configured to be magnetically coupled to one or more magnetic elements of the monitor device for the ostomy system.

29. The base plate of first item 28, wherein the one or more magnetic elements are arranged symmetrically.

30. The base plate of any of first items 28-29, wherein the one or more magnetic elements are at least one of ferromagnetic, paramagnetic, diamagnetic, ferromagnetic, or antiferromagnetic.

31. A monitor device for an ostomy system, the monitor device comprising:
a first connector including:
a plurality of terminals configured to be electrically coupled to a base plate of the ostomy system, and
a coupling part configured to releasably and structurally couple the monitor device to the base plate.

32. The monitor device of first item 31, wherein the coupling part comprises a wall portion defining a recess configured to receive a coupling part of the base plate.

33. The monitor device of any of first items 31-32, wherein the coupling part comprises one or more tabs configured to engage an alignment member of the coupling part of the base plate.

34. The monitor device of any of first items 33, wherein the one or more tabs extend from the wall portion into the recess.

35. The monitor device of any of first items 33-34, wherein the one or more tabs are substantially rectangular, cylindrical, rounded, or spherical.

36. The monitor device of any of first items 31-35, further comprising an actuatable tab.

37. The monitor device of first item 36, wherein the actuatable tag is configured to protrude off from the wall portion of the coupling part and retract into the wall portion when actuated.

38. The monitor device of any of first items 36-37, wherein the actuatable tab is latched onto an actuation member.

39. The monitor device of first item 38, wherein the actuation member comprises at least one of a slider, a button, or a switch.

40. The monitor device of any of first items 36-39, wherein the actuatable tab is spring-loaded.

41. The monitor device of any of first items 31-40 further comprising one or more magnetic elements configured to be magnetically coupled to one or more magnetic elements of the base plate for the ostomy system.

42. The monitor device of first item 41, wherein the one or more magnetic elements are arranged symmetrically.

43. The monitor device of any of first items 41-42, wherein the one or more magnetic elements are at least one of ferromagnetic, paramagnetic, diamagnetic, ferromagnetic, or antiferromagnetic.

44. A method of coupling a monitor device for an ostomy system to a base plate for the ostomy system, the method comprising:
positioning a coupling part of the monitor device in alignment with a coupling part of the base plate;
engaging the two coupling parts in an attachment position; and
coupling the two coupling parts in a secured position.

45. The method of first item 44, wherein engaging the two coupling parts comprises engaging one or more tabs of the monitor device to an alignment member of the base plate.

46. The method of any of first items 44-45, wherein coupling the two coupling parts comprises rotating the monitor device substantially about a longitudinal axis of a rim of the coupling part of the base plate.

47. The method of first item 46, wherein the rotation is smaller than 180 degrees.

48. The method of any of first items 46-47, wherein the rotation is at least partly clockwise and/or at least partly counter-clockwise.

49. The method of any of first items 44-48, further comprising forming a waterproofing seal.

50. The method of first item 49, wherein forming the waterproofing seal comprises engaging one or more waterproofing elements of the monitor device with the base plate and/or engaging one or more waterproofing elements of the base plate with the monitor device.

51. The method of any of first items 44-50, wherein coupling the two coupling parts comprises pushing the monitor device translationally towards the base plate.

52. The method of any of first items 44-51, wherein coupling the two coupling parts comprises applying a pocketing force to the monitor device to deform a pocketing element of the alignment member of the base plate.

53. The method of any of first items 44-52, wherein coupling the two coupling parts comprises actuating an actuatable tab.

Exemplary embodiments of the present disclosure are set out in the following second items:

1. A base plate for an ostomy appliance, the base plate comprising:
   a top layer;
   a first adhesive layer; and
   an electrode assembly comprising a plurality of electrodes;
   a monitor interface configured for connecting the base plate to a monitor device, the monitor interface comprising a plurality of terminals electrically connected to the plurality of electrodes and configured to connect with respective terminals of the monitor device, and the monitor interface comprising a coupling part configured for coupling between the monitor device and the base plate,
wherein the coupling part comprises a loop element or a flexible element configured to form the loop element, the loop element forming a conduit between a first opening and a second opening, the coupling part being configured to receive at least a part of the monitor device through the first opening and/or the second opening.

2. Base plate according to second item 1, wherein the loop element comprises a first loop end connected to a distal side of the top layer and/or a distal side of the first adhesive layer.

3. Base plate according to any of the preceding second items, wherein the plurality of terminals is provided on an inside surface of the loop element.

4. Base plate according to any of second items 1-2, wherein the plurality of terminals is provided on an outside surface of the loop element.

5. Base plate according to any of the preceding second items, wherein a first top layer part of the top layer and a first electrode assembly part of the electrode assembly forms the loop element.

6. Base plate according to any of the preceding second items, wherein the coupling part is configured to receive the at least part of the monitor device by a linear motion in an engagement direction of the monitor device relative to the base plate.

7. Base plate according to second item 6, wherein the top layer and first adhesive layer are substantially planar and extending in a base plate plane, and wherein the engagement direction is substantially parallel to the base plate plane.

8. Base plate according to any of the preceding second items, wherein the electrode assembly is provided between the top layer and the first adhesive layer, and wherein a distal side of the electrode assembly is facing the top layer, and wherein a proximal side of the electrode assembly is facing the first adhesive layer.

9. Base plate according to any of the preceding second items, wherein the electrode assembly comprises a support layer, and wherein the plurality of electrodes is provided on a proximal side of the support layer.

10. A monitor device for connecting to a base plate of an ostomy appliance, the monitor device comprising:
    a monitor device housing;
    electronic circuitry; and
    an appliance interface configured for connecting the monitor device to the base plate, the appliance interface comprises a plurality of terminals for connecting with a plurality of electrodes of the base plate, the appliance interface comprises a monitor device coupling part configured for coupling between the monitor device and the base plate;
wherein the monitor device coupling part comprises a first clip element forming a first slit configured to receive an element of the base plate.

11. Monitor device according to second item 10, wherein the first slit is formed between the first clip element and the monitor device housing.

12. Monitor device according to any of second items 10-11, wherein the plurality of terminals is provided inside the first slit.

13. Monitor device according to any of second items 10-12, wherein the plurality of terminals is provided on the first clip element.

14. Monitor device according to any of second items 10-12, wherein the plurality of terminals is provided on the monitor device housing.

15. Monitor device according to any of second items 10-14, wherein the monitor device coupling part is configured to engage with the base plate by a linear motion in an engagement direction of the monitor device relative to the base plate.

Exemplary embodiments of the present disclosure are set out in the following third items:

1. A base plate for an ostomy appliance, the base plate comprising:
   a top layer;
   a first adhesive layer;
   an electrode assembly comprising a plurality of electrodes; and
   a monitor interface configured for connecting the base plate to a monitor device, the monitor interface comprising a plurality of terminals electrically connected to the plurality of electrodes and configured to connect with respective terminals of the monitor device, and the monitor interface comprising a coupling part configured for coupling between the monitor device and the base plate,
wherein the coupling part is positioned such that when the monitor device is coupled to the base plate the top layer is disposed between the monitor device and the skin of the user.

2. Base plate according to third item 1, wherein the coupling part is positioned distal to the top layer.

3. Base plate according to any of the preceding third items, wherein the coupling part is positioned to form a first area between the coupling part and an edge of the top layer, and the first area is greater than a cross sectional area of the monitor device.

4. Base plate according to third item 3, wherein the first area is substantially triangular or substantially rectangular.

5. Base plate according to any of the preceding third items, wherein the coupling part is configured to engage with the monitor device by a linear motion in an engagement direction of the monitor device relative to the base plate.

6. Base plate according to third item 5, wherein the top layer and first adhesive layer are substantially planar and extending in a base plate plane, and wherein the engagement direction is substantially parallel to the base plate plane.

7. Base plate according to any of third items 5-6, wherein the engagement direction is towards a stomal opening of the base plate.

8. Base plate according to any of the preceding third items comprising a locking mechanism configured to lock the monitor device in a coupled position with the base plate.

9. Base plate according to third item 8, wherein the locking mechanism is biased towards locking of the locking mechanism.

10. Base plate according to any of third items 8-9 comprising a locking element configured to unlock and/or lock the locking mechanism upon user interaction with the locking element.

11. Base plate according to third item 10 as dependent on third item 5, wherein the locking element comprises a first button being deflectable in a first direction, wherein the first direction is substantially parallel to the engagement direction.

12. Base plate according to third item 10, wherein the locking element comprises a first button and a second button, the first button being deflectable in a first direction and the second button being deflectable in a second direction, wherein the first direction is substantially opposite the second direction.

13. Base plate according to third item 12 as dependent on third item 5, wherein the first direction and the second direction are substantially perpendicular to the engagement direction.

14. Base plate according to any of third items 10-13, wherein the locking element comprises a slider being slidable in a first slider direction, and wherein the slider is spring loaded and biased towards a second slider direction, wherein the first slider direction is opposite the second slider direction.

15. Base plate according to third item 14 as dependent on third item 5, wherein the first slider direction and the second slider direction are substantially perpendicular to the engagement direction.

16. Base plate according to any of the preceding third items, wherein the coupling part forms a USB type port.

17. Base plate according to any of the preceding third items comprising an attachment element, the attachment element being configured to attach to an ostomy pouch of the ostomy appliance.

18. Base plate according to third item 17, wherein the attachment element is in the form of a clamp configured to clamp to an edge of the ostomy pouch.

19. Base plate according to third item 17, wherein the attachment element is in the form of a Velcro element configured to attach to an opposing Velcro element of the ostomy pouch.

20. Base plate according to third item 17, wherein the attachment element is in the form of a magnetic material configured to attach to an opposing magnetic material of the ostomy pouch.

21. A monitor device for connecting to a base plate of an ostomy appliance, the monitor device comprising:
  a monitor device housing;
  electronic circuitry; and
  an appliance interface configured for connecting the monitor device to the base plate, the appliance interface comprises a plurality of terminals for connecting with a plurality of electrodes of the base plate, the appliance interface comprises a monitor device coupling part configured for coupling between the monitor device and the base plate;
wherein the monitor device is configured such that when the monitor device is coupled to the base plate a top layer of the base plate is disposed between the monitor device and the skin of the user.

22. Monitor device according to third item 21, wherein the monitor device is shaped to have a cross sectional area smaller than a first area of the base plate.

23. Monitor device according to any of third items 21-22, wherein the monitor device coupling part is configured to engage with the base plate by a linear motion in an engagement direction of the monitor device relative to the base plate.

24. Monitor device according to any of third items 21-23 comprising a locking mechanism configured to lock the monitor device in a coupled position with the base plate.

25. Monitor device according to third item 24, wherein the locking mechanism is biased towards locking of the locking mechanism.

26. Monitor device according to any of third items 24-25 comprising a locking element configured to unlock or lock the locking mechanism upon user interaction with the locking element.

27. Monitor device according to third item 26 as dependent on third item 23, wherein the locking element comprises a first button being deflectable in a first direction, wherein the first direction is substantially parallel to the engagement direction.

28. Monitor device according to third item 27, wherein the locking element comprises a first button and a second button, the first button being deflectable in a first direction and the second button being deflectable in a second direction, wherein the first direction is substantially opposite the second direction.

29. Monitor device according to third item 28 as dependent on third item 23, wherein the first direction and the second direction are substantially perpendicular to the engagement direction.

30. Monitor device according to any of third items 26-29, wherein the locking element comprises a slider being slidable in a first slider direction, and wherein the slider is spring loaded and biased towards a second slider direction, wherein the first slider direction is opposite the second slider direction.

31. Monitor device according to third item 30 as dependent on third item 23, wherein the first slider direction and the second slider direction are substantially perpendicular to the engagement direction.

32. Monitor device according to any of third items 21-31, wherein the monitor device coupling part forms a USB type plug.

33. Monitor device according to any of third items 21-32, wherein the monitor device comprises an attachment element being configured to attach to an ostomy pouch of the ostomy appliance.

34. Monitor device according to third item 33, wherein the attachment element is in the form of a Velcro element configured to attach to an opposing Velcro element of the ostomy pouch.

35. Monitor device according to third item 33, wherein the attachment element is in the form of a magnetic material configured to attach to an opposing magnetic material of the ostomy pouch.

36. Ostomy system comprising a base plate according to any of third items 1-20 and a monitor device according to any of third items 21-35.

Exemplary embodiments of the present disclosure are set out in the following fourth items:

1. A base plate for an ostomy appliance, the base plate comprising:
  a top layer;
  a first adhesive layer;
  an electrode assembly comprising a plurality of electrodes; and
  a monitor interface configured for connecting the base plate to a monitor device, the monitor interface comprising a plurality of terminals electrically connected to the plurality of electrodes and configured to connect with respective terminals of the monitor device and the monitor interface comprising a coupling part configured for coupling between the monitor device and the base plate,
wherein the plurality of terminals is provided on the coupling part, and wherein the coupling part comprises a locking section configured to lock the monitor device in a coupled position with the base plate.

2. Base plate according to fourth item 1, wherein the locking section comprises a hole extending through the coupling part.

3. Base plate according to any of the preceding fourth items, wherein the locking section comprises a protrusion protruding from a surface of the coupling part.

4. Base plate according to any of the preceding fourth items, wherein the locking section comprises an indent of an edge of the coupling part and/or a recess in a surface of the coupling part.

5. Base plate according to any of the preceding fourth items, wherein the coupling part comprises a first surface and a second surface, the second surface being opposite the first surface, the second surface facing the top layer.

6. Base plate according to fourth item 5, wherein the plurality of terminals is provided on the second surface of the coupling part.

7. Base plate according to any of fourth items 5-6, wherein the second surface of the coupling part and the top layer are separated to allow at least a part of the monitor device to be positioned between the second surface of the coupling part and the top layer when the monitor device is connected to the base plate.

8. Base plate according to any of the preceding fourth items, wherein the coupling part is substantially flat.

9. Base plate according to any of the preceding fourth items, wherein the coupling part comprises a first coupling part section and a second coupling part section, wherein the coupling part is configured to receive at least a part of the monitor device between the first coupling part section and the second coupling part section.

10. Base plate according to fourth item 9, wherein the first coupling part section and the second coupling part section are biased towards each other.

11. Base plate according to any of the preceding fourth items, wherein the coupling part comprises a protruding part protruding in a protruding direction being substantially perpendicular to a base plate plane, the protruding part having concave sides forming the locking section of the coupling part, the protruding part being configured to engage with a cavity of the monitor device.

12. Base plate according to fourth item 11, wherein the protruding part comprises a socket configured to receive a protruding element positioned in the cavity of the monitor device.

13. Base plate according to fourth item 12, wherein the socket has a triangular cross section.

14. A monitor device for connecting to a base plate of an ostomy appliance, the monitor device comprising:
 a monitor device housing;
 electronic circuitry; and
 an appliance interface configured for connecting the monitor device to the base plate, the appliance interface comprises a plurality of terminals for connecting with a plurality of electrodes of the base plate, the appliance interface comprises a monitor device coupling part configured for coupling between the monitor device and the base plate;
wherein the monitor device comprises a locking mechanism configured to engage with a locking section of the base plate to lock the monitor device in a coupled position with the base plate.

15. Monitor device according to fourth item 14, wherein the monitor device coupling part is configured to engage with the base plate by a linear motion in an engagement direction of the monitor device relative to the base plate.

16. Monitor device according to any of fourth items 14-15, wherein the locking mechanism is biased towards locking of the locking mechanism.

17. Monitor device according to any of fourth items 14-16 comprising a locking element configured to unlock or lock the locking mechanism upon user interaction with the locking element.

18. Monitor device according to fourth item 17 as dependent on fourth item 15, wherein the locking element comprises a first button being deflectable in a first direction, wherein the first direction is substantially parallel or perpendicular to the engagement direction.

19. Monitor device according to fourth item 17, wherein the locking element comprises a first button and a second button, the first button being deflectable in a first direction and the second button being deflectable in a second direction, wherein the first direction is substantially opposite the second direction.

20. Monitor device according to fourth item 19 as dependent on fourth item 15, wherein the first direction and the second direction are substantially perpendicular to the engagement direction.

21. Monitor device according to any of fourth items 17-20, wherein the locking element comprises a slider being slidable in a first slider direction, and wherein the slider is spring loaded and biased towards a second slider direction, wherein the first slider direction is opposite the second slider direction.

22. Monitor device according to fourth item 21 as dependent on fourth item 15, wherein the first slider direction and the second slider direction are substantially perpendicular to the engagement direction.

23. Monitor device according to any of fourth items 14-22 comprising an opening for receiving a coupling part of the base plate, and wherein the locking mechanism comprises a locking component positioned inside the opening.

24. Monitor device according to fourth item 14-22 comprising a clamp configured to clamp a coupling part of the base plate between a first clamp surface and a second clamp surface, and wherein the locking mechanism comprises a locking component positioned between the first clamp surface and the second clamp surface.

25. Monitor device according to fourth item 24, wherein the plurality of terminals is provided on the first clamp surface.

26. Monitor device according to any of fourth items 24-25, wherein the first clamp surface and the second clamp surface is biased towards each other.

27. Monitor device according to any of fourth items 24-26 comprising a clamp lock configured to lock the first clamp surface and the second clamp surface in a closed clamp position.

28. Monitor device according to fourth item 27, wherein the clamp lock is configured to be unlocked by user interaction.

29. Monitor device according to any of fourth items 11-28, wherein the monitor device coupling part comprises a cavity and one or more deflectable elements positioned in the cavity, the cavity being configured to receive a protruding part of the base plate, and the deflectable elements forming part of the locking mechanism being configured to engage with concave sides of the protruding part.

30. Monitor device according to fourth item 29, wherein the monitor device coupling part comprises a protruding element being positioned in the cavity.

31. Monitor device according to fourth item 30, wherein the protruding element has a triangular cross section.

32. Monitor device according to any of fourth items 30-31, wherein the plurality of terminals is provided on the protruding element.

Exemplary embodiments of the present disclosure are set out in the following fifth items:

1. A base plate for an ostomy appliance, the base plate comprising:
   a top layer;
   a first adhesive layer;
   an electrode assembly comprising a plurality of electrodes; and
   a monitor interface configured for connecting the base plate to a monitor device, the monitor interface comprising a plurality of terminals electrically connected to the plurality of electrodes and configured to connect with respective terminals of the monitor device, and the monitor interface comprising a coupling part configured for coupling between the monitor device and the base plate,
wherein the coupling part is configured to engage with the monitor device by a linear motion in an engagement direction of the monitor device relative to the base plate.

2. Base plate according to fifth item 1, wherein the top layer and first adhesive layer are substantially planar and extending in a base plate plane, and wherein the engagement direction is substantially parallel to the base plate plane.

3. Base plate according to any of the preceding fifth items, wherein the engagement direction is towards a stomal opening of the base plate.

4. Base plate according to any of the preceding fifth items comprising a locking mechanism configured to lock the monitor device in a coupled position with the base plate.

5. Base plate according to fifth item 4, wherein the locking mechanism is biased towards locking of the locking mechanism.

6. Base plate according to any of fifth items 4-5 comprising a locking element configured to unlock and/or lock the locking mechanism upon user interaction with the locking element.

7. Base plate according to fifth item 6, wherein the locking element comprises a first button being deflectable in a first direction, wherein the first direction is substantially parallel to the engagement direction.

8. Base plate according to fifth item 6, wherein the locking element comprises a first button and a second button, the first button being deflectable in a first direction and the second button being deflectable in a second direction, wherein the first direction is substantially opposite the second direction.

9. Base plate according to fifth item 8, wherein the first direction and the second direction are substantially perpendicular to the engagement direction.

10. Base plate according to any of fifth items 6-9, wherein the locking element comprises a slider being slidable in a first slider direction, and wherein the slider is spring loaded and biased towards a second slider direction, wherein the first slider direction is opposite the second slider direction.

11. Base plate according to fifth item 10, wherein the first slider direction and the second slider direction are substantially perpendicular to the engagement direction.

12. Base plate according to any of the preceding fifth items, wherein the coupling part forms a USB type port.

13. A monitor device for connecting to a base plate of an ostomy appliance, the monitor device comprising:
   a monitor device housing;
   electronic circuitry; and
   an appliance interface configured for connecting the monitor device to the base plate, the appliance interface comprises a plurality of terminals for connecting with a plurality of electrodes of the base plate, the appliance interface comprises a monitor device coupling part configured for coupling between the monitor device and the base plate;
wherein the monitor device coupling part is configured to engage with the base plate by a linear motion in an engagement direction of the monitor device relative to the base plate.

14. Monitor device according to fifth item 13 comprising a locking mechanism configured to lock the monitor device in a coupled position with the base plate.

15. Monitor device according to fifth item 14, wherein the locking mechanism is biased towards locking of the locking mechanism.

16. Monitor device according to any of fifth items 14-15 comprising a locking element configured to unlock or lock the locking mechanism upon user interaction with the locking element.

17. Monitor device according to fifth item 16, wherein the locking element comprises a first button being deflectable in a first direction, wherein the first direction is substantially parallel to the engagement direction.

18. Monitor device according to fifth item 16, wherein the locking element comprises a first button and a second button, the first button being deflectable in a first direction and the second button being deflectable in a second direction, wherein the first direction is substantially opposite the second direction.

19. Monitor device according to fifth item 18, wherein the first direction and the second direction are substantially perpendicular to the engagement direction.

20. Monitor device according to any of fifth items 16-19, wherein the locking element comprises a slider being slidable in a first slider direction, and wherein the slider is spring loaded and biased towards a second slider direction, wherein the first slider direction is opposite the second slider direction.

21. Monitor device according to fifth item 20, wherein the first slider direction and the second slider direction are substantially perpendicular to the engagement direction.

22. Monitor device according to any of fifth items 13-21, wherein the monitor device coupling part forms a USB type plug.

The invention claimed is:
1. A base plate for an ostomy system, the base plate comprising:
   a monitor interface including:
      a plurality of terminals configured to electrically couple the base plate to a monitor device of the ostomy system, and
      a coupling part configured to releasably and structurally couple the base plate to the monitor device.

2. The base plate of claim 1, wherein the coupling part comprises a rim and a base, with the base secured to the base plate and the rim projecting in a radial direction away from the base and the base plate;
wherein the plurality of terminals is electrically exposed on a perimeter of the rim.

3. The base plate of claim 1, wherein the coupling part comprises a rim and a base, with the base secured to the base plate and the rim projecting in a radial direction away from the base and the base plate;
wherein the rim further comprises an alignment member configured to guide the monitor device from an attachment position to a secured position with the coupling part.

4. The base plate of claim 3, wherein the alignment member is a threaded coupling.

5. The base plate of claim 3, wherein the alignment member is a threaded coupling formed on an outer surface of the rim.

6. The base plate of claim 3, wherein the alignment member is a threaded coupling comprising a channel adapted for rotational coupling of the monitor device to the coupling part.

7. The base plate of claim 3, wherein the alignment member is a threaded coupling comprising a channel, and the channel includes an entry opening adjacent a distal end of the rim and a stop adjacent the base.

8. The base plate of claim 1, wherein the coupling part comprises a rim and a base, with the base secured to the base plate and the rim extending distal relative to the base and the base plate, with the base plate further comprising a waterproofing element disposed at a location where the rim meets the base.

9. The base plate of claim 8, wherein the waterproofing element is a ring disposed around the rim at the location where the rim meets the base.

10. The base plate of claim 8, wherein the waterproofing element is formed from one of rubber, polyurethane, and silicone material.

11. The base plate of claim 8, wherein the waterproofing element is releasably attached to the base plate.

12. The base plate of claim 1, wherein the coupling part comprises a magnet adapted to couple with a magnetic element of the monitor device.

13. The base plate of claim 1, wherein the base plate further comprises a first adhesive layer adapted to adhere the base plate to skin of a user and the plurality of terminals is coupled to the first adhesive layer.

14. The base plate of claim 1, wherein the coupling part is adapted to form a releasable mechanical and electrical coupling with the monitor device.

15. The base plate of claim 1, wherein the base plate comprises a first adhesive layer adapted to adhere the base plate to skin of a user and the plurality of terminals is provided in an electrode assembly that is coupled to the first adhesive layer.

16. The base plate according to claim 1, wherein, when the monitor device is connected to the coupling part, the monitor device is adapted to collect ostomy data from the base plate.

* * * * *